US007648964B2

(12) United States Patent
Laurie et al.

(10) Patent No.: US 7,648,964 B2
(45) Date of Patent: Jan. 19, 2010

(54) USE OF LACRITIN IN PROMOTING OCULAR CELL SURVIVAL

(75) Inventors: Gordon W. Laurie, Charlottesville, VA (US); Jiahu Wang, Nepean (CA)

(73) Assignee: University of Virginia Patent Foundation, Charlottesville, VA (US)

(*) Notice: Subject to any disclaimer, the term of this patent is extended or adjusted under 35 U.S.C. 154(b) by 118 days.

(21) Appl. No.: 11/596,506

(22) PCT Filed: May 6, 2005

(86) PCT No.: PCT/US2005/016112

§ 371 (c)(1), (2), (4) Date: Nov. 13, 2006

(87) PCT Pub. No.: WO2005/119899

PCT Pub. Date: Dec. 15, 2005

(65) Prior Publication Data

US 2007/0207522 A1 Sep. 6, 2007

Related U.S. Application Data

(60) Provisional application No. 60/570,865, filed on May 13, 2004.

(51) Int. Cl.
- A61K 38/18 (2006.01)
- C07H 21/04 (2006.01)
- C12P 21/04 (2006.01)
- C07K 14/475 (2006.01)

(52) U.S. Cl. .................. 514/12; 514/2; 435/69.1; 435/69.7; 435/320.1; 530/300; 530/399; 536/23.1; 536/23.5; 536/23.7

(58) Field of Classification Search .................. None
See application file for complete search history.

(56) References Cited

U.S. PATENT DOCUMENTS

| 7,459,440 B2 * | 12/2008 | Laurie et al. .................. 514/12 |
| 2002/0102604 A1 | 8/2002 | Milne et al. |
| 2002/0164669 A1 | 11/2002 | Ruben et al. |

FOREIGN PATENT DOCUMENTS

| WO | WO 98/27205 A2 | 6/1998 |
| WO | WO 98/35229 A1 | 8/1998 |

OTHER PUBLICATIONS

Sanghi et al (Journal of Molecular Biology. Jun. 2001, vol. 310, No. 29, pp. 127-139.*
Journal of Molecular Biology. Jun. 2001, vol. 310, No. 29, pp. 127-139.*
A. J. Lumsden, et al., "Paired Oligonucleotide Screening for BM180 in a Human Lacrimal Gland cDNA Library: Clone HL-2," American Society for Cell Biology Annual Meeting (1998).
Sandhya Sanghi, et al., "cDNA Cloning and Expression of lacritin', a Novel Secreted Glycoprotein of the Lacrimal Gland," American Society for Cell Bilogy Annual Meeting (1999).
Sandhya Sanghi, et al., "Quantitation of Rat Lacrimal Secretion: a Novel Sandwich ELISA with High Sensitivity," Experimental Eye Research, Academic Press (2000).
C. Hirst, et al., "High Levels of CUG-initiated FGF-2 expression cause chromatin compaction, decreased cardiomyocyte mitosis, and cell death", Molecular and Cellular Biochemistry 246: 111-116, 2003.
M. Beir, et al., "Transforming growth factor beta mediates apoptosis in the ganglion cell layer during all programmed cell death periods of the developing murine retina", Neuroscience Research 56 (2006), 193-203.
Joo-Young Im, et al., "COX-2 Regulates the insulin-like growth Factor I-induced Potentation of $Zn^{2+}$—toxicity in Primary Cortical Culture", Molecular Pharmacology, 66:368-376, 2004.
Zaodung Ling, et al., "Progressive dopamine neuron loss following supra-nigral lipopolysaccharide (LPS) infusion into rats exposed to LPS prenatally", Experimental Neurology 199 (2006), 499-512.
Erina Kuranaga, et al., "Fas/Fas Ligand System in Prolactin-Induced Apoptosis in Rat Corpus Luteum: Possible Role of Luteal Immune Cells", Biochemical and Biophysical Research Communications 260, 167-173 (1999).
Emanuela Matteucci, et al., "Hepatocyte growth factor induces apoptosis through the extrinsic pathway in hepatoma cells: favouring role of hypoxia-inducible factor-1 deficiency", Oncogene (2003) 22, 4062-4073.
Doug Lobner, et al., "Mechanisms of bFGF and NT-4 potentiation of necrotic neuronal death", Brain Research 954, (2002) 42-50.
Victor T. Solovyan, et al., "Proteolytic Activation of Latent TGF-β Precedes Caspase-3 Activation and Enhances Apoptotic Death of Lung Epithelial Cells", Journal of Cellular Physiology 207:445-453 (2006).
Vincenzo C. Russo, et al., "Fibroblast Growth Factor-2 Over-Rides Insulin-like Growth Factor-I Induced Proliferation and Cell Survival in Human Neuroblastoma Cells", Journal of Cellular Physiology 199:371-380 (2004).
Heidi M. Sowter, et al., "Predominant Role of Hypoxia-Inducible Transcription Factor (Hif)-1α versus Hif-2α in Regulation of the Transcriptional Response to Hypoxia[1]", Cancer Research 63, 6130-6134, Oct. 1, 2003.

* cited by examiner

*Primary Examiner*—Robert B Mondes
*Assistant Examiner*—Padma V Baskar
(74) *Attorney, Agent, or Firm*—Rodney L. Sparks

(57) ABSTRACT

The present invention relates to the use of lacritin, and fragments, derivatives, and homologs thereof, and nucleic acid sequences encoding that protein. The invention relates to the use of lacritin as a growth factor human corneal epithelial cells and other select epithelial cells. The invention also relates to the use of lacritin in promoting ocular cell survival in response to an insult or injury, in protecting against ocular inflammation, and in promoting ocular wound repair.

8 Claims, 17 Drawing Sheets

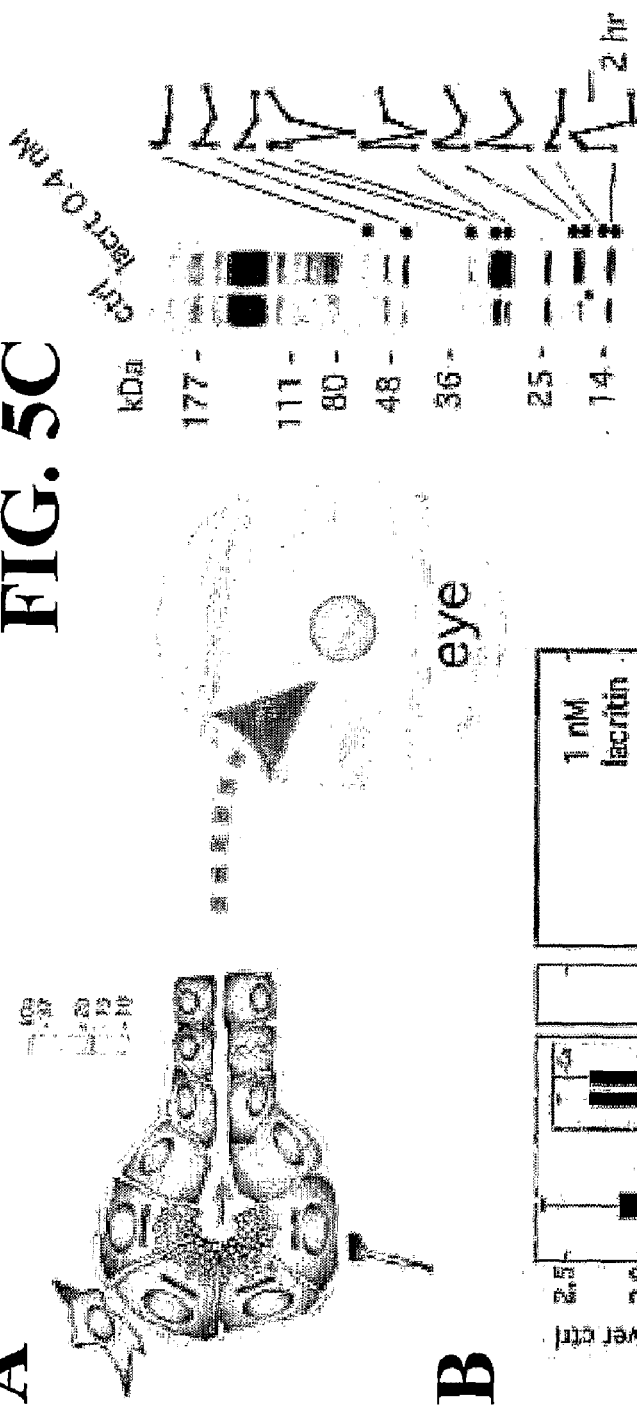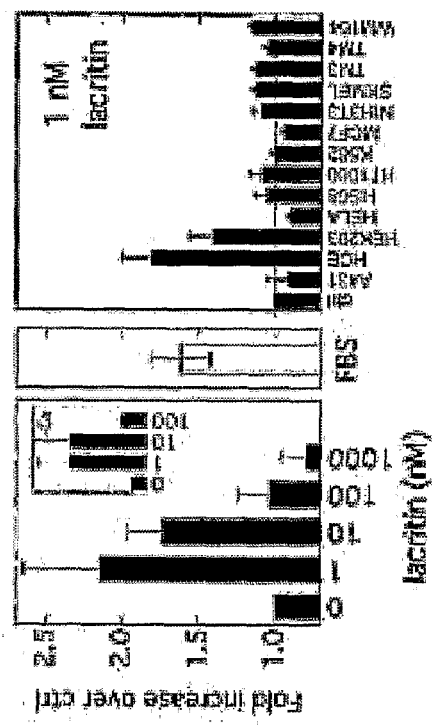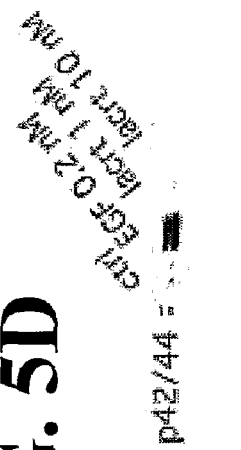
FIG. 5A
FIG. 5B
FIG. 5C
FIG. 5D

SEQUENCE LISTING

<160> NUMBER OF SEQ ID NOS: 37

<210> SEQ ID NO 1
<211> LENGTH: 12354

```
<212> TYPE: DNA
<213> ORGANISM: Homo sapiens
<220> FEATURE:
<221> NAME/KEY: exon
<222> LOCATION: (5194)..(5250)
<220> FEATURE:
<221> NAME/KEY: sig_peptide
<222> LOCATION: (5194)..(5250)
<220> FEATURE:
<221> NAME/KEY: exon
<222> LOCATION: (6801)..(6855)
<220> FEATURE:
<221> NAME/KEY: exon
<222> LOCATION: (7654)..(7794)
<220> FEATURE:
<221> NAME/KEY: exon
<222> LOCATION: (8196)..(8296)
<220> FEATURE:
<221> NAME/KEY: exon
<222> LOCATION: (9081)..(9143)

<400> SEQUENCE: 1
acatttttaa aatttttca ctcattgctt tgtctttaca cctccccgat ggccaaggtg      60
gaagatcgga ggcatcacag gagtgtggca gagcttgtgc aggccacagg gcttggcaga    120
gaagacaagc catgtcgagc acagcagcca gggtagaatg ccctcggag atcaacgtgt     180 gcctgtgtct ccaatgcagg agcagtctac cctaaatagt ccatgtcaat tcctcccttt    240
ggagtctctg cttccccacc agcccccaga acatggccta acacacaggg aggggaatga    300
ggaaaagaca ttcatcacag ttcagacagg aagtggtgta tcagtggaga ggtccaagta    360
gaaaacaaat ggcacactca ggagggctta tatatatata taaatacttt aagttctagt    420
gtacatgtgc acaatgtgca ggtttgttac atatgtatac atgtgccgtg ttggtttgct    480
gcacccatta actcatcatt taccttaggt atttctccta atgctatccc tcccccatcc    540
ccccacccca caacaggcct cggtgtgtga tgttccccac cctgtgtcca agtgttgtca    600
ttgttcaatt cccacctatg agtgagaaca tgtggtgttt ggttttctgt ccttgcgata    660
gtttgctcag aatgatggtt ccagctttta tccatgtccc tacaaaggac atgaactcaa    720
ccttgtttat ggctgcatag tattccatgg tgtatatgtg ccacattttc ttaacccagt    780
ctatcattga tggacatttg ggttggttcc aagtctttac tattgtgaat agtgccacaa    840
taaacataca tgtgcatgca tctttatagt agcatgattt ataatccttt gggtatatac    900
ctagtaatgg gatctttggg ttaaatggta tttctagttc tagatccttg aggaatcgcc    960
acactgtctt ccacaatggt tgagctagtt tacactccca ccgatggtgt aaaagcattc   1020
ctatttctcc acatcctctc cagcacctgt tgttcctga cttttaatt attgccattc    1080 taactactgt gagatgatat ctcattgtgg ttttgatttg catttctctg atggccagtg   1140
atgatgagca ttttttcatg tgtctgctgg ctgcataaat ctcttctttt caaaagtgtc   1200
tgtccatatc ctttgcccac ttttttgatgg ggttgtttga ttttttcttg taaatttgtt   1260
taagttcttt gtagattctg gatattagcc ctttgtcaga tgggtagatt gcaaaaattt   1320
tctcccattc tgtaggctgc ctgttcactc tgatggtagt ttcttttgct gtgcagaagc   1380
tctttagttt aattagatcc catttgtcta ttttggcttt tgttgccatt gcttttggtg   1440
ttttagtcat gaagtacttg cccatgccta tgtcctgaat ggtattgccc aggttttctt   1500
ctagggtttt tatggtttta ggtctaacat ttaagtcttt aatctatctt gaattaattt   1560 tgtataagg tgtaaggaag ggatccagtt tcagctttct acatatggct agccagtttt    1620
cccagcacca tttattaaat aaggaatcct ttccccattt cttgttttg tcaggtttgt    1680
```

```
caaagatcag atggttgtag atgtgtggtg ttatttctga ggcctctgtt ctgttccatt    1740
ggtctatatc tgttttggca ccagtaccat gctgttttgg ttactgtaag ctggtagtat    1800
agtttgaagt caggtaatgt gatgcctcca gctttgttct ttttgcttag gattgtcttg    1860
gcaatgcagg ccctttttgg gttccatatg aactttaaag tagtttttc cacttctgtg     1920 aagaaagtca ttggtagctt gatggggatg cattgaatc tctaaattac cttgggcagt     1980
atggccattt tcacgatatt gattcttcct atccaagagc atggaatgtt cttccatttg    2040
tttgtgtcct cttatttcat tgagcagtgg tttgtggttc tcaggagggc ttttttttaaa    2100 aaaggttctt taaggaaaaa tgtatctatt atttacagag attcaagtat ggactagcaa    2160
cagcaggaag tctgaagcag cgtgttgggg ggtgggggtg aataatgtca cctgacaaca    2220
agagatggcg ctctgaaaca gggaccagac agaagctgca gtcagagaga aacagccatt    2280
gccacaccat gctgcattaa gtatccgtgg ctgtaaaaat tattcaaaca tttggtggct    2340
tcacacatga tttcttatcc acagttgtta tggatcagca gtccaggtac agatgcgccc    2400
tcagacacag agtctctaat gaggctgcag tcaaggtatc atcgaggctg cggtcaccctc   2460 aaaactcagc tgaggaaaga cccacttcca agctcagtca cgtggtagct ggcagggttg    2520
agttcctcac agatagctgg actaagggcc tcggctcctt actggctaca ggctggaggc    2580
tgtcctcggt tcttgccac gtaggtctct ccacaggaca gcctcacaca tggccactca     2640
cttcatcaga gcaagctgag aagatccaga gacagagtgt gtgtaaacaa gactaaagtc    2700
atagtctcag aactgactac ctcatcactt tgccatcttc tatttgttag gagtgaatct    2760
cgagacccag cccagttaag cagaggaaat tacagcaggg caccaatgcc aagacgtagg    2820
catcaccagg agctatctct gaagtcgtcc taccacacat gccaaagcaa gagagggagc    2880
aggaggaaca aatgccttga tctctccctt ttcccaccct cccatctccc acctgtgtct    2940
cccattggcc aaactcaact cgaagctaga gggcatggga gcccaggtga tacagcccat    3000
agaggcatcc ttccagacca gtgcagagat gagagagaat aaacctgagg cagaggggag    3060
agaggtacaa cgagcagccc atgagacaag acacagatca gcgaactgac agtcatcatg    3120
gaggtcagat aacctagaaa acaagacatc acacagagca gccctcacc catatccatg      3180 aggtccgtca agacattgca cagagcagcc tctcacccat atccatgagg tctgcctctt     3240
taatctatgc acccaattct ttcccaggct ctataatttg gggtaacatt tctctgggcc    3300
ctgttataga ataatgaaaa ttttctataa aacaaatgtc cttactttca cctcatccct    3360
atttatgtaa atgcttgcct ctttaattac tgaggccagg aggaagattt gggagaggaa     3420
agggctatgc ggtgacattt ggaaagaccc tgctctgtga cagttctagt gttgacgcca    3480
aagttctcat ttcctcttag aaaagtcttg tgcaaatagc ataatttgct cctgttgact    3540
tttttaatgt gctcatggag actgctcggg atctagatct gtttgggatc tgcaggactt    3600
ctccttctgc agtgtacaca cacgtgcaca cacgtatgtg cacataccca gggcactggt    3660
gccatcaaaa ctttctcttg ttcttcagcc ttccccattc caggtaaggc caccaccacc    3720
ttcaaggctc ccaggcccag accctcaggc aggtagcaat tgccaaggct ttaatgtccc    3780
accccattaa ttttatcttc ctttatctcc tgaaaagatt aatgttctaa accctggcac    3840
ccaaaacacc ctcatgttga aaactcttca atacccctt ctcacactca tcttcagagc    3900
taccatgagg cagagaagcc tccggaatca gcccacatgg ggctgggtga atgccaacac    3960
caagcaaggg gaaagtcaca aattgacatc cagcacctta ttctccaccc ttcagcccct    4020
caactgactc ctgctccacg gcccgttcta ttaatatcta gcatttagca ccagcctgga    4080
```

```
caaaaaccta cttggaaaga tggtacaaga accccacaca actccataga acttcgctgt   4140
ctaaaaaaat gctttgccgt atattatccc acttaatctc caccactatg ctgtacatag   4200
gagccacaac tcctagacaa caaataaaaa tcctatcact tttcaaatcc taacattttc   4260
atatgacaaa gccagaactc aaaatccaga cctctagagt cccagatcag gaaaggaaga   4320
aacgccaagt caaagagaag cttctttaga ataatctgct tttctggatt attcacacca   4380
tgggtcagct ccccacttga agtcagaacc aagctccaat ttcagtgaac caccatcatg   4440
ctttgaccag gagattctct cagaaatgtg gggtcccatt gagtaggcct gaagacagag   4500
attgacaggc ctatgtgagc ctggaggagt tcttttagg ggctggataa tgtcaagaac   4560
agagaacaac tccagagaag gcacacacgc cttcaaaccc atccctcat ggggagaaag   4620 cagccaggaa ctcaggcctc aagtgttcta ggtgtggtct cccaaggaaa cgggctcact   4680
tagtttgggg aaaccttcaa accctgcact gagtcctatg tagactggga cagaaggtgg   4740
acaatgtaat cccctgagcc ctcaacctcc tcctggagag atgacaagat taagatttct   4800
ctaccagaac cctcaacaga cacatcccag aatctcccca agtgaaatgt gctctaccta   4860
ccgtccctga gagcccaggg gtgtgaaccc agagggcagg tgtggtgggg aagggaggag   4920
ggagaaagaa aagggatggc tgggagttag agaaaggctc ctatccagga cctgcctgca   4980
aggatcccag gtatcagcca gcccaaccta gcccttgttg acttagcagg tgacagtttg   5040
gggaagaagg ggaggaggat gcggaagtca cacctctcca ggcttggttc ccattggccc   5100
ttgatatcct taaaagggcc cagcaatttc agcatcctta ttccccagac cttctgcaga   5160
ttctgtggtt atactcactc ctcatcccaa aga atg aaa ttt acc act ctc ctc   5214
                                    Met Lys Phe Thr Thr Leu Leu
                                      1               5 ttc ttg gca gct gta gca ggg gcc ctg gtc tat gct ggtgagtatg           5260
Phe Leu Ala Ala Val Ala Gly Ala Leu Val Tyr Ala
        10                  15 gcctttcctc tgcgccccac aagagtcctc ccagtccaag gagcccctca ctcctgcctt   5320 caccccctctc ctcctctctc agtgctattc tggtttccct gcctctgcaa gtgactcctc   5380
tcccagttct ccacacgtgg cctctgcacc ccactggcca gaggaaccca gaactctctg   5440
gcctctgcct gccctcccag ctcatctcct cacacaccat tgtttaccca ctatgcctca   5500
gctacactgg cttctctggt gtcccctgca tgtagttgag cagggtgtcc cctacacgag   5560
ggtgcccagg caaggagtgg tagaagctaa aatctggccg acactctact tgccaagcag   5620
tgagcctggc ccctggctgt gtctcttagg aggaagggat gccttttttt tttttttttt   5680
tttgagaccg agtctccctc tgttgcccag gctggagtgc agtggcacga tctctgctca   5740
ctgcaacatc cacctcctgg gttccagcga ttatcttgcc tcagcctcct gggtagctgg   5800
gactacaggc tcatgccacc ttgcccagct aattttgtat ttttagtaga cggtgttt     5860 caccatgttg gccaggttgg tctcgaactc ctgacctcag gtgatccgac tgccttggcc   5920
tcccaaagtg ttggaattac aggcgtgagc caccgtgccc tgctgggatg cctttttga   5980 tccacagaag cactatttgg gccatgatga tcctgctgtt ccttgaacat caggatcttc   6040
cttcttgtcc tttcctcgtc tagaatgctt ccctctccc tggcccccttc ccccaaccaa   6100 ctctaatgtc acctggccaa tgattttca tctagaaaat ctcagtttac atataattcc   6160
ccaaaaaggc cttccatgca catgcggaac aaatcagatc catgtgccct tctcgcacca   6220
ggctgcacgt tcccttccag cactgtcaca ccagccatta ataatttcg taaaaggaca   6280
```

```
gatgtaagct ctgtcagggc aggggtcttg tctgccctct tcagcactgc acctccatct   6340
cttggcacag agctttgcat aaatgttgtg ttgaaagaat aaagggaatc aaggctgggg   6400
tctcaatcct gcaaatcgct caaatatggc cccataaccc ccacatactg tcctcctcca   6460
ccacagagga ggttgagccc ctctgaccat ggccagctcc atgacagaca cctcaggaa    6520 gcctaccaag ccaggggcca gtcaggagga aggcactgtt ccaagagaca ttacacttct   6580
cagaggggaa gttatttcaa aagccacagg agttaaacat cagagagtgc cccagtagac   6640
ccgctgatat ggtggaaggg catgtccaac ccaaagggaa attgatcccc ttctatccat   6700
gagcattccc aggagataag ctttgggaat ggggagggag ggtggctcga gtaggtccgg   6760
ttcggtcctt gctctcatct ggcatgtttc ccccattgca gaa gat gcc tcc tct    6815
                                                Glu Asp Ala Ser Ser
                                                            20 gac tcg acg ggt gct gat cct gcc cag gaa gct ggg acc t gtgagtcctc   6865
Asp Ser Thr Gly Ala Asp Pro Ala Gln Glu Ala Gly Thr
25                  30                  35 ctctccctgc tgccctagcc ctcgttggga aggtttaaca gttagggatg tgagtggtgg   6925
ctgggagaag aagccagtgg gaggagatct ggattctgtg cttggtggta atggggaggg   6985
gcaggtaata taataaagaa ggtggcatgg gttgaaatgg tacaaggcta aggacaaaag   7045
aggatgaccc agagaggcaa ggacaatagg gagcatgggg aaaaggttat tgtgaataaa   7105
agggagagaa acatgaggtt aagtggtaag ggcaatgtct cacatggcat taataccttc   7165
acctgcaaac acctcccatt actcccaatt ccttagcaag ataaccatta tctggcctct   7225
aacctcattt tccaacccca ttttccatga ctctctttta tgtcgcaccc ccatcagcta   7285
aattgaactt gtttccattc cccacacatg ccttcgcctg acctcttact cactgcctgc   7345
ccccagggaa gccccttttgg tacatcctct cctgctaaca tcctgccttc aagatccagc  7405
ttctctatga agtgctcccc gattctcacc atccccctagt ccaaatcctt ccccaaccct  7465
gcccgctgca ttccaagaga cacacagcat gcagaaatgc tatctcccctt aaggggggcag 7525 cgtttaagcc atatcacttc tgtatcctgg cacccagcac acattaggta tcctggggcc   7585
ctgcaaccca ttccaaaaga aacaaacact ttcactttgc taaaatccat caatttgtgc   7645 attcacag ct  aag cct aat gaa gag atc tca ggt cca gca gaa cca gct    7694
            Ser Lys Pro Asn Glu Glu Ile Ser Gly Pro Ala Glu Pro Ala
                   40                  45                  50 tca ccc cca gag aca acc aca aca gcc cag gag act tcg gcg gca gca     7742
Ser Pro Pro Glu Thr Thr Thr Thr Ala Gln Glu Thr Ser Ala Ala Ala
    55                  60                  65 gtt cag ggg aca gcc aag gtc acc tca agc agg cag gaa cta aac ccc     7790
Val Gln Gly Thr Ala Lys Val Thr Ser Ser Arg Gln Glu Leu Asn Pro
 70                  75                  80 ctg a gtaagtctct gtctctatgc cagatcaaca acctagaaaa gtctctggct         7844
Leu gcaggcccac atcacacctc cacgcacaga gataagcctg gtgagaagca ggtagactca   7904
aacagctgaa cacaaaggca caaatgggat tgtgcattgc acccacacac aacgtttttca  7964 caatagtaga tgttgcagcc tgcacaatac atggtttctg tcctggctca cacaacttcc   8024
tatgagagaa gtgctggagc cctcagcaaa acttctgcac tttaggactt tctgtaggga   8084
tgatgtcctg ggtggagtgg gggtgggggg cgggtgcagg tggggcaatg cagagttctc   8144
tttaaatgag gtgatttttc tgctgatgtg attgttctgc tccaaaatta gaa tcc     8200
                                                           Lys Ser
                                                            85
```

```
ata gtg gag aaa agt atc tta cta aca gaa caa gcc ctt gca aaa gca      8248
Ile Val Glu Lys Ser Ile Leu Leu Thr Glu Gln Ala Leu Ala Lys Ala
         90                  95                 100 gga aaa gga atg cac gga ggc gtg cca ggt gga aaa caa ttc atc gaa      8296
Gly Lys Gly Met His Gly Gly Val Pro Gly Gly Lys Gln Phe Ile Glu
        105                 110                 115 agtgagtgca tcccaaggca aggctttgtg ggaatgagaa tactcaccac ccaccatccg    8356
ggggtgggat atgggacaga acttgccccc atttccacct cacatatgag acttggaatt    8416
gccacagccc ctgctgttga agaccctca ctttgtgctt tcatatgttt ccaatttctc     8476
atccagattc aaattgccag ctgggcacgg tggttcacgc ctgtaatccc agcactttgg    8536
gaggccaagg caggtggatc gcttgagccc aggagttcaa actagcctg gcaacatgg      8596
cgataccca tctctacaaa aaaatacaaa aattagccag cgtggtggc acatgcctgt      8656
agtcccagct acttgggagg ctaaggtggg aggatcacct gagcccgtga ggcagagatt    8716
gcagtgggcc gagattgtgc cactgcactc catcctgggt gacagagaaa gaccctgtct    8776
caaaaaaaaa gaacagattc aatgtgccat gttgtctgat attgattcac ctggggtcta    8836
acccctacc ttcccgcagc agagcctgct tgtttctatt cttgtcccct gcccctgcca     8896
aggtggggaa gagggtaggt ccttcaggct ctggtgaatc taatctcaat ccctccaact    8956
tctgtgtaag cctctccaga gtctcagtaa gtctggaaag cagagatgga attgaggaga    9016
aatggaaggg gtggagctgg tgcctggggt cctaaaagcc tcatttgtct catctttcct    9076
tcta gat gga agt gaa ttt gca caa aaa tta ctg aag aaa ttc agt cta     9125
    Asp Gly Ser Glu Phe Ala Gln Lys Leu Leu Lys Lys Phe Ser Leu
        120                 125                 130 tta aaa cca tgg gca tga gaagctgaaa agaatgggat cattggactt              9173
Leu Lys Pro Trp Ala
    135 aaagccttaa ataccttgt agcccagagc tattaaaacg aaagcatcca acttgctgtg     9233
tgcctgtgct ctatgggatg ggccctggag gaagtgcagg gagaaaagcc ctccctggac    9293
caacacaagg cataggatgt cctgacccag gcccttggcc agtcacaggc tgcctggaag    9353
gcagagcctc taacaagccc ttttattcac ttggagccac atccacattg ctgagcctcc    9413
tttgagtcca aatgccactc cagttttcgt cccctctta ctcttcacac attactccta     9473
gtgacatttg agcatttcca aaaattaaat caaattccaa agaaccagga tttatcatcc    9533
tgaaaataat caaagcctga gccatttata ctaaagccac tttctggtac ctttatcaga    9593
aattcatctc tcctgccctc tattcgtaca ttctacactg gccaaagtg gctggcaatg     9653
gctaattagg tcagacagta aagtaatgag ctactacagt gacaactggc acttggctaa    9713
gaagaccaat tgaatccatt aaggttattc ttgtgatgtg gtgcagagaa accacttttg    9773
actgtgctct agatgtgcaa attatcttcc ccaaaggact aaagtctctc aaagggtct     9833
tggtcacctc tttctcctcc tgcaactttg ttttcctccc ctacagctca tggctgtgtc    9893
ttgcacacac atgaaccagg gaagatcact catgacttca gggggcaaag aaagcagtca    9953
gatcttctgc cagaccctc cccaggccag gcacagggtc ttctgctctt taacatgccc    10013
ggagccattg attctagact gttcttccca ccccatctta gtttatttc tgttgctcat    10073
aacagaatat ctaaaactgg ataatttata agacgcaaaa tgtacttctt acagttctag   10133
agctaggaag tccaaggtca aggggcatg tctggcaaga gctttcttgc tggcagggaa    10193
tctctgcagg atcccaagct ggaatagaga atcacatagt gaggtggctg tccacgctag   10253
ctcagctctc ttcctcttct tagaaagcct ccagtctcac tcctgtggca aaccattaat   10313
```

-continued

| | | | | | |
|---|---|---|---|---|---|
| ccattaaccc | attaattcat | taatccatag | atggattaat | ctattcacaa | gggcaaagac | 10373 |
| ctcatgaccc | aatcatttct | ttttcttttt | gttttttaag | acagagtcct | gttctgtcgc | 10433 |
| ccacactgga | gttcaacggc | tcaatctcgg | ctcactgcaa | cctctgcctc | ccgggttcaa | 10493 |
| gcaattctcc | tgcctcagcc | tcccaagcag | ctaggattac | aggtgcccac | cgccacacct | 10553 |
| ggctaatttg | ttgtattttt | agtagagacg | gggtttcacc | atgttggcca | ggatggtctc | 10613 |
| aaactcctga | cctcatatga | tccacctgcc | taggcctccc | aaagtgctga | gattacagac | 10673 |
| atgagccact | gcgcccagca | tgaaccaatc | atttcttaat | aaccctgcct | ttcaatattg | 10733 |
| ttactttagg | gattaagttt | caatgtaagt | tttggagggg | acaaacactc | aaactatacc | 10793 |
| attctactcc | tggccctctg | aaactcatgt | ccttctcaaa | tataaatata | ttcattccaa | 10853 |
| ctccatagcc | ccaaaatctt | agctcattcc | agcaccaact | caaaagtcca | agtccagag | 10913 |
| tatcatctgt | gagcctgtga | aatacaaacg | agttatctac | ttttaagata | cagttgtggt | 10973 |
| aaaagcataa | aacagacatt | cccattccaa | aatggaggaa | tagacaaaaa | gaaacgagta | 11033 |
| acaggtctca | agcaaatctg | aaacccagca | gggcagacat | taaatcttaa | agctgaagaa | 11093 |
| taatttcttt | tgactctgtg | tgtggcctcc | catccacaac | ggggtatggg | ttaggccccc | 11153 |
| aagacttcag | gcagcctcac | ccttatggct | ttgctcagtg | cagcccatgt | gactgctcct | 11213 |
| aggtattgga | gtctggtgcc | tgaagctttc | ccaggtgggt | gttgcatact | gccagtgact | 11273 |
| gcacacttct | gggttcccag | tagtggtccc | actcccacag | ctctactagg | cattacccta | 11333 |
| atggagactc | tctacggtgg | caccacttcc | atggctctgc | tagatgggga | ctctttgcag | 11393 |
| tggctctgcc | cctgtgacaa | atctttgcct | gggctcctag | gcttttgatg | atatcctttg | 11453 |
| aaatcttggt | ggaggctgcc | aagctgccac | agcttttgct | gtctgcaagc | ctgcagagtc | 11513 |
| agcaccacct | ggacactgcc | aaggtttatg | gcttctacct | tccaaaactg | cagcacaagc | 11573 |
| tacaattggg | gtcacttgag | ccttggctag | ggcagccatg | aagctctgca | ctggggtttc | 11633 |
| agggcagagt | cccaaggcac | cattctgccc | ttctagacct | ctgggcctat | aacaggaggg | 11693 |
| gcaccctcaa | agatctctga | aatgcatttc | aggtctttct | tcatcgtctt | gagaaatagc | 11753 |
| atccggctcc | cttctatctg | tgctaatctt | tttagctgca | cccttgatct | cctcttctga | 11813 |
| atgtgctttt | tcactcttca | tgtggccagg | ctgacagttt | tccaactctt | tccactctgc | 11873 |
| ttccagttta | atgtaaattt | tctttatctt | tataattgtc | tttgaattat | tcctttgctc | 11933 |
| ccaaatctca | gcataagtgg | ccaaaagtaa | ccatgcacct | ccttctatat | tttgcttaga | 11993 |
| aatttcttct | gcagatactc | tagttcgtca | ctctcaagtt | tggccttcca | caaagccctt | 12053 |
| aaatgtagac | acagttcagt | caagttctct | gtcaatttat | aacaaggatg | gtctttactc | 12113 |
| cagtttccaa | taccttattc | ctcagttcca | tctgaaatct | catcagaatg | gccttactgt | 12173 |
| tcatatttca | actagcattc | tggtcacaat | cacttaacaa | atctctaaga | agttccaaac | 12233 |
| tttccaaaga | actgaggtgc | tccatgagtt | ctccacccct | gcagcaaact | tctgcctgga | 12293 |
| catctaggtg | ttttcataca | tcctctgaaa | tctaggtgga | ggttcccaaa | ccccaattct | 12353 |
| t | | | | | | 12354 |

<210> SEQ ID NO 2
<211> LENGTH: 522
<212> TYPE: DNA
<213> ORGANISM: Homo sapiens

<400> SEQUENCE: 2

-continued

```
gaattcgcgg ccgcgcagat tctgtggtta tactcactcc tcatcccaaa gaatgaaatt      60
taccactctc ctcttcttgg cagctgtagc aggggccctg gtctatgctg aagatgcctc     120
ctctgactcg acgggtgctg atcctgccca ggaagctggg acctctaagc ctaatgaaga     180
gatctcaggt ccagcagaac cagcttcacc cccagagaca accacaacag cccaggagac     240
ttcggcggca gcagttcagg ggacagccaa ggtcacctca gcaggcagga actaaacccc     300
cctgaaatcc atagtggaga aagtatctt actaacagaa caagcccttg caaaagcagg      360
aaaaggaatg cacggaggcg tgccaggtgg aaaacaattc atcgaaaatg gaagtgaatt     420
tgcacaaaaa ttactgaaga aattcagtct attaaaacca tgggcatgag aagctgaaaa    480
gaatgggatc attggactta aagccttaaa taccttgta gc                        522
```

<210> SEQ ID NO 3
<211> LENGTH: 416
<212> TYPE: DNA
<213> ORGANISM: Homo sapiens

<400> SEQUENCE: 3

```
tgaaatttac cactctcctc ttcttggcag ctgtagcagg ggccctggtc tatgctgaag      60
atgcctcctc tgactcgacg ggtgctgatc ctgcccagga agctgggacc tctaagccta    120
atgaagagat ctcaggtcca gcagaaccag cttcaccccc agagacaacc acaacagccc    180
aggagacttc ggcggcagca gttcagggga cagccaaggt cacctcaagc aggcaggaac    240
taaaccccct gaaatccata gtggagaaaa gtatcttact aacagaacaa gcccttgcaa    300
aagcaggaaa aggaatgcac ggaggcgtgc caggtggaaa acaattcatc gaaaatggaa    360
gtgaatttgc acaaaaatta ctgaagaaat tcagtctatt aaaaccatgg gcatga        416
```

<210> SEQ ID NO 4
<211> LENGTH: 138
<212> TYPE: PRT
<213> ORGANISM: Homo sapiens

<400> SEQUENCE: 4

```
Met Lys Phe Thr Thr Leu Leu Phe Leu Ala Ala Val Ala Gly Ala Leu
  1               5                  10                  15

Val Tyr Ala Glu Asp Ala Ser Ser Asp Ser Thr Gly Ala Asp Pro Ala
             20                  25                  30

Gln Glu Ala Gly Thr Ser Lys Pro Asn Glu Glu Ile Ser Gly Pro Ala
         35                  40                  45

Glu Pro Ala Ser Pro Pro Glu Thr Thr Thr Thr Ala Gln Glu Thr Ser
     50                  55                  60

Ala Ala Ala Val Gln Gly Thr Ala Lys Val Thr Ser Ser Arg Gln Glu
 65                  70                  75                  80

Leu Asn Pro Leu Lys Ser Ile Val Glu Lys Ser Ile Leu Leu Thr Glu
                 85                  90                  95

Gln Ala Leu Ala Lys Ala Gly Lys Gly Met His Gly Gly Val Pro Gly
            100                 105                 110

Gly Lys Gln Phe Ile Glu Asn Gly Ser Glu Phe Ala Gln Lys Leu Leu
        115                 120                 125

Lys Lys Phe Ser Leu Leu Lys Pro Trp Ala
    130                 135
```

<210> SEQ ID NO 5
<211> LENGTH: 5193
<212> TYPE: DNA

<213> ORGANISM: Homo sapiens

<400> SEQUENCE: 5

```
acatttttaa aatttttca ctcattgctt tgtctttaca cctccccgat ggccaaggtg      60
gaagatcgga ggcatcacag gagtgtggca gagcttgtgc aggccacagg gcttggcaga     120
gaagacaagc catgtcgagc acagcagcca gggtagaatg ccctcggag atcaacgtgt      180
gcctgtgtct ccaatgcagg agcagtctac cctaaatagt ccatgtcaat tcctcccttt     240
ggagtctctg cttccccacc agcccccaga acatggccta acacacaggg aggggaatga     300
ggaaaagaca ttcatcacag ttcagacagg aagtggtgta tcagtggaga ggtccaagta     360
gaaaacaaat ggcacactca ggagggctta tatatatata taaatacttt aagttctagt     420
gtacatgtgc acaatgtgca ggtttgttac atatgtatac atgtgccgtg ttggtttgct     480
gcacccatta actcatcatt taccttaggt atttctccta atgctatccc tcccccatcc     540
ccccacccca caacaggcct cggtgtgtga tgttccccac cctgtgtcca agtgttgtca     600
ttgttcaatt cccacctatg agtgagaaca tgtggtgttt ggttttctgt ccttgcgata     660
gtttgctcag aatgatggtt tccagctttta tccatgtccc tacaaaggac atgaactcaa     720
ccttgtttat ggctgcatag tattccatgg tgtatatgtg ccacattttc ttaacccagt     780
ctatcattga tggacatttg ggttggttcc aagtctttac tattgtgaat agtgccacaa     840
taaacataca tgtgcatgca tctttatagt agcatgattt ataatccttt gggtatatac     900
ctagtaatgg gatctttggg ttaaatggta tttctagttc tagatccttg aggaatcgcc     960
acactgtctt ccacaatggt tgagctagtt tacactccca ccgatggtgt aaaagcattc    1020
ctatttctcc acatcctctc cagcacctgt tgtttcctga cttttttaatt attgccattc    1080
taactactgt gagatgatat tcattgtggg ttttgatttg catttctctg atggccagtg    1140
atgatgagca ttttttcatg tgtctgctgg ctgcataaat ctcttctttt caaaagtgtc    1200
tgtccatatc ctttgcccac ttttttgatgg ggttgtttga tttttttcttg taaatttgtt   1260
taagttcttt gtagattctg gatattagcc ctttgtcaga tgggtagatt gcaaaaattt    1320
tctcccattc tgtaggctgc ctgttcactc tgatggtagt ttcttttgct gtgcagaagc    1380
tctttagttt aattagatcc catttgtcta ttttggcttt tgttgccatt gcttttggtg     1440
ttttagtcat gaagtacttg cccatgccta tgtcctgaat ggtattgccc aggttttctt    1500
ctagggtttt tatggtttta ggtctaacat ttaagtcttt aatctatctt gaattaattt    1560
ttgtataagg tgtaaggaag ggatccagtt tcagctttct acatatggct agccagtttt    1620
cccagcacca tttattaaat aaggaatcct ttccccattt cttgtttttg tcaggttttgt   1680
caaagatcag atggttgtag atgtgtgtg ttatttctga ggcctctgtt ctgttccatt     1740
ggtctatatc tgttttggca ccagtaccat gctgttttgg ttactgtaag ctggtagtat    1800
agtttgaagt caggtaatgt gatgcctcca gctttgttct ttttgcttag gattgtcttg    1860
gcaatgcagg ccctttttgtg gttccatatg aactttaaag tagttttttc cacttctgtg   1920
aagaaagtca ttggtagctt gatggggatg gcattgaatc tctaaattac cttgggcagt    1980
atggccattt tcacgatatt gattcttcct atccaagagc atggaatgtt cttccatttg    2040
tttgtgtcct cttatttcat tgagcagtgg tttgtggttc tcaggagggc tttttttaaa    2100
aaaggttctt taaggaaaaa tgtatctatt atttacagag attcaagtat ggactagcaa    2160
cagcaggaag tctgaagcag cgtgttgggg ggtgggggtg aataatgtca cctgacaaca    2220
agagatggcg ctctgaaaca gggaccagac agaagctgca gtcagagaga aacagccatt    2280
```

```
gccacaccat gctgcattaa gtatccgtgg ctgtaaaaat tattcaaaca tttggtggct    2340
tcacacatga tttcttatcc acagttgtta tggatcagca gtccaggtac agatgcgccc    2400
tcagacacag agtctctaat gaggctgcag tcaaggtatc atcgaggctg cggtcacctc    2460
aaaactcagc tgaggaaaga cccacttcca agctcagtca cgtggtagct ggcagggttg    2520
agttcctcac agatagctgg actaaggggcc tcggctcctt actggctaca ggctggaggc   2580
tgtcctcggt ttcttgccac gtaggtctct ccacaggaca gcctcacaca tggccactca    2640
cttcatcaga gcaagctgag aagatccaga gacagagtgt gtgtaaacaa gactaaagtc    2700
atagtctcag aactgactac ctcatcactt tgccatcttc tatttgttag gagtgaatct    2760
cgagacccag cccagttaag cagaggaaat tacagcaggg caccaatgcc aagacgtagg    2820
catcaccagg agctatctct gaagtcgtcc taccacacat gccaaagcaa gagagggagc    2880
aggaggaaca aatgccttga tctctcccctt ttcccaccct cccatctccc acctgtgtct   2940
cccattggcc aaactcaact cgaagctaga gggcatggga gcccaggtga tacagcccat    3000
agaggcatcc ttccagacca gtgcagagat gagagagaat aaacctgagg cagaggggag    3060
agaggtacaa cgagcagccc atgagacaag acacagatca gcgaactgac agtcatcatg    3120
gaggtcagat aacctagaaa acaagacatc acacagagca gcccctcacc catatccatg    3180
aggtccgtca agacattgca cagagcagcc tctcacccat atccatgagg tctgcctctt    3240
taatctatgc acccaattct ttcccaggct ctataatttg gggtaacatt tctctgggcc    3300
ctgttataga ataatgaaaa ttttctataa aacaaatgtc cttactttca cctcatccct    3360
atttatgtaa atgcttgcct ctttaattac tgaggccagg aggaagattt gggagaggaa    3420
agggctatgc ggtgacattt ggaaagaccc tgctctgtga cagttctagt gttgacgcca    3480
aagttctcat ttcctcttag aaaagtcttg tgcaaatagc ataatttgct cctgttgact    3540
tttttaatgt gctcatggag actgctcggg atctagatct gtttgggatc tgcaggactt    3600
ctccttctgc agtgtacaca cacgtgcaca cacgtatgtg cacatacca gggcactggt     3660
gccatcaaaa ctttctcttg ttcttcagcc ttccccattc caggtaaggc caccaccacc    3720
ttcaaggctc ccaggcccag accctcaggc aggtagcaat tgccaaggct ttaatgtccc    3780
accccattaa ttttatcttc ctttatctcc tgaaaagatt aatgttctaa accctggcac    3840
ccaaaacacc ctcatgttga aaactcttca ataccccctt ctcacactca tcttcagagc    3900
taccatgagg cagagaagcc tccggaatca gcccacatgg ggctgggtga atgccaacac    3960
caagcaaggg gaaagtcaca aattgacatc cagcaccta ttctccaccc ttcagcccct     4020
caactgactc ctgctccacg gcccgttcta ttaatatcta gcatttagca ccagcctgga    4080
caaaaaccta cttggaaaga tggtacaaga accccacaca actccataga acttcgctgt    4140
ctaaaaaaat gctttgccgt atattatccc acttaatctc caccactatg ctgtacatag    4200
gagccacaac tcctagacaa caaataaaaa tcctatcact tttcaaatcc taacattttc    4260
atatgacaaa gccagaactc aaaatccaga cctctagagt cccagatcag gaaaggaaga    4320
aacgccaagt caaagagaag cttctttaga ataatctgct tttctggatt attcacacca    4380
tgggtcagct ccccacttga agtcagaacc aagctccaat ttcagtgaac caccatcatg    4440
ctttgaccag gagattctct cagaaatgtg gggtcccatt gagtaggcct gaagacagag    4500
attgacaggc ctatgtgagc ctggaggagt tcttttagg ggctggataa tgtcaagaac     4560
agagaacaac tccagagaag gcacacacgc cttcaaaccc atcccctcat ggggagaaag    4620
```

```
cagccaggaa ctcaggcctc aagtgttcta ggtgtggtct cccaaggaaa cgggctcact      4680
tagtttgggg aaaccttcaa accctgcact gagtcctatg tagactggga cagaaggtgg      4740
acaatgtaat cccctgagcc ctcaacctcc tcctggagag atgacaagat taagatttct      4800
ctaccagaac cctcaacaga cacatcccag aatctcccca agtgaaatgt gctctaccta      4860
ccgtccctga gagcccaggg gtgtgaaccc agagggcagg tgtggtgggg aagggaggag      4920
ggagaaagaa aagggatggc tgggagttag agaaaggctc ctatccagga cctgcctgca      4980
aggatcccag gtatcagcca gcccaaccta gcccttgttg acttagcagg tgacagtttg      5040
gggaagaagg ggaggaggat gcggaagtca cacctctcca ggcttggttc ccattggccc      5100
ttgatatcct taaaagggcc cagcaatttc agcatcctta ttccccagac cttctgcaga      5160
ttctgtggtt atactcactc ctcatcccaa aga                                  5193
```

<210> SEQ ID NO 6
<211> LENGTH: 2436
<212> TYPE: DNA
<213> ORGANISM: Homo sapiens

<400> SEQUENCE: 6

```
tctcgagacc cagcccagtt aagcagagga aattacagca gggcaccaat gccaagacgt        60
aggcatcacc aggagctatc tctgaagtcg tcctaccaca catgccaaag caagagaggg       120
agcaggagga acaaatgcct tgatctctcc ctttcccac cctcccatct cccacctgtg        180
tctcccattg gccaaactca actcgaagct agagggcatg ggagcccagg tgatacagcc       240
catagaggca tccttccaga ccagtgcaga gatgagagag aataaacctg aggcagaggg       300
gagagaggta caacgagcag cccatgagac aagacacaga tcagcgaact gacagtcatc       360
atggaggtca gataacctag aaaacaagac atcacacaga gcagcccctc acccatatcc       420
atgaggtccg tcaagacatt gcacagagca gcctctcacc catatccatg aggtctgcct       480
ctttaatcta tgcacccaat tctttcccag gctctataat ttggggtaac atttctctgg       540
gccctgttat agaataatga aaattttcta taaaacaaat gtccttactt tcacctcatc       600
cctatttatg taaatgcttg cctctttaat tactgaggcc aggaggaaga tttgggagag       660
gaaagggcta tgcggtgaca tttggaaaga ccctgctctg tgacagttct agtgttgacg       720
ccaaagttct catttcctct tagaaaagtc ttgtgcaaat agcataattt gctcctgttg       780
acttttttaa tgtgctcatg gagactgctc gggatctaga tctgtttggg atctgcagga       840
cttctccttc tgcagtgtac acacacgtgc acacacgtat gtgcacatac ccagggcact       900
ggtgccatca aaactttctc ttgttcttca gccttcccca ttccaggtaa ggccaccacc       960
accttcaagg ctcccaggcc cagaccctca ggcaggtagc aattgccaag gctttaatgt      1020
cccaccccat taattttatc ttcctttatc tcctgaaaag attaatgttc taaaccctgg      1080
cacccaaaac accctcatgt tgaaaactct tcaataccccc cttctcacac tcatcttcag      1140
agctaccatg aggcagagaa gcctccggaa tcagcccaca tggggctggg tgaatgccaa      1200
caccaagcaa ggggaaagtc acaaattgac atccagcacc ttattctcca cccttcagcc      1260
cctcaactga ctcctgctcc acggcccgtt ctattaatat ctagcattta gcaccagcct      1320
ggacaaaaac ctacttggaa agatggtaca agaaccccac acaactccat gaacttcgc       1380 tgtctaaaaa aatgctttgc cgtatattat cccacttaat ctccaccact atgctgtaca      1440
taggagccac aactcctaga caacaaataa aaatcctatc acttttcaaa tcctaacatt      1500
ttcatatgac aaagccagaa ctcaaaatcc agacctctag agtcccagat caggaaagga      1560
```

-continued

```
agaaacgcca agtcaaagag aagcttcttt agaataatct gcttttctgg attattcaca   1620
ccatgggtca gctccccact tgaagtcaga accaagctcc aatttcagtg aaccaccatc   1680
atgctttgac caggagattc tctcagaaat gtgggtccc attgagtagg cctgaagaca    1740
gagattgaca ggcctatgtg agcctggagg agttcttttt aggggctgga taatgtcaag   1800
aacagagaac aactccagag aaggcacaca cgccttcaaa cccatcccct catggggaga   1860
aagcagccag gaactcaggc ctcaagtgtt ctaggtgtgg tctcccaagg aaacgggctc   1920
acttagtttg gggaaacctt caaaccctgc actgagtcct atgtagactg ggacagaagg   1980
tggacaatgt aatcccctga gccctcaacc tcctcctgga gagatgacaa gattaagatt   2040
tctctaccag aaccctcaac agacacatcc cagaatctcc ccaagtgaaa tgtgctctac   2100
ctaccgtccc tgagagccca ggggtgtgaa cccagagggc aggtgtggtg gggaagggag   2160
gagggagaaa gaaagggat ggctgggagt tagagaaagg ctcctatcca ggacctgcct    2220
gcaaggatcc caggtatcag ccagcccaac ctagcccttg ttgacttagc aggtgacagt   2280
ttggggaaga aggggaggag gatgcggaag tcacacctct ccaggcttgg ttcccattgg   2340
cccttgatat ccttaaaagg gcccagcaat ttcagcatcc ttattcccca gaccttctgc   2400
agattctgtg gttatactca ctcctcatcc caaaga                             2436
```

<210> SEQ ID NO 7
<211> LENGTH: 1620
<212> TYPE: DNA
<213> ORGANISM: Homo sapiens

<400> SEQUENCE: 7

```
tagatctgtt tgggatctgc aggacttctc cttctgcagt gtacacacac gtgcacacac     60
gtatgtgcac atacccaggg cactggtgcc atcaaaactt tctcttgttc ttcagccttc    120
cccattccag gtaaggccac caccaccttc aaggctccca ggcccagacc ctcaggcagg    180
tagcaattgc caaggcttta atgtcccacc ccattaattt tatcttcctt tatctcctga    240
aaagattaat gttctaaacc ctggcaccca aaacaccctc atgttgaaaa ctcttcaata    300
ccccttctc acactcatct tcagagctac catgaggcag agaagcctcc ggaatcagcc     360
cacatggggc tgggtgaatg ccaacaccaa gcaaggggaa agtcacaaat tgacatccag    420
cccttattc tccacccttc agcccctcaa ctgactcctg ctccacggcc cgttctatta     480
atatctagca tttagcacca gcctggacaa aaacctactt ggaaagatgg tacaagaacc    540
ccacacaact ccatagaact tcgctgtcta aaaaaatgct ttgccgtata ttatcccact    600
taatctccac cactatgctg tacataggag ccacaactcc tagacaacaa ataaaaatcc    660
tatcactttt caaatcctaa cattttcata tgacaaagcc agaactcaaa atccagacct    720
ctagagtccc agatcaggaa aggaagaaac gccaagtcaa agagaagctt ctttagaata    780
atctgctttt ctggattatt cacaccatgg gtcagctccc cacttgaagt cagaaccaag    840
ctccaatttc agtgaaccac catcatgctt tgaccaggag attctctcag aaatgtgggg    900
tcccattgag taggcctgaa gacagagatt gacaggccta tgtgagcctg gaggagttct    960
ttttagggc tggataatgt caagaacaga gaacaactcc agagaaggca cacgccctt    1020
caaacccatc ccctcatggg gagaaagcag ccaggaactc aggcctcaag tgttctaggt   1080
gtggtctccc aaggaaacgg gctcacttag ttggggaaa ccttcaaacc ctgcactgag   1140
tcctatgtag actgggacag aaggtggaca atgtaatccc ctgagccctc aacctcctcc   1200
```

-continued

```
tggagagatg acaagattaa gatttctcta ccagaaccct caacagacac atcccagaat    1260
ctccccaagt gaaatgtgct ctacctaccg tccctgagag cccaggggtg tgaacccaga    1320
gggcaggtgt ggtggggaag ggaggaggga gaaagaaaag ggatggctgg gagttagaga    1380
aaggctccta tccaggacct gcctgcaagg atcccaggta tcagccagcc caacctagcc    1440
cttgttgact tagcaggtga cagtttgggg aagaagggga ggaggatgcg gaagtcacac    1500
ctctccaggc ttggttccca ttggcccttg atatccttaa aagggcccag caatttcagc    1560
atccttattc cccagacctt ctgcagattc tgtggttata ctcactcctc atcccaaaga    1620
```

<210> SEQ ID NO 8
<211> LENGTH: 862
<212> TYPE: DNA
<213> ORGANISM: Homo sapiens

<400> SEQUENCE: 8

```
aaagagaagc ttctttagaa taatctgctt ttctggatta ttcacaccat gggtcagctc      60
cccacttgaa gtcagaacca agctccaatt tcagtgaacc accatcatgc tttgaccagg     120
agattctctc agaaatgtgg ggtcccattg agtaggcctg aagacagaga ttgacaggcc     180
tatgtgagcc tggaggagtt cttttaggg gctggataat gtcaagaaca gagaacaact     240
ccagagaagg cacacacgcc ttcaaaccca tccctcatg gggagaaagc agccaggaac     300
tcaggcctca agtgttctag gtgtggtctc ccaaggaaac gggctcactt agtttgggga     360
aaccttcaaa ccctgcactg agtcctatgt agactgggac agaaggtgga caatgtaatc     420
ccctgagccc tcaacctcct cctggagaga tgacaagatt aagatttctc taccagaacc     480
ctcaacagac acatcccaga atctccccaa gtgaaatgtg ctctacctac cgtccctgag     540
agcccagggg tgtgaaccca gagggcaggt gtggtgggga agggaggagg gagaaagaaa     600
agggatggct gggagttaga gaaaggctcc tatccaggac ctgcctgcaa ggatcccagg     660
tatcagccag cccaacctag cccttgttga cttagcaggt gacagtttgg ggaagaaggg     720
gaggaggatg cggaagtcac acctctccag gcttggttcc cattggccct tgatatcctt     780
aaaagggccc agcaatttca gcatccttat tccccagacc tttctgcagat tctgtggtta     840 tactcactcc tcatcccaaa ga                                              862
```

<210> SEQ ID NO 9
<211> LENGTH: 19
<212> TYPE: PRT
<213> ORGANISM: Homo sapiens

<400> SEQUENCE: 9

Met Lys Phe Thr Thr Leu Leu Phe Leu Ala Ala Val Ala Gly Ala Leu
1               5                   10                  15

Val Tyr Ala

<210> SEQ ID NO 10
<211> LENGTH: 119
<212> TYPE: PRT
<213> ORGANISM: Homo sapiens

<400> SEQUENCE: 10

Glu Asp Ala Ser Ser Asp Ser Thr Gly Ala Asp Pro Ala Gln Glu Ala
1               5                   10                  15

Gly Thr Ser Lys Pro Asn Glu Glu Ile Ser Gly Pro Ala Glu Pro Ala
            20                  25                  30

-continued

```
Ser Pro Pro Glu Thr Thr Thr Ala Gln Glu Thr Ser Ala Ala Ala
        35                  40                  45

Val Gln Gly Thr Ala Lys Val Thr Ser Ser Arg Gln Glu Leu Asn Pro
 50                  55                  60

Leu Lys Ser Ile Val Glu Lys Ser Ile Leu Leu Thr Gln Ala Leu
 65                  70                  75                  80

Ala Lys Ala Gly Lys Gly Met His Gly Val Pro Gly Gly Lys Gln
                85                  90                  95

Phe Ile Glu Asn Gly Ser Glu Phe Ala Gln Lys Leu Leu Lys Lys Phe
                    100                 105                 110

Ser Leu Leu Lys Pro Trp Ala
        115
```

```
<210> SEQ ID NO 11
<211> LENGTH: 23
<212> TYPE: DNA
<213> ORGANISM: Artificial
<220> FEATURE:
<223> OTHER INFORMATION: Oligonucleotide probe for detecting genomic
      lacritin clone
<220> FEATURE:
<221> NAME/KEY: primer_bind
<222> LOCATION: (1)..(23)

<400> SEQUENCE: 11
agctggggca caggcacccg cac                                              23

<210> SEQ ID NO 12
<211> LENGTH: 23
<212> TYPE: DNA
<213> ORGANISM: Artificial
<220> FEATURE:
<223> OTHER INFORMATION: Oligonucleotide probe for detecting genomic
      lacritin clone
<220> FEATURE:
<221> NAME/KEY: primer_bind
<222> LOCATION: (1)..(23)

<400> SEQUENCE: 12
ggggttctgg ggctgcagct ggg                                              23

<210> SEQ ID NO 13
<211> LENGTH: 21
<212> TYPE: DNA
<213> ORGANISM: Artificial
<220> FEATURE:
<223> OTHER INFORMATION: PCR primer corresponding to nucleotides 523 to
      503 of the lacritin gene
<220> FEATURE:
<221> NAME/KEY: primer_bind
<222> LOCATION: (1)..(21)

<400> SEQUENCE: 13
cgctacaagg gtatttaagg c                                                21

<210> SEQ ID NO 14
<211> LENGTH: 20
<212> TYPE: DNA
<213> ORGANISM: Artificial
<220> FEATURE:
<223> OTHER INFORMATION: PCR primer for exon 1 of the lacritin gene
<220> FEATURE:
<221> NAME/KEY: primer_bind
<222> LOCATION: (1)..(20)

<400> SEQUENCE: 14
```

```
actcactcct catcccaaag                                                   20
```

<210> SEQ ID NO 15
<211> LENGTH: 19
<212> TYPE: DNA
<213> ORGANISM: Artificial
<220> FEATURE:
<223> OTHER INFORMATION: PCR primer for exon 5 of the lacritin gene
<220> FEATURE:
<221> NAME/KEY: primer_bind
<222> LOCATION: (1)..(19)

<400> SEQUENCE: 15

```
ttttcagctt ctcatgccc                                                    19
```

<210> SEQ ID NO 16
<211> LENGTH: 114
<212> TYPE: PRT
<213> ORGANISM: homo sapiens

<400> SEQUENCE: 16

```
Asp Ser Thr Gly Ala Asp Pro Ala Gln Glu Ala Gly Thr Ser Lys Pro
1               5                   10                  15

Asn Glu Glu Ile Ser Gly Pro Ala Glu Pro Ala Ser Pro Pro Glu Thr
            20                  25                  30

Thr Thr Thr Ala Gln Glu Thr Ser Ala Ala Ala Val Gln Gly Thr Ala
        35                  40                  45

Lys Val Thr Ser Ser Arg Gln Glu Leu Asn Pro Leu Lys Ser Ile Val
50                  55                  60

Glu Lys Ser Ile Leu Leu Thr Glu Gln Ala Leu Ala Lys Ala Gly Lys
65                  70                  75                  80

Gly Met His Gly Gly Val Pro Gly Gly Lys Gln Phe Ile Glu Asn Gly
                85                  90                  95

Ser Glu Phe Ala Gln Lys Leu Leu Lys Lys Phe Ser Leu Leu Lys Pro
            100                 105                 110

Trp Ala
```

<210> SEQ ID NO 17
<211> LENGTH: 114
<212> TYPE: PRT
<213> ORGANISM: Homo sapiens

<400> SEQUENCE: 17

```
Glu Asp Ala Ser Ser Asp Ser Thr Gly Ala Asp Pro Ala Gln Glu Ala
1               5                   10                  15

Gly Thr Ser Lys Pro Asn Glu Glu Ile Ser Gly Pro Ala Glu Pro Ala
            20                  25                  30

Ser Pro Pro Glu Thr Thr Thr Thr Ala Gln Glu Thr Ser Ala Ala Ala
        35                  40                  45

Val Gln Gly Thr Ala Lys Val Thr Ser Ser Arg Gln Glu Leu Asn Pro
    50                  55                  60

Leu Lys Ser Ile Val Glu Lys Ser Ile Leu Leu Thr Glu Gln Ala Leu
65                  70                  75                  80

Ala Lys Ala Gly Lys Gly Met His Gly Gly Val Pro Gly Gly Lys Gln
                85                  90                  95

Phe Ile Glu Asn Gly Ser Glu Phe Ala Gln Lys Leu Leu Lys Lys Phe
            100                 105                 110

Ser Leu
```

```
<210> SEQ ID NO 18
<211> LENGTH: 109
<212> TYPE: PRT
<213> ORGANISM: homo sapiens

<400> SEQUENCE: 18

Glu Asp Ala Ser Ser Asp Ser Thr Gly Ala Asp Pro Ala Gln Glu Ala
1               5                   10                  15

Gly Thr Ser Lys Pro Asn Glu Glu Ile Ser Gly Pro Ala Glu Pro Ala
                20                  25                  30

Ser Pro Pro Glu Thr Thr Thr Thr Ala Gln Glu Thr Ser Ala Ala Ala
            35                  40                  45

Val Gln Gly Thr Ala Lys Val Thr Ser Ser Arg Gln Glu Leu Asn Pro
    50                  55                  60

Leu Lys Ser Ile Val Glu Lys Ser Ile Leu Leu Thr Glu Gln Ala Leu
65                  70                  75                  80

Ala Lys Ala Gly Lys Gly Met His Gly Gly Val Pro Gly Gly Lys Gln
                85                  90                  95

Phe Ile Glu Asn Gly Ser Glu Phe Ala Gln Lys Leu Leu
            100                 105

<210> SEQ ID NO 19
<211> LENGTH: 104
<212> TYPE: PRT
<213> ORGANISM: homo sapiens

<400> SEQUENCE: 19

Glu Asp Ala Ser Ser Asp Ser Thr Gly Ala Asp Pro Ala Gln Glu Ala
1               5                   10                  15

Gly Thr Ser Lys Pro Asn Glu Glu Ile Ser Gly Pro Ala Glu Pro Ala
                20                  25                  30

Ser Pro Pro Glu Thr Thr Thr Thr Ala Gln Glu Thr Ser Ala Ala Ala
            35                  40                  45

Val Gln Gly Thr Ala Lys Val Thr Ser Ser Arg Gln Glu Leu Asn Pro
    50                  55                  60

Leu Lys Ser Ile Val Glu Lys Ser Ile Leu Leu Thr Glu Gln Ala Leu
65                  70                  75                  80

Ala Lys Ala Gly Lys Gly Met His Gly Gly Val Pro Gly Gly Lys Gln
                85                  90                  95

Phe Ile Glu Asn Gly Ser Glu Phe
            100

<210> SEQ ID NO 20
<211> LENGTH: 99
<212> TYPE: PRT
<213> ORGANISM: homo sapiens

<400> SEQUENCE: 20

Glu Asp Ala Ser Ser Asp Ser Thr Gly Ala Asp Pro Ala Gln Glu Ala
1               5                   10                  15

Gly Thr Ser Lys Pro Asn Glu Glu Ile Ser Gly Pro Ala Glu Pro Ala
                20                  25                  30

Ser Pro Pro Glu Thr Thr Thr Thr Ala Gln Glu Thr Ser Ala Ala Ala
            35                  40                  45

Val Gln Gly Thr Ala Lys Val Thr Ser Ser Arg Gln Glu Leu Asn Pro
    50                  55                  60

Leu Lys Ser Ile Val Glu Lys Ser Ile Leu Leu Thr Glu Gln Ala Leu
```

```
              65                  70                  75                  80
Ala Lys Ala Gly Lys Gly Met His Gly Gly Val Pro Gly Gly Lys Gln
                    85                  90                  95

Phe Ile Glu

<210> SEQ ID NO 21
<211> LENGTH: 94
<212> TYPE: PRT
<213> ORGANISM: homo sapiens

<400> SEQUENCE: 21

Glu Asp Ala Ser Ser Asp Ser Thr Gly Ala Asp Pro Ala Gln Glu Ala
1               5                   10                  15

Gly Thr Ser Lys Pro Asn Glu Glu Ile Ser Gly Pro Ala Glu Pro Ala
                20                  25                  30

Ser Pro Pro Glu Thr Thr Thr Thr Ala Gln Glu Thr Ser Ala Ala Ala
            35                  40                  45

Val Gln Gly Thr Ala Lys Val Thr Ser Ser Arg Gln Glu Leu Asn Pro
        50                  55                  60

Leu Lys Ser Ile Val Glu Lys Ser Ile Leu Thr Gln Ala Leu
65                  70                  75                  80

Ala Lys Ala Gly Lys Gly Met His Gly Gly Val Pro Gly Gly
                85                  90

<210> SEQ ID NO 22
<211> LENGTH: 60
<212> TYPE: PRT
<213> ORGANISM: homo sapiens

<400> SEQUENCE: 22

Glu Asp Ala Ser Ser Asp Ser Thr Gly Ala Asp Pro Ala Gln Glu Ala
1               5                   10                  15

Gly Thr Ser Lys Pro Asn Glu Glu Ile Ser Gly Pro Ala Glu Pro Ala
                20                  25                  30

Ser Pro Pro Glu Thr Thr Thr Thr Ala Gln Glu Thr Ser Ala Ala Ala
            35                  40                  45

Val Gln Gly Thr Ala Lys Val Thr Ser Ser Arg Gln
        50                  55                  60

<210> SEQ ID NO 23
<211> LENGTH: 19
<212> TYPE: PRT
<213> ORGANISM: homo sapiens

<400> SEQUENCE: 23

Lys Gln Phe Ile Glu Asn Gly Ser Glu Phe Ala Gln Lys Leu Leu Lys
1               5                   10                  15

Lys Phe Ser

<210> SEQ ID NO 24
<211> LENGTH: 14
<212> TYPE: PRT
<213> ORGANISM: homo sapiens

<400> SEQUENCE: 24

Asn Gly Ser Glu Phe Ala Gln Lys Leu Leu Lys Lys Phe Ser
1               5                   10

<210> SEQ ID NO 25
```

```
<211> LENGTH: 21
<212> TYPE: DNA
<213> ORGANISM: homo sapiens

<400> SEQUENCE: 25
ggtggtcata tggaagatgc c                                                  21

<210> SEQ ID NO 26
<211> LENGTH: 27
<212> TYPE: DNA
<213> ORGANISM: homo sapiens

<400> SEQUENCE: 26
ggtggttgct cttccgcatg cccatgg                                            27

<210> SEQ ID NO 27
<211> LENGTH: 45
<212> TYPE: DNA
<213> ORGANISM: homo sapiens

<400> SEQUENCE: 27
ggtggttgct cttccaacta ttattactat gaagatgcct cctct                        45

<210> SEQ ID NO 28
<211> LENGTH: 26
<212> TYPE: DNA
<213> ORGANISM: homo sapiens

<400> SEQUENCE: 28
ggtggtgaat tctcatagac tgaatt                                             26

<210> SEQ ID NO 29
<211> LENGTH: 27
<212> TYPE: DNA
<213> ORGANISM: homo sapiens

<400> SEQUENCE: 29
ggtggtgaat tctcacagta attttg                                             27

<210> SEQ ID NO 30
<211> LENGTH: 27
<212> TYPE: DNA
<213> ORGANISM: homo sapiens

<400> SEQUENCE: 30
ggtggtgaat tctcaaaatt cacttcc                                            27

<210> SEQ ID NO 31
<211> LENGTH: 27
<212> TYPE: DNA
<213> ORGANISM: homo sapiens

<400> SEQUENCE: 31
ggtggtgaat tctcattcga tgaattc                                            27

<210> SEQ ID NO 32
<211> LENGTH: 26
<212> TYPE: DNA
<213> ORGANISM: homo sapiens

<400> SEQUENCE: 32
ggtggtgaat tctcattcac ctggca                                             26
```

```
<210> SEQ ID NO 33
<211> LENGTH: 26
<212> TYPE: DNA
<213> ORGANISM: homo sapiens

<400> SEQUENCE: 33
ggtggtgaat tctcactgcc tgcttg                                          26

<210> SEQ ID NO 34
<211> LENGTH: 37
<212> TYPE: DNA
<213> ORGANISM: homo sapiens

<400> SEQUENCE: 34
ggtggttgct cttccaacat ctcaggtcca gcagaac                              37

<210> SEQ ID NO 35
<211> LENGTH: 27
<212> TYPE: DNA
<213> ORGANISM: homo sapiens

<400> SEQUENCE: 35
ggtggttgct cttccgcatg cccatgg                                         27

<210> SEQ ID NO 36
<211> LENGTH: 6
<212> TYPE: PRT
<213> ORGANISM: homo sapiens

<400> SEQUENCE: 36

Val Gly Val Leu Ala Val
1               5

<210> SEQ ID NO 37
<211> LENGTH: 6
<212> TYPE: PRT
<213> ORGANISM: homo sapiens

<400> SEQUENCE: 37

Leu Ala Phe Gly Leu Phe
1               5
```

USE OF LACRITIN IN PROMOTING OCULAR CELL SURVIVAL

CROSS REFERENCE TO RELATED APPLICATIONS

This application is a national stage filing of International Application No. PCT/US2005/016112 filed on May 6, 2005 which is entitled to priority pursuant to 35 U.S.C. §119(e) to U.S. provisional patent application No. 60/570,865, filed on May 13, 2004, the disclosures of which are hereby incorporated by reference herein in their entirety.

US GOVERNMENT RIGHTS

This invention was made with United States Government support under Grant No. R01 EY13143, awarded by National Institutes of Health. The United States Government may have certain rights in the invention.

BACKGROUND

Health of the ocular surface is dependent on tear fluid secretions from the lacrimal gland. The lacrimal acinar cells comprising the lacrimal gland are polarized and highly differentiated tear secreting cells that adhere to a complex periacinar basement membrane. The bulk of the apical cell cytoplasm contains large secretory granules packed with tear proteins. Known tear proteins include: lysozyme, which plays a prominent bactericidal role on the corneal surface; lactoferrin, which functions as both a bactericidal agent and as a potential inhibitor of complement activation; secretory component, which regulates the transcellular movement of IgA into acini lumen where it acts on the corneal surface to inhibit bacterial adhesion; and tear lipocalins (tear-specific prealbumin) and growth factors TGFα, TGFβ and EGF the functions of which are not known. In rats, peroxidase is a tear component which has served as a convenient marker in experimental studies. Tears not only have an important bactericidal role, they also keep the cornea clean and lubricated and are important for the well-being of the corneal epithelium.

The surface of the eye is one of the most accessible and vulnerable tissues. Corneal epithelial cells confront environmental insults constantly including: UV irradiation, widely varying air temperature fluxes, pollutants, bacteria and other microbial organisms. The tear fluid which bathes the corneal surface is the most likely source of cytoprotective and anti-inflammatory agents since the cornea lacks blood supply, unlike other tissues where blood vessels supply such agents. Indeed, tear fluid is rich in bactericidal proteins. Dry Eye patients suffering insufficient tear production are subject to corneal ulceration, infection or inflammation. Similar symptoms can be generated by extended contact lens use, since volume of tear supply is limited.

When lacrimal acinar cell tear output is collectively deficient, 'Dry Eye' (also known as keratoconjunctivitis sicca [KCS]), is the result. Dry Eye is a common ocular manifestation of Sjogren's syndrome, an autoimmune disease with unknown etiology that affects millions of people worldwide. Most commonly affected are post-menopausal women with varying degrees of severity. If untreated, Dry Eye can lead to corneal abrasion, ulceration, bacterial infection and loss of vision.

Molecular mechanisms underlying the pathogenic decline of secretory output by the main lacrimal gland are potentially multiple. Lacrimal glands of Sjogren's syndrome patients contain foci of B and T lymphocytes whose pathogenic expansion, possibly due to viral insult, can destroy lacrimal acini. However, acinar volume loss often appears insufficient relative to the theoretical overcapacity of the main lacrimal gland. Estimates suggest a potential secretory output up to ten-fold greater than is required to maintain a normal aqueous tear film layer. Other mechanisms therefore warrant attention, such as aberrant secretion of one or several common cytokines that may directly or indirectly alter lacrimal acinar cell function and/or lead to a decline in neural innervation. Novel autocrine/paracrine factor(s) released by lacrimal acinar cells into the tear film may be required for the health of the lacrimal secretory machinery, ductal system and corneal epithelium. The periacinar basement membrane is also required for normal secretory function, in part via 'BM180' whose apparent synergy with laminin-1 promotes stimulated tear secretion. Alteration of each of these factors, together or independent of hormonal changes, could contribute to decreased secretory capacity.

The lacrimal-corneal axis is a fundamental regulator of ocular health and plays a key role in ocular surface inflammation associated with Dry Eye Syndromes and corneal injury. A host of mediators are implicated in the development and progression of corneal inflammation, such as the proinflammatory cytokines TNF-α, IL-1β, IL-6 and the chemokine IL-8. Also involved are the arachidonic acid-derived eicosanoids which are produced by the activity of cyclooxygenases (primarily PGE2), lipooxygenases (12 (s)-HETE) and cytochrome P450 (12 (r)-HETE). Recent studies on lacritin mechanisms of action indicate converging PKCα and NFkB signaling pathways suggesting that lacritin may have a key anti-inflammatory role on the ocular surface. Recent clinical studies support this hypothesis. Comparison of tear proteins from 19 patients suffering from Blepharitis (inflammation of the lid) vs 27 healthy volunteers revealed lacritin to be decreased by 56% in patients.

Regulation of Slowly Renewing Epithelia

Epithelial renewal underpins organogenesis, homeostasis, and tumorigenesis in a growth and adhesion factor-modulated manner. Proliferation of slowly cycling populations of stationary, often sequestered, stem cells and their migratory 'transit amplifying' cellular offspring is dependent on compartmentalized extracellular cues that include β1 integrin adhesivity (Alonso, L., et al., Genes Dev., 2003, 17:1189-200) to basement membrane laminin (Li, S., et al., Dev. Cell, 2003, 4:613-624), and involvement of the Wnt family of mitogens, which display a particular proclivity towards renewing cell compartments (Pinto, D., et al., Genes Dev., 2003, 17:1709-1713; Kuhnert, F., et al., Proc. Natl. Acad. Sci. USA, 2004, 101:266-271).

In small intestine, Wnts secreted by crypt mesenchyme and epithelia act in a paracrine or autocrine manner to generate a proliferative zone seeded by a single stem cell in each crypt. Crypts are spatially separated but contiguous with outward protruding villi in which cessation of Wnt secretion terminates cell cycle progression and promotes hedgehog-dependent differentiation of the absorptive epithelial, enteroendocrine or goblet cells necessary for intestinal function. In skin, stem cells reside in the hair follicle bulge where continuous FGF-18 and BMP-6 proliferative suppression is thought to balance with positive proliferative pressure by Wnt signaling until disruptive skin injury requires replenishment of proliferative cells at the base of the epidermis. The equivalent unit of epithelial renewal in skin comprises one hair follicle and adjacent epidermis. Similar principles may be in play on the surface of the eye since Wnt signaling promotes corneal epithelial proliferation in response to injury. Corneal stem cells encircle the periphery of the cornea to contribute progeny, which migrate centrally as the proliferative basal layer of the stratified corneal epithelium. The stem cell niche is thus a key characteristic of rapidly renewing epithelia.

How turnover is regulated in non-rapidly renewing or persistent epithelia is more challenging to address, because a discrete stem cell niche appears to be absent. Epithelia displaying slow turnover under normal conditions comprise most adult organs of the body, including exocrine and endocrine glands, kidney, and liver. The recently discovered human protein 'lacritin' may offer new insights. Lacritin is secreted by acinar cells in adult lacrimal gland and a subpopulation of ductal cells in salivary glands; and has been detected by non-histological methods in thyroid and mammary glands, but not elsewhere.

Lacrimal, salivary, and mammary glands are exocrine glands in which long ductal ingrowths carry protein products from secretory acini to the outside. In salivary glands, the highly proliferative intercalated ductal cell acts like a stem cell or transit amplifying cell to populate upstream acinar and downstream ductal cell types. Importantly, all epithelial cell types also appear to be slowly cycling (Man, Y. G., et al., Anat. Rec., 2001, 263:202-214), much like adult mammary gland in which stem cells are located throughout the epithelium in different early stages of differentiation. The lacrimal gland has not been similarly examined, but slow proliferative capacity throughout the epithelium appears to be a common property of exocrine glands and other non-rapid renewing epithelia.

Many epithelial cells contact lacritin as it flows downstream from acini or ducts, a simple distribution mechanism whose intermittent quality could play a large role in regulating the slow renewal of this exocrine glandular epithelium. Also potentially influenced are the rapidly renewing epithelial cells on the surface of the eye and mouth where lacritin is deposited. Supporting this hypothesis are in vitro studies showing recombinant lacritin to be capable of promoting lacrimal acinar cell secretion, human salivary ductal cell proliferation, and calcium mobilization by human corneal epithelial cells (Sanghi, S., et al., J. Mol. Biol., 2001, 310:127-139). Thus in the absence of a particular stem cell niche, release of lacritin defines an intermittent proliferative field that spreads through the non-rapidly renewing epithelia of lacrimal and salivary glands. Since other non-rapidly renewing epithelia have luminal structures, proliferative fields may be a general principle of non-rapidly renewing or persistent epithelia.

There is a long felt need in the art for a method to promote survival of ocular epithelial cells, to prevent and treat ocular inflammation, and to enhance corneal repair following injury or surgical treatment. The present invention satisfies these needs.

SUMMARY OF THE INVENTION

The present invention is directed to the use of lacritin to promote ocular cell survival, and more particularly to promote ocular cell survival in the presence of an environmental insult. The invention is also directed to the use of lacritin to prevent and treat corneal infections and inflammation. The invention is further directed to the use of lacritin to promote corneal wound repair following environmental insult or surgical procedures of the cornea. The invention is also directed to the use of lacritin as a mitogen for only specific epithelial cells.

In one embodiment of the present invention, lacritin is included as an active agent in artificial tear products.

In one aspect, the invention encompasses a composition for treating or preventing an ocular surface associated disease, disorder, or condition. In one aspect, the invention encompasses a composition for treating or preventing an ocular surface associated infection, said composition comprising a therapeutically effective amount of a purified polypeptide comprising the amino acid sequence of SEQ ID NO: 4, or a fragment, or homolog thereof, a pharmaceutically acceptable carrier, and a purified antimicrobial agent. In one aspect, the fragment is SEQ ID NO:10.

In one aspect, the invention encompasses a composition wherein the anti-microbial agent is selected from the group consisting of benzalkonium chloride, benzethonium chloride, benzyl alcohol, chlorobutanol, chlorhexidine digluconate or diacetate, methyl and propyl hydroxybenzoate (parabens), phenylethyl alcohol, phenylmercuric acetate or nitrate, sorbic acid, and thimerosal.

In another embodiment, the invention encompasses a composition for treating or preventing an ocular infection, said composition comprising a therapeutically effective amount of an isolated nucleic acid encoding a polypeptide comprising the amino acid sequence of SEQ ID NO: 4, or a fragment, or homolog thereof, a pharmaceutically acceptable carrier, and a purified antimicrobial agent.

In one aspect, the composition comprises a topical ophthalmic formulation. In another aspect, the composition further comprises a pharmaceutically acceptable phospholipid or oil.

In one embodiment, the invention relates to a method of enhancing the survivability of human corneal epithelial cells or lacrimal acinar cells, said method comprising the step of contacting said cells with a composition comprising a polypeptide, wherein the polypeptide comprises the amino acid sequence of SEQ ID NO: 4, or a fragment, derivative, or homolog thereof. In one aspect, the amino acid sequence of the peptide is an amino acid sequence that differs from SEQ ID NO: 4 by one or more conservative amino acid substitutions; or an amino acid sequence that differs from SEQ ID NO: 4 by a single mutation, wherein the single mutation represents a single amino acid deletion, insertion or substitution. In one aspect, the fragments are selected from the group consisting of SEQ ID NOs:10, 16, 17, 18, and 19, and derivatives and fragments thereof.

In another embodiment, the invention provides a method of prolonging corneal epithelial cell or lacrimal acinar cell survival after exposure of the ocular surface of an eye to an environmental insult or injury, said method comprising the step of contacting the ocular surface with a composition comprising a polypeptide, wherein the polypeptide comprises the amino acid sequence of SEQ ID NO: 4, or a fragment, derivative, or homolog thereof. In one aspect, the polypeptide comprises an amino acid sequence that differs from SEQ ID NO: 4 by one or more conservative amino acid substitutions; or an amino acid sequence that differs from SEQ ID NO: 4 by a single mutation, wherein the single mutation represents a single amino acid deletion, insertion or substitution. In one aspect, the fragments are selected from the group consisting of SEQ ID NOs:10, 16, 17, 18, and 19, and derivatives and fragments thereof. In one aspect, the environmental insult comprises a bacterial or vial infection. In yet another aspect, the environmental insult comprises inflammation induced by a foreign object. In one aspect, the inflammation is induced by a contact lens. In yet another aspect, the inflammation is induced by a lack of sufficient tear production.

Lacritin is a selective mitogen for only certain epithelial cells. In one embodiment, the invention provides a method of inducing proliferation of epithelial which are sensitive to induction of proliferation by lacritin and fragments, derivatives, and homologs thereof.

In another embodiment, the invention provides a method of treating or preventing ocular-associated diseases, disorders, or conditions in a subject in need thereof. In one aspect, the ocular surface is treated. In another aspect, the cornea is treated. In one aspect, the subject is treated with a composition comprising a polypeptide, wherein the peptide comprises the sequence of native lacritin (SEQ ID NO:4), or fragments, derivative, or homologs thereof. In another aspect, the subject is treated with a composition comprising an isolated nucleic acid comprising a nucleic acid sequence encoding SEQ ID NO:4, or a fragment, derivative, or homolog thereof. In one aspect, the fragments are selected from the group consisting of SEQ ID NOs:10, 16, 17, 18, and 19, and derivatives and fragments thereof.

In one aspect, the ocular-associated diseases, disorders, or conditions which are treated by an isolated peptide of the invention, or an isolated nucleic acid encoding a peptide of the invention, include, but are not limited to, Dry Eye, conjunctivitis, Sjogren's syndrome, corneal abrasion, ulceration, bacterial infection, direct trauma, surgery, radiant energy, ionizing energy, viral infection, fungal infection, parasitic infection, keratitis, systemic dermatologic disorders, collagen vascular diseases, Reiter's disease, and Behcet's disease. In another aspect, additional drugs or agents appropriate for the particular disease, condition, or disorder may be administered as part of the composition.

The invention further provides a kit for administering the compositions of the invention.

Various aspects and embodiments of the invention are described in further detail below.

BRIEF DESCRIPTION OF THE DRAWINGS

FIG. 2A is a graphic representation of the number of human salivary gland (HSG) cells was determined four days after administering various amounts of lacritin (0 to 10 ng/ml of lacritin) to HSG cells in serum-free medium. FIG. 2B is a bar graph representing the proliferation of HSG cells upon administration of BSA (lane 1; 10 ng/ml) or serum (lane 2; 10%) was added for the same period of time. All experiments were performed on laminin-1-(0.05 µM) coated wells.

FIG. 3A is a bar graph of the resulting data plotting the number of cells entering apoptosis (the sub G0/G1 population) vs. time. After 24 hrs, cells without lacritin show very large DNA fragmentation or apoptosis. FIGS. 3B and 3C are graphic representations of flow cytometry readings showing that significant DNA fragmentation occurs in the cells cultured in the absence of lacritin (a sub G0/G1 population is indicated as a left shoulder of the large peak of FIG. 3B) but not present in FIG. 3C).

FIG. 5, comprising FIGS. 5A, B, C, and D, depicts the cell target specificity of mitogenic lacritin. FIG. 5A schematically illustrates Lacritin released from lacrimal acinar cell secretory granules flows via ducts to the surface of the eye. In salivary gland, lacritin is generated by ductal cells and flows into saliva. Inset, mature recombinant lacritin purified from *E. coli*. FIG. 5B, comprising 3 panels, illustrates graphically the results of a $^3$H-thymidine uptake assay demonstrating that Lacritin targeting of human ductal cells promotes a bell-shaped mitogenic response with maximum proliferative activity at 1 or 10 nM lacritin (left panel), equivalent to that of the 10% FBS positive control (middle panel). As seen in the right panel of FIG. 5B, lacritin also targets downstream human corneal epithelial cells (HCE), and to a lesser extent embryonic HEK293 cells. Cell types not responsive include: A431 (human epidermal), HeLa (human cervical), HS68 (human foreskin fibroblasts), HT1080 (human fibrosarcoma), K562 (human erythroleukemia), MCF7 (breast epithelial), NIH3T3 (mouse fibroblasts), SKMEL (human melanoma), TM3 (mouse Leydig), TM4 (mouse Sertoli), and WM164 (human melanoma) cells. FIG. 5C represents an image of an electrophoretic analysis of tyrosine phosphorylation, before, and one minute after lacritin addition. Accompanying densitometric scans follow tyrosine phosphorylation over four hours. FIG. 5D depicts an analysis of P42/p44 activation, indicating that they are not activated by lacritin. All experiments performed in human ductal cells in this and subsequent figures.

FIG. 6—FIG. 6, comprising FIGS. 6A to 6E, demonstrates that lacritin's C-terminal alpha helix is necessary for mitogenesis.

FIG. 7, comprising FIGS. 7A-D, demonstrates that lacritin's mitogenic C-terminus promotes calcium mobilization in a pertussis toxin inhibitable manner that requires PLC and PKCα.

FIG. 9, comprising FIGS. 9A and 9B, demonstrates that lacritin stimulated PKCα translocation is upstream of intracellular calcium release and is required for NFATC1 translocation and mitogenesis.

DETAILED DESCRIPTION OF THE INVENTION

Figure 1:
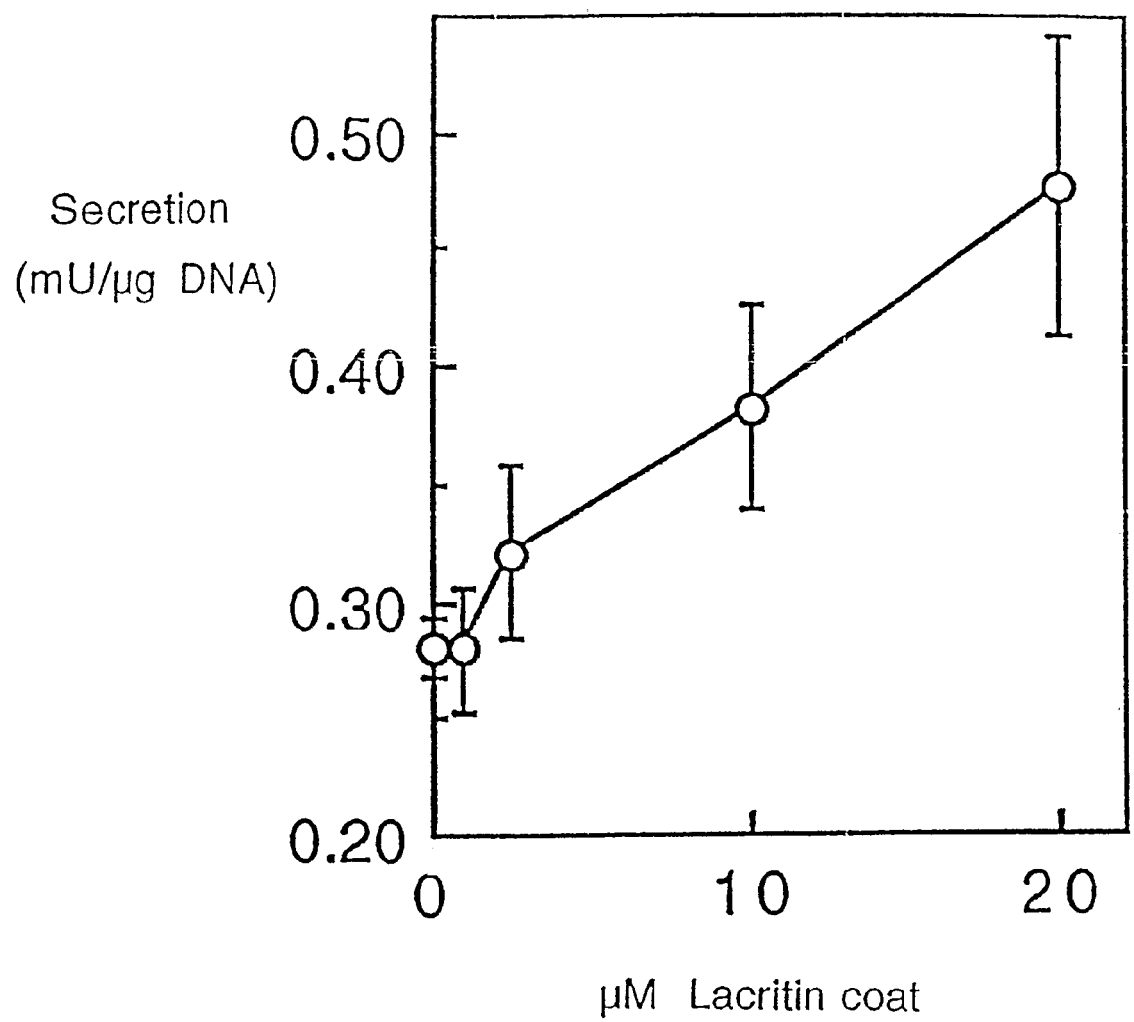
FIG. 1 is a graphic representation that shows recombinant lacritin enhances unstimulated secretion by isolated rat lacrimal acinar cells. Enhancement of unstimulated secretion was observed in the presence of increasing amounts of lacritin on lacritin-coated wells.

Abbreviations and Acronyms
HSG means human salivary gland
FACS means fluorescence activated cell sorter
HCE means human corneal epithelial
IRB means institutional review board
Definitions In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

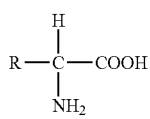

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)2, as well as single chain antibodies and humanized antibodies.

"Antimicrobial agent," as used herein, refers to any compound which impedes the growth of any microbes, or kills such microbes.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence polarization or altered light scattering.

An "enhancer" is a DNA regulatory element that can increase the efficiency of transcription, regardless of the distance or orientation of the enhancer relative to the start site of transcription.

As used herein, the phrase "enhancing survival" refers to decreasing the amount of death, or the rate of death, in a cell population. Enhancing survival can be due to preventing cell death alone (e.g., cell death in conjunction with apoptosis), or decreasing the rate of cell death. The decrease in cell death can also result from indirect effects such as inducing proliferation of some cells, such indirect effect effectively replenishing at least some or all of a population of cells as they die. Enhancing survival of cells can also be accomplished by a combination of inducing proliferation and decreasing cell death, or the rate of cell death. "Promoting survival" and "enhancing survivability" are used interchangeably with "enhancing survival" herein.

A "fragment" or "segment" is a portion of an amino acid sequence, comprising at least one amino acid, or a portion of a nucleic acid sequence comprising at least one nucleotide. The terms "fragment" and "segment" are used interchangeably herein. A fragment of a lacritin peptide which is used herein as part of a composition for use in a treatment or to elicit a lacritin effect, is presumed to be a biologically active fragment for the response to be elicited.

As used herein, a "functional" biological molecule is a biological molecule in a form in which it exhibits a property or activity by which it is characterized. A functional enzyme, for example, is one which exhibits the characteristic catalytic activity by which the enzyme is characterized.

As used herein, a "gene" refers to the nucleic acid coding sequence as well as the regulatory elements necessary for the DNA sequence to be transcribed into messenger RNA (mRNA) and then translated into a sequence of amino acids characteristic of a specific polypeptide.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "insult" refers to contact with a substance or environmental change that results in an alteration of normal cellular metabolism in a cell or population of cells. Environmental insults may include, but are not limited to, chemicals, environmental pollutants, heavy metals, viral or bacterial infections, changes in temperature, changes in pH, as well as agents producing oxidative damage, DNA damage, or pathogenesis. The term "insult" is used interchangeably with "environmental insult" herein.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "lacritin polypeptide" and like terms refers to peptides comprising the amino acid sequence of SEQ ID NO: 4 and biologically active fragments, derivatives, and homologs thereof. As used herein, the term "biologically active fragments" or "bioactive fragment" of a lacritin polypeptide encompasses natural or synthetic portions of the amino acid sequence

```
                                              (SEQ ID NO:4)
MKFTTLLFLAAVAGALVYAEDASSDSTGADPAQEAGTSKPNEEISGPAEP

ASPPETTTTAQETSAAAVQGTAKVTSSRQELNPLKSIVEKSILLTEQALA

KAGKGMHGGVPGGKQFIENGSEFAQKLLKKFSLLKPWA.
```

As used herein, a "ligand" is a compound that specifically binds to a target compound. A ligand (e.g., an antibody) "specifically binds to" or "is specifically immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow and Lane, 1988, Antibodies, A Laboratory Manual, Cold Spring Harbor Publications, New York, for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

"Ocular surface," as used herein, refers to the surface of the eye, particularly the corneal surface.

The phrase "ocular surface-associated disease, disorder, or condition," as used herein, refers to any disease, disorder or condition which directly or indirectly causes, or can cause, any of the problems or symptoms described herein regarding disease, disorders, or conditions of the ocular surface.

"Operably linked" refers to a juxtaposition wherein the components are configured so as to perform their usual function. Thus, control sequences or promoters operably linked to a coding sequence are capable of effecting the expression of the coding sequence.

A "marker" is an atom or molecule that permits the specific detection of a molecule comprising that marker in the presence of similar molecules without such a marker. Markers include, for example radioactive isotopes, antigenic determinants, nucleic acids available for hybridization, chromophors, fluorophors, chemiluminescent molecules, electrochemically detectable molecules, molecules that provide for altered fluorescence-polarization or altered light-scattering and molecules that allow for enhanced survival of an cell or organism (i.e. a selectable marker). A reporter gene is a gene that encodes for a marker.

A "polylinker" is a nucleic acid sequence that comprises a series of three or more different restriction endonuclease recognitions sequences closely spaced to one another (i.e. less than 10 nucleotides between each site).

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O) NR— linkages (bonds) have been replaced by a non-peptidyl linkage such as a —CH2-carbamate linkage (—CH2OC(O) NR—), a phosphonate linkage, a —CH2-sulfonamide (—CH 2-S(O)2NR—) linkage, a urea (—NHC(O)NH—) linkage, a—CH2-secondary amine linkage, or with an alkylated peptidyl linkage (—C(O)NR—) wherein R is C1-C4 alkyl;

2. peptides wherein the N-terminus is derivatized to a —NRR1 group, to a —NRC(O)R group, to a —NRC(O)OR group, to a —NRS(O)2R group, to a —NHC(O)NHR group where R and R1 are hydrogen or C1-C4 alkyl with the proviso that R and R1 are not both hydrogen;

3. peptides wherein the C terminus is derivatized to —C(O) R2 where R 2 is selected from the group consisting of C1-C4 alkoxy, and —NR3R4 where R3 and R4 are independently selected from the group consisting of hydrogen and C1-C4 alkyl.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, genetically encoded amino acids at one, two, or more positions of the peptides. For instance, naphthylalanine can be substituted for tryptophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A "promoter" is a DNA sequence that directs the transcription of a DNA sequence, such as the nucleic acid coding sequence of a gene. Typically, a promoter is located in the 5' region of a gene, proximal to the transcriptional start site of a structural gene. Promoters can be inducible (the rate of transcription changes in response to a specific agent), tissue specific (expressed only in some tissues), temporal specific (expressed only at certain times) or constitutive (expressed in all tissues and at a constant rate of transcription).

A "core promoter" contains essential nucleotide sequences for promoter function, including the TATA box and start of transcription. By this definition, a core promoter may or may not have detectable activity in the absence of specific sequences that enhance the activity or confer tissue specific activity.

As used herein, the term "purified" and like terms relate to the isolation of a molecule or compound in a form that is substantially free of contaminants normally associated with the molecule or compound in a native or natural environment. The term "purified" does not necessarily indicate that complete purity of the particular molecule has been achieved during the process. A "highly purified" compound as used herein refers to a compound that is greater than 90% pure.

As used herein, SEQ ID NO:1 refers to the nucleic acid sequence of the genomic gene of human lacritin, corresponding to the cDNA of lacritin identified as SEQ ID NO:2 herein.

As used herein, SEQ ID NO:2 refers to the nucleic acid sequence of a cDNA cloned from a human lacrimal gland library.

As used herein, SEQ ID NO:4 refers to the 138 amino acid sequence of the native human lacritin protein encoded by the nucleic acid sequence SEQ ID NO:2. SEQ ID NO:4 is also referred to as native lacritin.

As used herein, SEQ ID NO:10 refers to the 119 carboxy terminal amino acid residue mature fragment of SEQ ID NO:4 (native lacritin). SEQ ID NO:10 is also referred to herein as mature lacritin.

As used herein, SEQ ID NO:16, refers to the deletion mutant comprising a deletion of the 24 amino terminal amino acids of native lacritin (SEQ ID NO:4). SEQ ID NO:16 is also referred to as N-24.

As used herein, SEQ ID NO:17 refers to the deletion mutant comprising a deletion of the 5 carboxy terminal amino acids of mature lacritin (SEQ ID NO:10). SEQ ID NO:16 is also referred to as C-5.

As used herein, SEQ ID NO:18 refers to the deletion mutant comprising a deletion of the 10 carboxy terminal amino acids of mature lacritin (SEQ ID NO:10). SEQ ID NO:18 is also referred to as C-10.

As used herein, SEQ ID NO:19 refers to the deletion mutant comprising a deletion of the 15 carboxy terminal amino acids of mature lacritin (SEQ ID NO:10). SEQ ID NO:19 is also referred to as C-15.

As used herein, SEQ ID NO:20 refers to the deletion mutant comprising a deletion of the 20 carboxy terminal amino acids of mature lacritin (SEQ ID NO:10). SEQ ID NO:20 is also referred to as C-20.

As used herein, SEQ ID NO:21 refers to the deletion mutant comprising a deletion of the 25 carboxy terminal amino acids of mature lacritin (SEQ ID NO:10). SEQ ID NO:21 is also referred to as C-25.

As used herein, SEQ ID NO:22 refers to the deletion mutant comprising a deletion of the 59 carboxy terminal amino acids of mature lacritin (SEQ ID NO:10). SEQ ID NO:22 is also referred to as C-59.

A "subject" of experimentation, diagnosis or treatment is an animal, including a human.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

A "substantially pure nucleic acid", as used herein, refers to a nucleic acid sequence, segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "treating" includes prophylaxis of the specific disorder or condition, or alleviation of the symptoms associated with a specific disorder or condition and/or preventing or eliminating said symptoms. A "prophylacetic" treatment is a treatment administered to a subject who does not exhibit signs of a disease or exhibits only early signs of the disease for the purpose of decreasing the risk of developing pathology associated with the disease. As used herein, the term "treating" includes alleviating the symptoms associated with a specific disease, disorder or condition and/or preventing or eliminating said symptoms.

A "vector" is also meant to include a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, plasmids, cosmids, lambda phage vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, the term "wound" relates to a physical tear or rupture to a tissue or cell layer. A wound may occur by any physical insult, including a surgical procedure.

EMBODIMENTS OF THE INVENTION

The present invention is directed to uses of a human growth factor-like molecule, "lacritin," and compositions comprising lacritin, or fragments, derivatives, or homologs thereof. The invention also encompasses use of nucleic acid sequences encoding lacritin, as well as the nucleic acid regulatory elements controlling the expression of lacritin. The full length 'lacritin' cDNA has been cloned from a human lacrimal gland library (SEQ ID NO:2), and the corresponding genomic gene (SEQ ID NO: 1) has been cloned and sequenced, including 5.2 kb of upstream and 2.8 kb of downstream genomic sequence.

In one embodiment, the present invention is directed to use of a purified polypeptide comprising the amino acid sequence of SEQ ID NO: 4, SEQ ID NO: 10, a bioactive fragment of SEQ ID NO: 4, or an amino acid sequence that differs from SEQ ID NO: 4 by one or more conservative amino acid substitutions. More preferably, the purified polypeptide comprises an amino acid sequence that differs from SEQ ID NO: 4 by 20 or less conservative amino acid substitutions, and more preferably by 10 or less conservative amino acid substitutions. Alternatively, the polypeptide may comprise an amino acid sequence that differs from SEQ ID NO: 4 by 1 to 5 alterations, wherein the alterations are independently selected from a single amino acid deletion, insertion, or substitution. In one preferred embodiment a composition is provided comprising a polypeptide, selected from the group consisting of SEQ ID NO: 4, or SEQ ID NO: 10, and a pharmaceutically acceptable carrier. In another preferred embodiment, the fragments are fragments of SEQ ID NO: 10 (the mature processed lacritin) selected from the group of fragments with up to 25 amino acids deleted from the C-terminus. In another embodiment, up to 25 amino acids are deleted from the N-terminus of SEQ ID NO:4, the full length lacritin.

Physiological experiments recently performed using recombinant lacritin generated by E. coli suggests that lacritin is a survival factor, i.e., longevity in cell culture was promoted by the addition of physiological amounts of lacritin. Accordingly, in one embodiment of the present invention lacritin is administered topically to the eye of an individual as a survival factor to enhance the longevity of ocular cells and tissues in general, and more particularly in the presence of an environmental insult. Although lacritin has been previously described as promoting cell proliferation, and thus has utility for promoting corneal wound healing, the use of lacritin for promoting cell survival is surprising and an important and distinct function of lacritin. Viable and healthy cells are not necessarily proliferative and proliferation is often restricted to certain cell compartments. Most cells forming the exposed surface of the cornea are viable and healthy, but not proliferating. Proliferation is observed when the cornea is wounded. Methods for measuring wound healing are known in the art (reviewed in Woo et al., Experimental Eye Research, 80:633-642, 2000). Methods for measuring cell survival are known in the art and include various cellular, molecular, biochemical, and histological techniques.

Lacritin is naturally produced in moderately large quantities by the lacrimal gland for release into the corneal tear film where it can be readily be detected by ELISA. The therapeutic potential of lacritin in promoting the health of the ocular surface is therefore considerable, particularly as environmental exposure to pollutants and UV exposure increases, and as the proportion of the population, suffering from Dry Eye expands. Therefore, the invention further relates to inducing increased lacrimal gland secretion of tears.

The cornea is the main refracting surface of the eye and is vulnerable to environmental hazards or insult including exposure (direct trauma, drying, radiant and ionizing energy), infectious agents (bacteria, viruses-notably herpes simplex and herpes zoster-fungi, and parasites), and inflammation, sometimes in association with systemic dermatologic disorders such as atopic dermatitis, cicatricial pemphigoid, rosacea, and erythema multiforme (Stevens-Johnson syndrome). Bacteria include pseudomonas. Keratitis is an inflammation or infection of the cornea. It is often associated with inflammation of the iris (iritis) or of the uveal tract—the iris, ciliary body, and choroid (uveitis). Keratitis combined with uveitis or iritis is seen commonly in Reiter's disease and occasionally Behcet's disease. Keratitis and uveitis may also occur with herpes simplex infection, in sarcoidosis, and in collagen vascular diseases.

As described above, a host of mediators are implicated in the development and progression of corneal inflammation, such as the proinflammatory cytokines TNF-$\alpha$, IL-1$\beta$, IL-6, and the chemokine IL-8. Also involved are the arachidonic acid-derived eicosanoids which are produced by the activity of cyclooxygenases (primarily PGE2), lipooxygenases (12 (s)-HETE) and cytochrome P450 (12 (r)-HETE). Topically applied lacritin could have a huge impact on ocular surface health. Therefore, in one embodiment of the invention, lacritin is useful as an antagonist to inflammatory processes such as those induced or supplemented by proinflammatory agents such as proinflammatory cytokines. In one aspect, a lacritin polypeptide, or a fragment or homolog thereof, enhances survival of cells against proinflammatory cytokines.

In one aspect, proinflammatory cytokines can be evaluated by ELISA. The arachidonic acid derivatives can be studied by measuring metabolites via a lipid based assay using HPLC. The apoptotic cascade can be investigated using cell viability assays (MTT and flow cytometry), colorinetric detection of the cleaved substrates of caspases (−3, −8 and −9), cytochrome c release from the mitochondria and others. In another aspect, immunofluorescence using various antibodies (such as PKC$\alpha$, NF$\kappa$B, NFAT) can be investigated to determine which signaling pathways are being effected. Luciferase reporter assays can used to determine the role of NF$\kappa$B and NFAT in human corneal epithelial cells. In one aspect, lacritin and its different deletion constructs along with various pharmacological inhibitors such as PKC$\alpha$ inhibitor Go6976 and PLC inhibitor U73122 can be used to examine the inhibitory effects of lacritin on proinflammatory cytokines. Sensitivity to ocular surface inflammation can be compared in normal mice relative to lacritin-knockin mice.

In accordance with one embodiment, a method of reducing or preventing ocular cell death in a mammalian species after contact with an environmental insult, or in response to an ocular-associated disease, disorder, or condition is provided. The method comprises the steps of contacting the cells that have been exposed to the environmental insult to a composition comprising lacritin, or a fragment, derivative, or homolog thereof. As used herein, cells that are "exposed" to the environmental insult include those cells that have been directly contacted by the environmental insult, as well as those cells that suffer indirectly as a result of direct contact of other cells with the environmental insult. In one embodiment, the ocular cells comprise the corneal epithelial cells. In one embodiment, the exposed cells are contacted with a topically administered ophthalmic formulation comprising a lacritin polypeptide, or a derivative, fragment, or homolog thereof.

The lacritin comprising compositions of the present invention can be administered prophylactically to promote corneal epithelial cell survival in the presence of common environmental insults such as exposure to UV exposure or pollutants, particularly for those individuals that face excessive exposure to such elements. In another embodiment, the lacritin comprising compositions of the present invention are used to regulate an immune response to inflammation and/or bacterial infection. In another embodiment, a lacritin comprising composition can be administered to aid in the healing process following a surgical procedure to the eye, such as cataract or other vision-corrective surgical procedures. The invention encompasses all surgical procedures of the eye, including laser procedures.

In accordance with one embodiment, a method is provided for treating infections of the eye. The method comprises the step of topically administering a composition comprising a lacritin polypeptide to the eye. In one embodiment, the composition further comprises an anti-microbial agent. Suitable ophthalmic anti-microbial agents are known to those skilled in the art and include those described in U.S. Pat. Nos. 5,300,296, 6,316,669, 6,365,636 and 6,592,907, the disclosures of which are incorporated herein. Examples of anti-microbial agents suitable for use in accordance with the present invention include benzalkonium chloride, benzethonium chloride, benzyl alcohol, chlorobutanol, chlorhexidine digluconate or diacetate, methyl and propyl hydroxybenzoate (parabens), phenylethyl alcohol, phenylmercuric acetate or nitrate, sorbic acid, and thimerosal.

The lacritin comprising compositions of the present invention are also used in one embodiment for the treatment and/or prevention of corneal abnormalities in normal individuals subjected to environmental insult. Such insults include air pollution, pollen, extremes of temperature (i.e., steel workers) and space travel. The compositions can also be used to treat and alleviate Dry Eye corneal epithelial defects and inflammation resulting from Sjogren's or non-Sjogren's syndrome as well as epithelial defects and inflammation that can result from extended contact lens use. In addition, the lacritin comprising compositions can be used to enhance the success of corneal grafts or corneal repair following corneal surgery.

The present invention also encompasses the use of nucleic acid sequences that encode the lacritin polypeptide, or fragments, homologs, and derivatives thereof. In particular the present invention is directed to nucleic acid sequences comprising the sequence of SEQ ID NO: 1, SEQ ID NO: 2, SEQ ID NO: 3, or fragments thereof. In one embodiment, purified nucleic acids comprising at least 8 contiguous nucleotides (i.e., a hybridizable portion) that are identical to any 8 contiguous nucleotides of SEQ ID NO: 1 are provided. In other embodiments, the nucleic acids comprises at least 25 (contiguous) nucleotides, 50 nucleotides, 100 nucleotides, 200 nucleotides, or 500 nucleotides of SEQ ID NO: 1. In another embodiment, the nucleic acid sequence comprises the sequence of SEQ ID NO: 3 or a 25 bp nucleic acid sequence that is identical to a contiguous 25 bp sequence of SEQ ID NO: 3. It is also directed to nucleic acid sequences encoding the peptides comprising the amino acid sequences of SEQ ID NO:4 and SEQ ID NO:10.

In another embodiment of the present invention, nucleic acid sequences encoding a lacritin polypeptide, or fragments or homologs thereof, can be inserted into expression vectors and used to transfect cells to express recombinant lacritin in the target cells. In accordance with one embodiment, the nucleic acid sequence of SEQ ID NO: 3 are inserted into a eukaryotic expression vector in a manner that operably links the gene sequences to the appropriate regulatory sequences, and lacritin is expressed in a eukaryotic host cell. Suitable eukaryotic host cells and vectors are known to those skilled in the art. In particular, nucleic acid sequences encoding lacritin may be added to a cell or cells in vitro or in vivo using delivery mechanisms such as liposomes, viral based vectors, or microinjection. Accordingly, one aspect of the present invention is directed to transgenic cell lines that contain recombinant genes that express the lacritin polypeptide of SEQ ID NO: 4.

The present invention is also directed to nucleic acid constructs for expressing heterologous genes under the control of the lacritin gene promoter. In accordance with one embodiment a nucleic acid construct is provided comprising a nucleic acid sequence selected from the group consisting of SEQ ID NO: 5, SEQ ID NO: 6, SEQ ID NO: 7 and SEQ ID NO: 8 operably linked to a heterologous gene. In accordance with one embodiment, the heterologous gene is a reporter gene that encodes for a marker. The marker can be any gene product that produces a detectable signal and includes proteins capable of emitting light such as Green Fluorescent Protein (GFP) (Chalfie et al., 1994, Science 11: 263:802-805) or luciferase (Gould et al., 1988, Anal. Biochem. 15:175:5-13), as well as proteins that can catalyze a substrate (e.g., such as β-galactosidase). The marker may also comprise intracellular or cell surface proteins that are detectable by antibodies. Reporter molecules additionally, or alternatively, can be detected by virtue of a unique nucleic acid sequence not normally contained within the cell.

As used herein, AGFP@ refers to a member of a family of naturally occurring fluorescent proteins, whose fluorescence is primarily in the green region of the spectrum. The term includes mutant forms of the protein with altered or enhanced spectral properties. Some of these mutant forms are described in Cormack, et al., 1996, Gene 173: 33-38 and Ormo, 1996, Science 273:1392-1395, the entireties of which are incorporated herein by reference. The term also includes polypeptide analogs, fragments or derivatives of GFP polypeptides which differ from naturally-occurring forms by the identity or location of one or more amino acid residues, (e.g., by deletion, substitution or insertion) and which share some or all of the properties of the naturally occurring forms so long as they generate detectable signals (e.g., fluorescence). Wild type GFP absorbs maximally at 395 nm and emits at 509 nm. High levels of GFP expression have been obtained in cells ranging from yeast to human cells. The term also includes Blue Fluorescent Protein (BFP), the coding sequence for which is described in Anderson, et al., 1996, Proc. Natl. Acad. Sci. USA 93:16:8508-8511, incorporated herein by reference.

Another embodiment of the present invention comprises antibodies that are generated against the lacritin polypeptide. These antibodies can be formulated with standard carriers and optionally labeled to prepare therapeutic or diagnostic compositions. Antibodies to lacritin are generated using methods that are well known in the art. Such antibodies may include, but are not limited to, polyclonal, monoclonal, chimeric (i.e., "humanized" antibodies), single chain (recombinant), Fab fragments, and fragments produced by a Fab expression library. These antibodies can be used as diagnostic agents for the diagnosis of conditions or diseases characterized by expression or overexpression of lacritin, or in assays to monitor patients being treated for a conditions or diseases characterized by inappropriate lacritin expression. The antibodies useful for diagnostic purposes may be prepared in the same manner as those described above for therapeutics. The antibodies may be used with or without modification, and may be labeled by joining them, either covalently or non-covalently, with a marker. In accordance with one embodiment an antibody is provided that specifically binds to the protein of SEQ ID NO: 4, and more preferably the antibody is a monoclonal antibody.

The invention also encompasses antibodies, including anti-idiotypic antibodies, antagonists and agonists, as well as compounds or nucleotide constructs that inhibit expression of the lacritin gene (transcription factor inhibitors, antisense and ribozyme molecules, or gene or regulatory sequence replacement constructs), or promote expression of lacritin (e.g., expression constructs wherein the lacritin coding sequences, such as SEQ ID NO: 3 are operatively associated with expression control elements such as promoters, promoter/enhancers, etc.).

The present invention also encompasses antigenic compositions for raising antibodies against lacritin. In one embodiment, an antigenic composition is provided comprising the polypeptide of SEQ ID NO: 4 or an antigenic fragment thereof.

Current tear supplements are not popular with patients, in part because the relief obtained from such products is very brief (less than 15 min). Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Examples of these treatment approaches are disclosed in U.S. Pat. No. 4,131,651 (Shah et al.), U.S. Pat. No. 4,370,325 (Packman), U.S. Pat. No. 4,409,205 (Shively), U.S. Pat. Nos. 4,744,980 and 4,883,658 (Holly), U.S. Pat. No. 4,914,088 (Glonek), U.S. Pat. No. 5,075,104 (Gressel et al.) and U.S. Pat. No. 5,294,607 (Glonek et al.) the disclosures of which are incorporated herein. Existing ophthalmic formulations may also include TGF-beta, corticosteroids, or androgens. All are non-specific for the eye and have systemic effects. In contrast, lacritin is highly restricted to the eye and is a natural constituent of human tears and the tear film.

An ophthalmic formulation comprising lacritin, or fragments, homologs, or derivatives thereof (for example, an artificial tear fluids containing lacritin), is highly desirable due to the activity of lacritin and its localized effects. In accordance with one embodiment of the invention, compositions comprising lacritin are used to enhance corneal wound healing, and/or treat patients having deficient tear output. More particularly, lacritin is used in accordance with one embodiment to treat Dry Eye syndromes, including Sjogren's syndrome and to enhance corneal wound healing by topical application of compositions comprising the lacritin polypeptide. In accordance with one embodiment, a composition comprising a pharmaceutically acceptable carrier and a therapeutically effective amount of substantially pure polypeptide comprising the amino acid sequence of SEQ ID NO: 4, or fragments or derivatives thereof, is used to treat Dry Eye syndromes. In a further embodiment, an ophthalmic composition comprising a purified lacritin polypeptide and a purified anti-microbial agent is provided and used to treat microbial infections of the eye. Suitable ophthalmic anti-microbial agents are known to those skilled in the art and include those described in U.S. Pat. Nos. 5,300,296, 6,316,669, 6,365,636 and 6,592,907, the disclosures of which are incorporated herein.

The lacritin compositions of the present invention can be formulated using standard ophthalmic components, and preferably, the compositions are formulated as solutions, suspensions, and other dosage forms for topical administration. Aqueous solutions are generally preferred, based on ease of formulation, biological compatibility (especially in view of the malady to be treated, e.g., dry eye-type diseases and disorders), as well as a patient's ability to easily administer such compositions by means of instilling one to two drops of the solutions in the affected eyes. However, the compositions may also be suspensions, viscous or semi-viscous gels, or other types of solid or semi-solid compositions.

The compositions of the present invention may include surfactants, preservative agents, antioxidants, tonicity agents, buffers, preservatives, co-solvents and viscosity building agents. Various surfactants useful in topical ophthalmic formulations may be employed in the present compositions. These surfactants may aid in preventing chemical degradation of lacritin and also prevent the lacritin from binding to the containers in which the compositions are packaged. Examples of surfactants include, but are not limited to: Cremophor® EL, polyoxyl 20 ceto stearyl ether, polyoxyl 40 hydrogenated castor oil, polyoxyl 23 lauryl ether and poloxamer 407 may be used in the compositions. Antioxidants may be added to compositions of the present invention to protect the lacritin polypeptide from oxidation during storage. Examples of such antioxidants include, but are not limited to, vitamin E and analogs thereof, ascorbic acid and derivatives, and butylated hydroxyanisole (BHA).

Existing artificial tears formulations can also be used as pharmaceutically acceptable carriers for the lacritin active agent. Thus in one embodiment, lacritin is used to improve existing artificial tear products for Dry Eye syndromes, as well as develop products to aid corneal wound healing. Examples of artificial tears compositions useful as carriers include, but are not limited to, commercial products, such as Tears Naturale®, Tears Naturale II®, Tears Naturale Free®, and Bion Tears® (Alcon Laboratories, Inc., Fort Worth, Tex.). Examples of other phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), U.S. Pat. No. 5,578,586 (Glonek et al.); the foregoing patents are incorporated herein by reference to the extent they disclose phospholipid compositions useful as phospholipid carriers of the present invention.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoises ("cps"). Preferred compositions containing artificial tears or phospholipid carriers and will exhibit a viscosity of about 25 cps.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

Because the gene promoter regulating lacritin gene expression is the most specific of any previously described lacrimal gland gene, the regulatory elements of this gene could be used to express other gene products in the eye. In particular, the lacritin gene promoter can be operably linked to a wide variety of exogenous genes to regulate the expression of the gene products to the lacrimal gland and/or used as gene therapy to treat Dry Eye syndromes.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide is purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines ($-NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for analogs of proteins. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

The invention also includes a kit comprising the composition of the invention and an instructional material which describes administering the composition to a subject. In another embodiment, this kit comprises a (preferably sterile) solvent suitable for dissolving or suspending the composition of the invention prior to administering the composition.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, and to birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, intravenous, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyamide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose.

Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifingal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to a subject, preferably a human, range in amount from 1 µg to about 100 g per kilogram of body weight of the subject. While the precise dosage administered will vary depending upon any number of factors, including but not limited to, the type of subject and type of disease state being treated, the age of the subject and the route of administration. Preferably, the dosage of the compound will vary from about 1 mg to about 10 g per kilogram of body weight of the subject. More preferably, the dosage will vary from about 10 mg to about 1 g per kilogram of body weight of the subject The compound may be administered to a subject as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the subject, etc.

The invention also includes a kit comprising the composition of the invention and an instructional material which describes adventitially administering the composition to a cell or a tissue of a subject. In another embodiment, this kit comprises a (preferably sterile) solvent suitable for dissolving or suspending the composition of the invention prior to administering the compound to the subject.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a subject. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

EXAMPLE 1

Isolation of the Lacritin Gene cDNA and Genomic Cloning of Lacritin

Isolation of the lacritin gene has been previously described in detail (see Laurie et al., (U.S. Patent Pub. No. US 2004/0081984, published Apr. 29, 2004), which is incorporated by reference in its entirety herein. Duplicate filters containing plaques ($5 \times 10^4$ per filter) from each of ten sublibraries of a human lacrimal gland cDNA library were prehybridized at 42° C. for 4 hr in 5× Denhardt's, 6.76×SSC, 10 mM sodium phosphate, 1 mM EDTA, 0.5% SDS and 182 µg/ml salmon sperm DNA, and then hybridized overnight at 42° C. with one of two overlapping 23-mer oligonucleotides [AGCTGGGGCACAGGCACCCGCAC; SEQ ID NO: 11] and [GGGGTTCTGGGGCTGCAGCTGGG; SEQ ID NO: 12] All nucleotide sequences have been submitted to the GenBank/EBI Data Bank with accession numbers af238867 (cDNA) and ay005150 (genomic).

Northern Analysis

Human lacrimal and submandibular glands were obtained during autopsy through the Southern division of the Cooperative Human Tissue Network within 18 hours of death and most within 8 hours to minimize autolytic degradation, as previously described in detail (see Laurie et al., (U.S. Patent Pub. No. US 2004/0081984, published Apr. 29, 2004). The tenets of the Declaration of Helsinki were followed and informed consent and full IRB approval were obtained. Donors were without known systemic bacterial or viral infections, and tissues were normal as determined from cause of death, pathology reports and in most cases histological examination. Tissues were snap frozen in liquid nitrogen after removal and stored at −85° C. until used for RNA preparation. Total RNA was extracted from 100-300 mg of tissue using a commercial version of the acidified guanidine thiocyanate/phenol method (RNazol B, Tel-Test, The Woodlands, Tex.). Purified RNA was dissolved in diethylpyrocarbonate-treated water, and the concentration and purity determined from the A260/280 absorption values. A ratio close to 2.0 was considered acceptable.

RNA integrity was initially determined by electrophoresis of ethidium bromide-complexed RNA samples in a gel containing 0.22 M formaldehyde. Samples that did not show prominent 28S and 18S rRNA bands in a 1:1-2:1 ratio under UV light were rejected. For blotting, RNA (5 µg/lane) was separated on a 0.8% agarose gel under denaturing conditions (Laurie et al., 1989) and transferred to nitrocellulose. Also assayed were two purchased (cat #7756-1 and 7751-1; Clontech Labs, Palo Alto Calif.) Northern blots with multiple human fetal and adult poly A+ RNA's and a dot blot (cat #7770-1; Clontech Labs) containing fifty different human poly A+ RNA's together with control RNA's and DNA's. Blots were hybridized with [32P]-labeled lacritin insert, washed in 0.1×SSC, 0.1% SDS (Northern) or 2×SSC, 0.1% SDS (dot blot) at 55° C., and exposed to X-ray film. Dot blots were then quantitated using NIH Image by measurement of pixel gray values of individual dots.

PCR Analysis and Chromosome Mapping

Alternative splicing was examined by RT-PCR using human submandibular or lacrimal total RNA and initial priming with oligo dT, or in a gene specific manner with lacritin reverse primer CGCTACAAGGGTATTTAAGGC (SEQ ID NO: 13) corresponding to nucleotides 523 to 503 from lacritin cDNA). Subsequent amplification with lacritin forward primer ACTCACTCCTCATCCCAAAG (SEQ ID NO: 14; from exon 1; lacritin cDNA nucleotides 32 to 51) and reverse primer TTTTCAGCTTCTCATGCCC (SEQ ID NO: 15;

from exon 5; lacritin cDNA nucleotides 480 to 462) involved denaturation for 2 min at 94° C., thirty cycles of amplification (94° C. for 30 sec, 52° C. for 30 sec & 72° C. for 1 min), and a final cycle for 5 min at 72° C. PCR product was analyzed in agarose gels.

FISH mapping (Genome Systems; St. Louis, Mo.) was performed as previously described in detail (see Laurie et al., (U.S. Patent Pub. No. US 2004/0081984, published Apr. 29, 2004)

Results:

Lacrimal acinar cells are polarized exocrine secretory cells containing some mRNA's that are remarkably under-represented in gene data banks and may code for a rich array of differentiation factors—a presumption underlying the paired oligonucleotide screening of a little used human lacrimal gland cDNA library. Among the clones identified by this approach was a novel cDNA sequence (SEQ ID NO: 2) represented by several independent clones and corresponding to a 760 bp transcript and the corresponding amino acid sequence (SEQ ID NO: 4). The secreted gene product of this lacrimal gland-specific transcript was designated "Lacritin."

The lacritin nucleic acid sequence contains a 417 bp open reading frame that predicts a 14.3 kDa hydrophilic protein core with a 19 amino acid signal peptide giving rise to a mature secreted core protein of 12.3 kDa with an isoelectric point of 5. Noteworthy is a moderately high level of glycosylation with six putative O-glycosylation sites between residues 52 and 64, and a single N-glycosylation site near the C-terminus, indicating that lacritin is a moderately well-glycosylated core protein much like the neuroglycan C glycosaminoglycan binding domain and fibulin-2 amino globular domain to which lacritin bears partial homology. Northern Blot analysis indicates a high level of lacrimal gland specificity.

In FASTA searches of the primate database, partial homology is detected with the glycosaminoglycan binding region of human neuroglycan C (32% identity over 102 amino acids; BestFit quality=83 versus 37 5 when lacritin sequence was randomized) and with the "cysteine-free", possibly mucin-like, amino globular region of human fibulin-2 (30% identity over 81 amino acids; BestFit quality=81 versus 38$ 5 for random). Although all three are rich in O-glycosylation, positioning of serine and threonine is not strictly shared; and both lacritin and fibulin-2 lack glycosaminoglycan binding sites. Neuroglycan C (af059274) is a component of brain extracellular matrix (anchored by transmembrane domain; Yasuda et al., 1998). Fibulin-2 (x89494) is widely dispersed in basement membranes and stroma of embryonic and adult tissues (Sasaki et al., 1999). Searches of non-primate databases pointed to modest homologies with *T. Cruzi* mucin-like protein (af036464; BestFit quality=78 versus 46 10); *P. falciparum* merozoite surface antigen 2 (u91656; BestFit quality=76 versus 53 6) and *P. Taeda* putative arabinogalactan protein (af101791; BestFit quality=74 versus 37.4).

No matching or homologous EST's were detected, in keeping with lacritin=s abundance in human lacrimal gland and restricted expression elsewhere. Northern analysis revealed a strong 760 bp lacrimal gland message, and weaker submandibular and thyroid gland messages of the same size. No message was detected in human adult adrenal gland, testis, thymus, pancreas, small intestine, or stomach; nor in human fetal brain lung, liver, or kidney. Similarly, in a commercial dot blot of fifty different human tissue poly A+ RNA=s that excluded lacrimal gland, lacritin expression was found only in submandibular gland ("salivary gland"), and to a lesser degree in thyroid. The lacritin coding sequence was subcloned into pET-28b and pcDNA3.1/myc-His(+)C to generate recombinant bacterial and mammalian (293-T cell) lacritin, respectively. Both forms of lacritin displayed anomalous migration in SDS PAGE.

EXAMPLE 2

Characterization of Lacritin Expression and Function
Preparation of Recombinant Lacritin and Anti-Lacritin Antisera These reagents were prepared as previously described in detail (see Laurie et al., (U.S. Patent Pub. No. US 2004/0081984, published Apr. 29, 2004).

Cell Function Analysis

Freshly isolated rat lacrimal acinar cells, and HSG (human salivary gland) ductal and HCE (human corneal epithelial) cell lines were used to study lacritin function. For secretion studies, rat acinar cells were plated serum-free overnight on wells co-coated with 0.05 µM laminin 1 (to ensure adhesion) and 0 to 20 µM lacritin, or alternatively with laminin-1 (0.05 µM) and treated the next day with serum-free medium containing 0 to 162 ng/ml of soluble lacritin for four hours. Unstimulated and stimulated (carbachol $10^{-4}$ M/VIP $10^{-8}$ M) secretions were then collected, assessed (peroxidase assay) and normalized to µg cellular DNA. To study tyrosine phosphorylation, overnight serum-free cultures of both rat lacrimal acinar and HSG cells were washed and treated with 10 ng/ml of soluble lacritin for 0.5, 2.5, 10, and 30 minutes. Py(20) anti-phosphotyrosine antibody immunoprecipitation of cell lysates was then examined in Western blots of 7% SDS PAGE gels using Py(20) and ECL for detection. Calcium signaling in human corneal epithelial cells was similarly carried out in serum-free culture (Trinkaus-Randall et al., 2000; Klepeis & Trinkaus-Randall, in preparation). HCE cells were grown to confluency on glass coverslips in keratinocyte media (Life Technologies, Rockville Md.) containing bovine pituitary extract (30 µg/ml), EGF (0.1 ng/ml) and penicillin/streptomycin, and rendered quiescent 18 hrs before loading with Fluo-3AM (2 µM; Molecular Probes, Eugene Oreg.) at 37° C. for 30 minutes. Using an inverted Zeiss 510 LSM for visualization, 50 second baseline images were first recorded. While the laser was running, lacritin was added (final concentration 4 and 40 ng/ml) and the response continually monitored every 786 msec for a minimum of 200 sec.

ECM Binding Studies

Binding studies were carried out in 96 well plates coated with 10 µg/well of collagen IV, laminin-1, entactin/nidogen-1, collagen I, fibronectin, vitronectin, EGF, heparin or BMS. Wells were washed, blocked (PBS-T), incubated with 0-30 nM lacritin (in PBS-T containing 1% BSA) for 1 hr (4° C.), washed and detected with anti-lacritin antibody (1/1000) by ELISA.

Results:

Antibodies prepared against bacterial lacritin were applied to sections of human lacrimal and salivary glands and to tissue microarrays containing formalin-fixed, paraffin embedded sections of 75 different human tissues and organs (see Table I, as previously published in Laurie et al., (U.S. Patent Pub. No. US 2004/0081984, published Apr. 29, 2004). Immunoreactivity was clearly observed in secretory granules of acinar cells in lacrimal and major and minor salivary glands, but was not apparent in other epithelia or stroma. Presence in thyroid was equivocal (Table I). Frequency of acinar cell staining was high in lacrimal gland, whereas only scattered salivary acinar cells were reactive. Immunoreactivity was also apparent in secretions within lumens of lacrimal and salivary ducts. By ELISA, lacritin was detected in human tears and to a lesser extent in saliva.

TABLE I

Restricted Immunolocalization of Lacritin in Human Organs[a]

| Organ | Intensity |
|---|---|
| adrenal medulla | – |
| adrenal cortex | – |
| appendix | – |
| bladder | – |
| bone/marrow | – |
| brain | – |
| breast | – |
| bronchus | – |
| cerebellum | – |
| colon | – |
| epididymis | – |
| esophagus | – |
| gallbladder | – |
| ganglia | – |
| heart | – |
| kidney | – |
| lacrimal gland | ++++ |
| liver | – |
| lung | – |
| lymphatics | – |
| ovary | – |
| pancreas | – |
| parathyroid | – |
| parotid gland | + |
| periph. nerve | – |
| pituitary gland | – |
| placenta | – |
| prostate | – |
| testes | – |
| minor salivary | + |
| sem vesicle | – |
| skel muscle | – |
| skin | – |
| small intestine | – |
| spinal cord | – |
| spleen | – |
| stomach | – |
| subman gland | ++ |
| testis | – |
| thymus | – |
| thyroid gland | ? |
| uterus/vagina | – |

[a] relative intensity; not all tissues shown

Lacritin function of three types of epithelial cells was assessed in serum-free cultures of: 1) lacrimal acinar; 2) salivary ductal; and 3) corneal epithelial cells using secretion (acinar), proliferation (ductal), tyrosine phosphorylation (acinar, ductal) and calcium signaling (corneal epithelial) assays. Freshly isolated rat lacrimal acinar cells were plated on increasing amounts of lacritin (with a constant small amount of laminin 1 to ensure adherence), or on laminin-1-coated wells in which lacritin was added to the medium. Both coated and soluble lacritin enhanced unstimulated secretion in a dose-dependent manner (see FIG. 1, as previously published Laurie et al., (U.S. Patent Pub. No. US 2004/0081984, published Apr. 29, 2004), but no effect was observed on the stimulated secretory pathways activated by the agonists carbachol and VIP. These results suggest an autocrine or paracrine role, possibly via receptors on the luminal acinar cell surface. As lacritin flows from acini, it contacts ductal epithelial cells and finally the corneal epithelium.

Figure 2A:
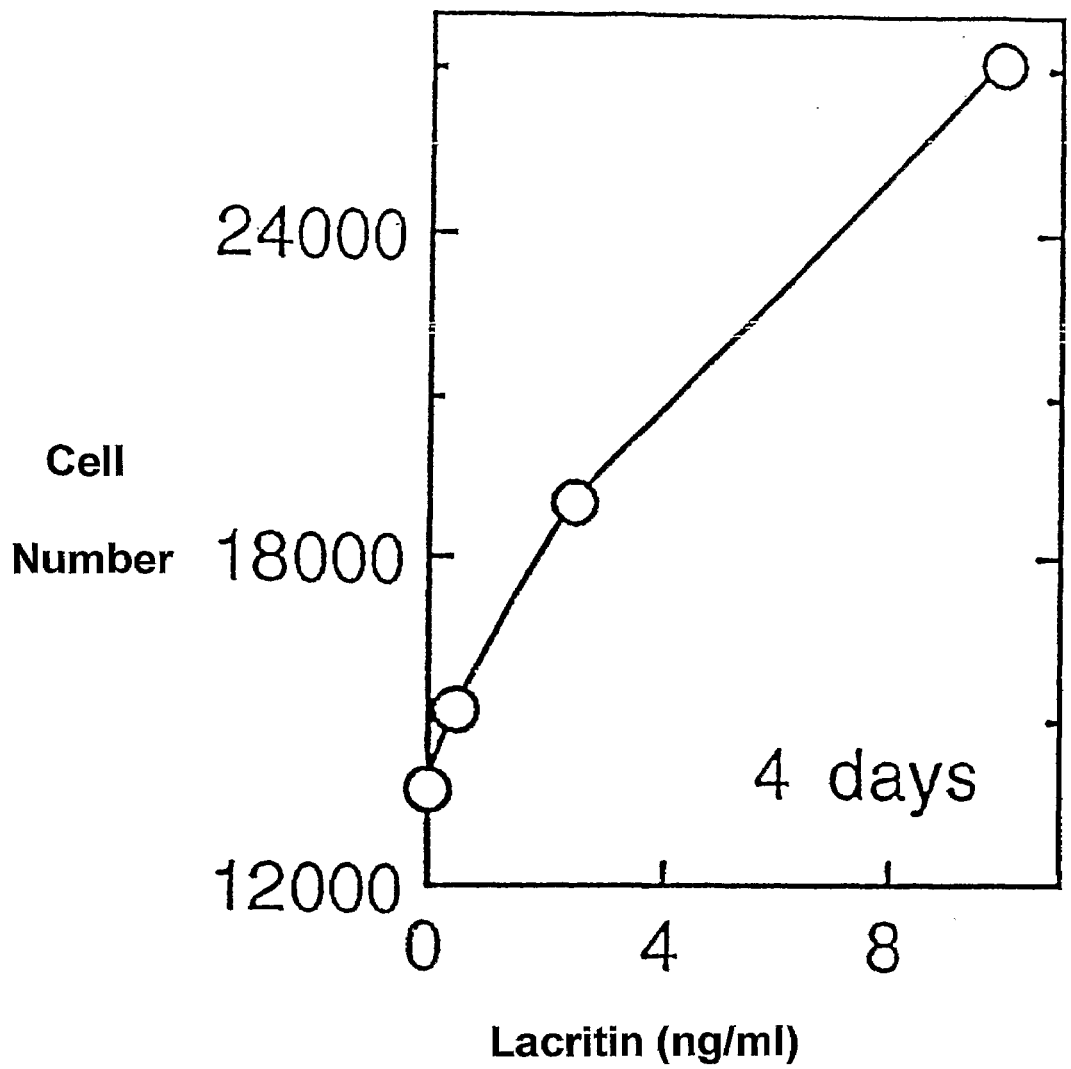
FIGS. 2A and 2B represent lacritin-induced proliferation and tyrosine phosphorylation.
Figure 2B:
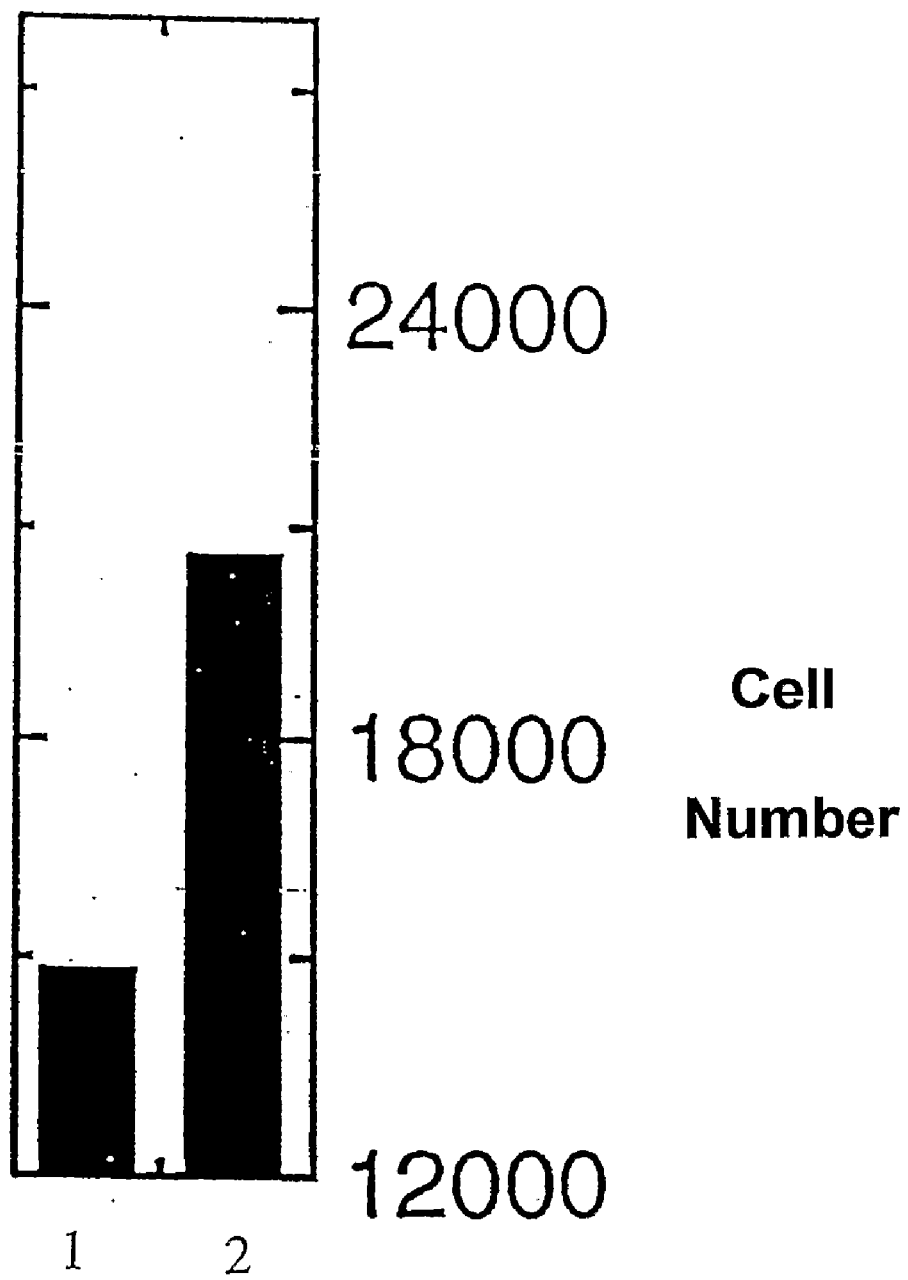

Quiescent human submandibular ductal ('HSG') cells were cultured in serum-free media containing increasing amounts of lacritin and cell proliferation was studied. The lacritin cultures looked healthier; after four days, a dose-dependent increase in ductal cell number was apparent (see FIG. 2A; as previously published in Laurie et al., (U.S. Patent Pub. No. US 2004/0081984, published Apr. 29, 2004) that reached a level more than twofold that of the BSA (10 ng/ml) negative control (see FIG. 2b). The same level of lacritin promoted the transient tyrosine phosphorylation of a 48 kDa band in both HSG and rat lacrimal cells.

Next, calcium signals in human corneal epithelial cells were examined. Whereas the basal level of signaling was negligible, the addition of lacritin resulted in rapid and sustained calcium waves that propagated throughout the cells. Wave onset preceded that of the usual response to epidermal growth factor (20-40 sec), and the amplitude of the response depended on the concentration of lacritin. To ensure that bacterial lipopolysaccharide (a possible contaminant of recombinant protein preps) was not involved, samples were tested in the *limulus amebocyte* lysate assay; and no lipopolysaccharide was detected (<0.05 EU/ml). Finally, the ability of lacritin to bind the tear film components fibronectin or vitronectin was examined; as well as constituents of the periacinar basement membrane that might harbor small amounts of lacritin not detectable by the immunohistochemical procedure. Lacritin displayed a remarkable avidity for fibronectin and vitronectin, and there was a strong basement membrane binding attributable to collagen IV, nidogen/entactin and laminin-1-similar to that observed for fibulin-2. No binding was observed to collagen I, EGF or heparin.

The rather broad lacritin lacrimal gland message was suggestive of alternatively spliced forms, or RNA degradation. The same was not true for submandibular gland in which a discrete, but much less intense signal was apparent. To address this issue and to gain information on how the lacritin gene is arranged, a 12.4 kb genomic fragment was sequenced, the largest lacritin-positive fragment readily obtainable from the lacritin genomic clones. The gene consists of five exons preceded by a predicted promoter sequence 109 to 59 bp upstream of the translation start site (promoter score=1.0; NNPP/Eukaryotic). Exon 1 encodes the complete signal peptide and includes 38 bp of 5' untranslated sequence. Exon 3 contains sequence for all putative 0-glycosylation sites. The predicted N-glycosylation site is formed at the exon 4/exon 5 splice junction. Exon 5 includes 53 bp of 3' untranslated sequence. Three potential polyadenylation sites are detected 367, 474 and 534 bp downstream of exon 5, the first of which would be in keeping with a 760 bp transcript. Sequences at exon-intron boundaries all conform to predicted splice donors or acceptors, with the exception of the exon 4 splice acceptor. Intronic sequences revealed common intronic repeat elements. Also independently discovered on a separate genomic fragment was a lacritin pseudogene lacking 38 bp of 5' exon 1 sequence.

To examine possible alternative splicing, RT-PCR was used with submandibular or lacrimal gland cDNA as template and forward and reverse primers from exons 1 and 5, respectively, each including untranslated flanking sequence. A single PCR product was detected in both organs whose size (449 bp) was in keeping with transcription from all five exons without alternative splicing. FISH revealed that the lacritin gene is located on chromosome 12, a result confirmed by double labeling with a probe for 12q15. Measurement of ten specifically labeled chromosomes located the lacritin gene approximately 16% of the distance from the centromere to the telomere of 12q, an area that corresponds to 12q13. Also found on 12q13 is a rare genetic alacrimia known as Triple A Syndrome. Attempted PCR using lacritin genomic primers and BAC templates spanning the triple A syndrome region failed to produce PCR product. The lacritin gene is partially included in draft sequences AC068789.4, AC025686.2 and AC025570.6 pointing to a 12q13 location approximately 65.1 to 65.9 Mbp from the centromere.

The original discovery of lacritin developed from the hypothesis that multiple extracellular factors trigger glandular differentiation, particularly growth factors and components of the surrounding extracellular matrix. Indeed, partial or failed acinar formation has been reported in mice lacking the TGFβ superfamily members or receptors, ErbB4, the progesterone receptor, the extracellular matrix glycoprotein osteopontin, EGF receptor (with TGFα and amphiregulin), fibroblast growth factor receptor 2 (IIIb), or the growth factor FGF-10. Linking such factors to the secretory function of acinar cells in culture has proven more complex. Nonetheless, it is clear that the periacinar mesenchymal and hormonal environment affect glandular development and function, and that both autocrine and paracrine regulation play important roles. Most delicate are primary cultures of freshly isolated exocrine cells, particularly lacrimal acinar cells that functionally dedifferentiate in the absence of lacrimal-1 and lower molecular mass factors derived from the extracellular matrix and elsewhere.

Introduction of recombinant lacritin to cultures of lacrimal acinar, salivary ductal and corneal epithelial cells provided interesting functional insights. Lacrimal acinar cells displayed enhanced unstimulated (but not stimulated) secretion and rapid tyrosine phosphorylation of a 48 kDa protein. Ductal cells phosphorylated the same 48 kDa band and were proliferative. A rapid and sustained calcium transient was noted in corneal epithelial cells. Thus, all cell types contributing to or benefiting from lacritin outflow appear to be lacritin-inducible, whereas controls were negative and there was no evidence of contaminating bacterial lipopolysaccharide (known to be proliferative in immune cell cultures). How lacritin acts remains to be elucidated. Without wishing to be bound by any particular theory, possibly a common receptor(s) is mediatory, ligation of which may be jointly linked to tyrosine phosphorylation and calcium release as in neural retina where tyrosine kinases have been associated with capacitative calcium entry and inositol-3-phosphate induced release of intracellular calcium stores. Alternatively, lacritin signaling in the three cell types may differ. Lacrimal acinar, ductal and corneal epithelial cells perform strikingly different functions. Although some intracellular signaling machinery may be common, others are unique, and some common machinery may be put to different use. Calcium signaling in lacrimal acinar cells is most frequently a downstream effect of muscarinic receptor ligation that mediates the release of tear proteins by the stimulated secretory pathway, a pathway apparently unaffected by lacritin. Yet, subtleties in calcium amplitude, frequency and localization, dependent on the nature and dose of the agonist, can have dramatically different effects. Contrasting lacritin is BM180, a periacinar basement membrane constituent that appears to act only on the stimulated secretory pathway. Balancing the amounts of available lacritin and BM180 may offer a simple mechanism by which secretory capacity in adult and developing glands may be controlled.

Immunolocalization of lacritin in secretory granules, in secretory content of ducts and in tears was extended by binding studies revealing a remarkable affinity for tear constituents fibronectin and vitronectin. Though not immunodetected elsewhere, lacritin also bound the common periacinar basement membrane components nidogen/entactin, collagen IV, and laminin-1; but not collagen I, EGF or heparin. Similar binding properties have been reported for fibulin-2. Although the significance and precise nature of these interactions remains to be determined, basement membrane binding is perhaps analogous to growth factors whose extracellular matrix accumulation, although functionally potent, is often too low for reliable immunodetection. Alternatively, basement membrane binding (if any) could possibly occur secondary to tissue damage.

EXAMPLE 3

Characterization of the Lacritin Promoter

Characterization of the lacritin promoter has been previously described in detail (see Laurie et al., U.S. Patent Pub. No. US 2004/0081984, published Apr. 29, 2004).

Without wishing to be bound by any particular theory, it is hypothesized that lacritin gene activity is attributable to an atypically restrictive and powerful promoter working hand in hand with unique enhancer (and possibly repressor) elements in a milieu of appropriate transcription factors and co-regulators. Such tissue-specific transcriptional control equals or exceeds that of the A-crystallin (lens), rhodopsin (retina), aldehyde dehydrogenase class 3 and keratocan genes (cornea), and offers a unique opportunity to initiate a new body of literature on nuclear management of gene expression in the human lacrimal gland.

Mapping of Lacritin Gene Regulatory Elements

Elucidating how lacritin gene expression is targeted to the lacrimal gland will be determined as described below to better understanding lacrimal gene regulation. First of all the identify the lacritin transcription initiation site(s) will be confirmed experimentally. Based on computational promoter analysis, transcription is anticipated to be initiated at a single site located 69 bp upstream ('−69 bp'; 'Neural Network') of the ATG translation start site. The 'TATA-box' and/or 'Initiator' ('Inr') elements of the core promoter play an important role in establishing the start site of transcription in many genes, particularly those highly expressed. As an example, Inr elements at +1, +220 (also TATA-box at +190 bp) and +316 bp (intronic) designate transcription start sites in the human keratocan gene as experimentally confirmed by primer extension; and a TATA-box figures prominently in transcription initiation of _A crystallin, rhodopsin, and aldehyde dehydrogenase gene promoters. If the Neural Network-predicted −94 to −46 bp region does indeed comprise the lacritin core promoter with transcription start site at −69 bp (score=1.0), then putative TATA-box and Inr elements at −52 and −67 bp, respectively should play a key role in transcription initiation. Alternatively, transcription could begin at −62 bp, as suggested by 'CorePromoter'. Primer extension and RNA ligase-mediated 5'-RACE will resolve this question.

For primer extension, advantage will be taken of a 20-mer reverse primer ('LacP83') designed by 'Prime' (GCG, Madison Wis.) which is complementary to nucleotides 64 to 83 bp of lacritin mRNA. As per routine procedure, LacP83 will be end-labeled by phosphorylation with T4 polynucleotide kinase in the presence of [$^{32}$P]ATP, annealed with total lacrimal RNA (100 fmol primer per 10 μg RNA) for 20 min at 58° C., cooled, and then incubated for 30 min at 41° C. with AMV reverse transcriptase (Promega, Madison Wis.) in the presence of deoxynucleotides. Size of newly formed cDNA(s), as analyzed by denaturing SDS PAGE analysis/radiography, provides sufficient information to calculate the approximate transcription start site location(s)—with identification of the 5' terminus(i) determined by semiautomatic ABI sequencing of cDNA from a scaled up non-radioactive extension reaction and RNA ligase-mediated 5'-RACE. Primer extension controls will include replacement of lacrimal RNA with total yeast RNA (or no RNA), and use of an RNA prepared by in vitro transcription with accompanying primer (Promega, Madison Wis.) for which primer extension conditions have been previously established.

For confirmation, RNA ligase-mediated 5'-RACE ('Gene Racer'; Invitrogen) will be utilized. This is a powerful PCR-based modification of primer extension. For this purpose, 1-5 µg of total human lacrimal RNA will be treated with calf intestinal phosphatase (1 U per 10 µl reaction mix) to remove 5' phosphates from degraded RNA and non-mRNA contaminants. Incubation with tobacco acid pyrophosphatase (0.5-1 U per 10 µl reaction mix) eliminates the 5'-CAP structure present only on authentic 5'-ends, and makes possible ligation of a kit-specific RNA oligonucleotide ('GeneRacer RNA Oligo') with T4 RNA ligase (5 Upper 10 µl reaction mix). Subsequent LacP83-primed reverse transcription will generate a single strand cDNA. The cDNA will then be PCR amplified using LacP83 and a primer complementary to the 5' RNA oligo as primer pair, and sequenced to identify the start site(s). In negative PCR controls, amplifications will be attempted in the absence of LacP83 or GeneRacer RNA Oligo or without template, and if banding or smearing is observed further PCR optimization will be carried out (ie. use of less template or fewer PCR cycles or do nested PCR to increase amplicon amount, or use touchdown PCR).

It is anticipated that a single primer extended cDNA band of 152 (or 145) bp will be observed in keeping with a transcription start site at −69 bp (or −62 bp) and inclusion of 83 bp from the 5' end of the primer to the translation start site [69+83 bp (or 62+83 bp)]. This expectation is in agreement with the single transcript apparent by Northern analysis of human salivary gland. The broader human lacrimal band has been interpreted as attributable to mRNA abundance combined with possibly some slight degradation. Although no alternative splicing has been observed, the possibility of a second transcript cannot be completely ruled out.

A luciferase reporter constructs will also be generated and transfection-based regional mapping of lacritin gene regulatory elements will be initiated. It is hypothesized that Bayesian alignment of human and mouse lacritin genes will provide an excellent foundation for interpretation of reporter construct activity, and that evolutionary conservation similarly will make feasible utilization of a rabbit lacrimal acinar cell line as transfection host—the only immortalized cell line from lacrimal gland of any species. This exploratory approach will lay the conceptual groundwork for more detailed studies both in vitro and in vivo.

Lacritin's tissue specificity is presumably founded in the nature and assortment of transcription factor binding modules that comprise its gene promoter and putative enhancer region(s). Lens-preferred expression of the _A-crystallin gene, for example, is governed by a transcription complex of CREB/CREM, _A-CRYBP1, Pax 6, TBP, USF, AP-1 (context of AP-1 important for tissue specificity) and L-maf that nucleates on the 150 bp_A-crystallin promoter. Transfected plasmid constructs that artificially position luciferase or chloramphenicol acetyltransferase expression under the control of intact or progressively 5' shortened (or mutated) promoter regions, has been used previously to identify cis-acting regulatory region of a promoter. The versatile and sensitive 'Dual-Luciferase Reporter Assay System' (Promega) for example sequentially assays both the transfected gene promoter under investigation (as manifested by the level of expressed firefly luciferase) and a co-transfected internal positive HSV-TK control promoter designed to independently drive expression of a synthetic sea pansy luciferase with distinct substrate properties at a constant baseline level (see below). Subsequent investigation in transgenic mice using β-galactosidase as reporter brings chromosomal context into play. Recent availability of a rabbit lacrimal cell line (Nguyen, D. et al., In Vitro Cell Dev Biol Anim., 1999, 35(4): 198-204) and genomic cloning of lacritin now open up this line of investigation to the lacrimal gland field.

If transcription is indeed initiated at −69 or −62 bp, upstream genomic constructs spanning −2435 to −10 bp ('Lacrgen2.4'), −1619 to −10 bp ('Lacrgen1.6') or −856 to −10 bp ('Lacrgen0.9') could include all or most elements necessary for tissue specific and elevated expression. Preparation of each will take advantage of parent amplicon 'LacrgenInit' (−2960 to −10 bp) to be generated by PCR from the 12.4 kb lacritin genomic fragment using reverse primer 'LacP-10/Xho I' (−10 to −31 bp) with an Xho I site incorporated, and forward primer 'LacP-2960' (−2960 to −2942 bp). Primer pairs are designed by 'Prime' (GCG, Madison Wis.). Subsequent digestion of LacrgenInit with XhoI, Bgl II/Xho I or Hind III/Xho I yields fragments Lacrgen2.4, Lacrgen1.6 or Lacrgen0.9, respectively with ends suitable for ready ligation (after gel purification) into the multiple cloning region of pGL3-Basic just upstream of the promoterless and enhancer-less luciferase gene (luc+).

A rabbit lacrimal acinar cell line will be used for the transfection studies. The cells display a strong epithelial morphology and synthesize secretory component, transferrin and transferrin receptor. Importantly, they also express lacritin and are readily transfectable. To carry out transfections, ≈80% confluent serum-containing cultures in 96 well plates will be transiently transfected with Lacrgen2.4, Lacrgen1.6 or Lacrgen0.9 in pGL3-Basic plus internal control phRL-TK plasmid (total of 0.24 µg plasmid/well; 50:1 ratio of pGL3-Basic to phRL-TK) using ≈0.8 µl/well LipofectAMINE 2000 reagent (Invitrogen Life Technologies). Forty-eight hours later, cultures will be gently washed three times in PBS, lysed for 15 minutes in 1× 'Passive Lysis Buffer' (20 µl/well; Promega), and assayed for firefly luciferase upon addition of 'Luciferase Assay Reagent II' (100 µl/well) in an L-Max 96 well plate luminometer (Molecular Devices, Menlo Calif.; online with computer). Readings are zeroed to similarly treated wells containing lysate of cells not transfected. Subsequently, 'Stop & Glo Reagent' (100 µl/well) is added for assay of sea pansy (Renilla) luciferase. Inclusion of identically transfected human 293 cells will serve as a negative control, whereas Araki-Sasaki human corneal epithelial cells (HCE-T) and HSG human salivary cells (both secrete lacritin) are suitable positive controls. Optimal lacrimal LipofectAMINE transfection, and 'Bright-Glo' luciferase assay conditions (Promega), will take advantage of the pGL3-Control vector whereby transfected cells benefit from luc+ expression under SV40 promoter and enhancer control. It is expected that transfection efficiency will be 75-90%, and that one of Lacrgen2.4, Lacrgen1.6 or Lacrgen0.9—likely Lacrgen1.6 or Lacrgen0.9—will best define the minimal sequence required for lacritin promoter activity.

This course of investigation offers a logical starting point for the generation and testing of Lacrgen2.4, Lacrgen1.6 or Lacrgen0.9-derived constructs progressively shortened 5' by nested deletion, an approach applied to the genomic sequencing of the lacritin gene and flanking regions. Making this possible are single Kpn I and Sac I sites just upstream of each insert in the pGL3-Basic multiple cloning region, and lack of any internal Kpn I or Sac I sites in Lacrgen2.4, Lacrgen1.6 or Lacrgen0.9—the latter as determined by Map (GCG). Thus when digested with Kpn I and Sac I, a linear plasmid will be generated in which the Kpn I end is exonuclease III resistant (3' protruding) and the Sac I end (3' recessed) is sensitive. Proximity of Lacrgen2.4, Lacrgen1.6 or Lacrgen0.9 to the Sac I site makes them sensitive to exonuclease shortening. To carry this out, 2 µg of plasmid construct is Kpn I and Sac I digested. After enzyme inactivation (10 min at 70° C.) and cooling on ice, linear plasmid in exonuclease III buffer is treated with exonuclease III in a final volume of 40 μl at 25° C. or 15° C. such as to achieve successive 50-100 bp deletions at 3 minute intervals. 2 μl aliquots of each 3 minute time point are removed to tubes on ice containing S1 nuclease. After all timed aliquots have been taken, plasmid digests are removed from ice, incubated at room temperature for 30 minutes for S1 nuclease digestion of overhangs, heat inactivated, recircularized by blunt end ligation in the presence of T4 DNA ligase, examined in agarose gels and transformed into competent cells with ampicillin selection. Plasmid preps of each are then applied to the transfection (with internal control plasmid) of lacrimal acinar cells, and assessment of luciferase expression.

EXAMPLE 4

Lacritin Enhanced Cell Survival

Lacritin's function in cell survival was first assessed in an antibody array screen. Serum-free cultures of salivary ductal cells were treated either with recombinant lacritin at 10 ng/ml or an equal volume of 1×PBS (dialysis medium for recombinant lacritin) for 1 minute. By using tyrosine phosphorylation as a gauge of activity, it has been found that there was a large decrease in FAS/APO-1 levels (−81%) whereas the activities of cell survival promoting proteins such as bcl-2 were increased (bcl-2: 11%), pointing to lacritin's potentially function as a cell survival factor.

Figure 3A:
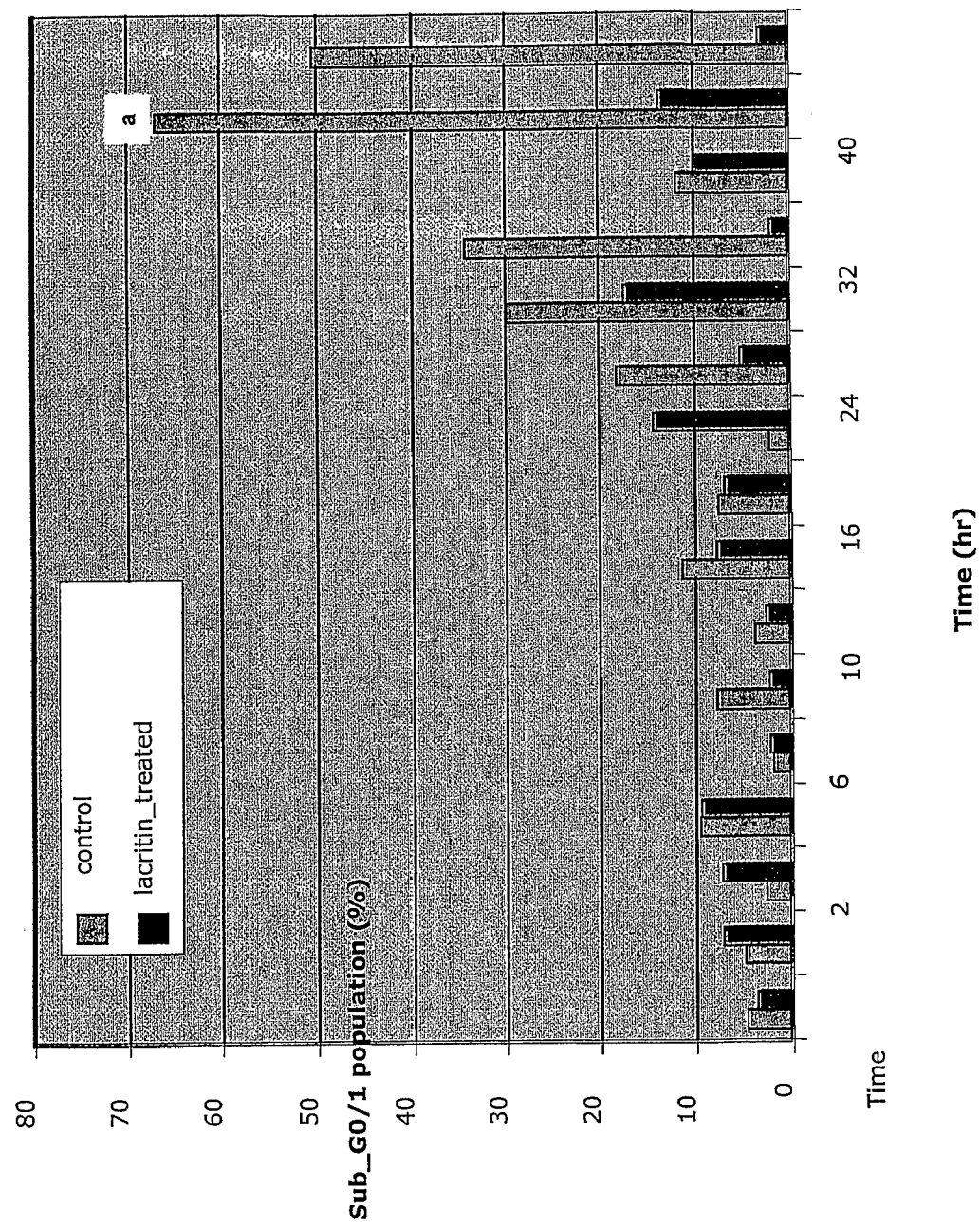
FIGS. 3A-3C represent data acquired from culturing HSG cells in vitro in a nutrient poor media, both in the presence and absence of lacritin, and demonstrates graphically protection of HSG cells by lacritin. HSG cells were cultured for different times in alpha-MEM medium, with or without lacritin (0.4 nM), then fixed with ice-old 70% ethanol and stained with propidium iodide at saturating condition, and examined by FACS.
Figure 3B:
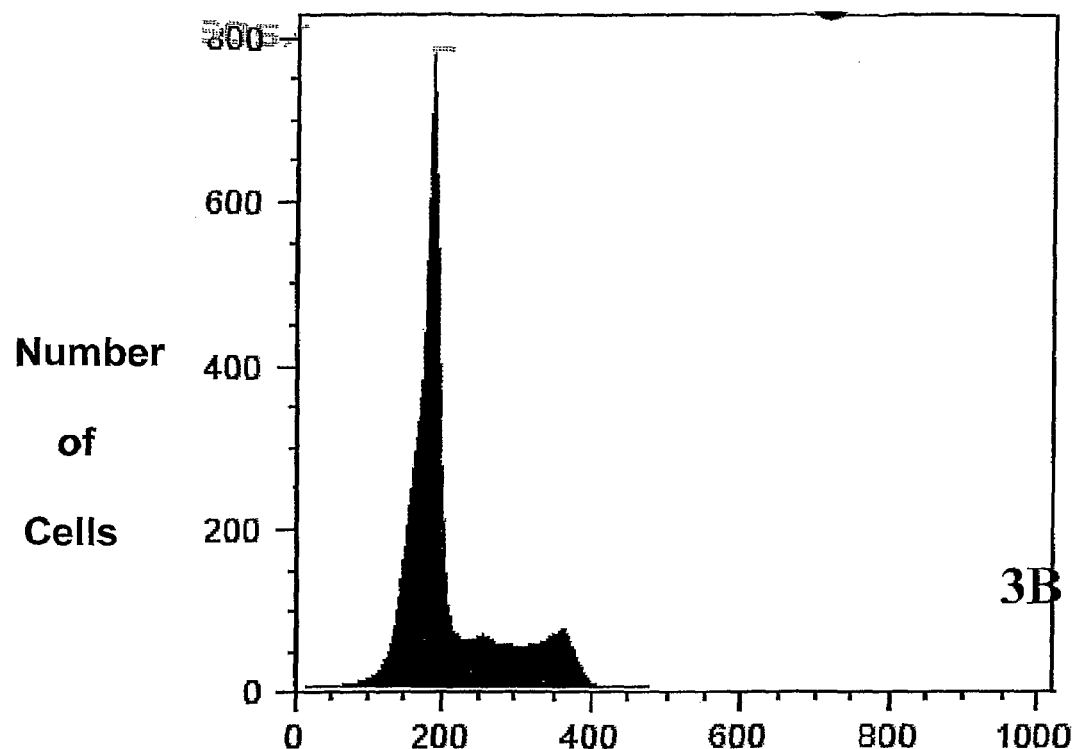
Figure 3C:
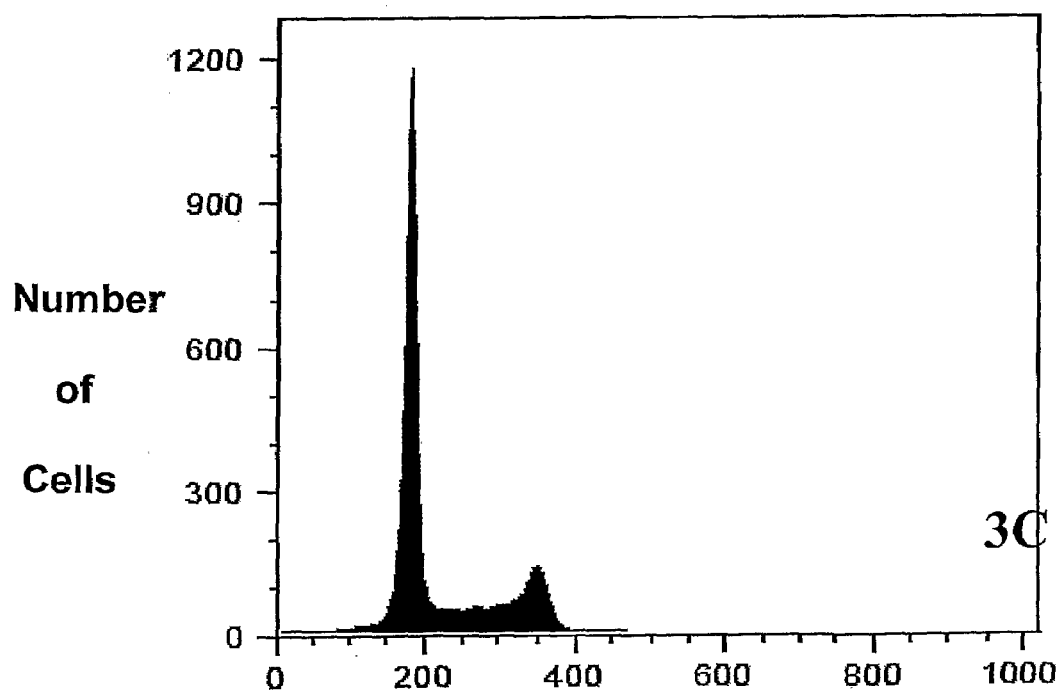

Subsequent flow cytometry (FACS) analysis was carried out to monitoring the time course of cell death and survival promotion function of lacritin. For HSG cells cultured in nutrient depleted medium (alpha mem), those cells contacted with lacritin at 10 ng/ml, demonstrated no noticeable DNA fragmentation (see FIG. 3B), whereas cells cultured in nutrient deficient media in the absence of lacritin had significant DNA degradation (see FIG. 3B). The amount of cells undergoing apoptosis, as measured by the percentage of sub G0/G1 population is shown in FIG. 3A. Lacritin protected cells from death in nutrient depleted medium (alpha MEM) up to 96 hours or longer. Cells cultured in the absence of lacritin undergo apoptosis starting at about 24 hours and over 50% cells are apoptotic after 48 hours of culture.

Figure 4:
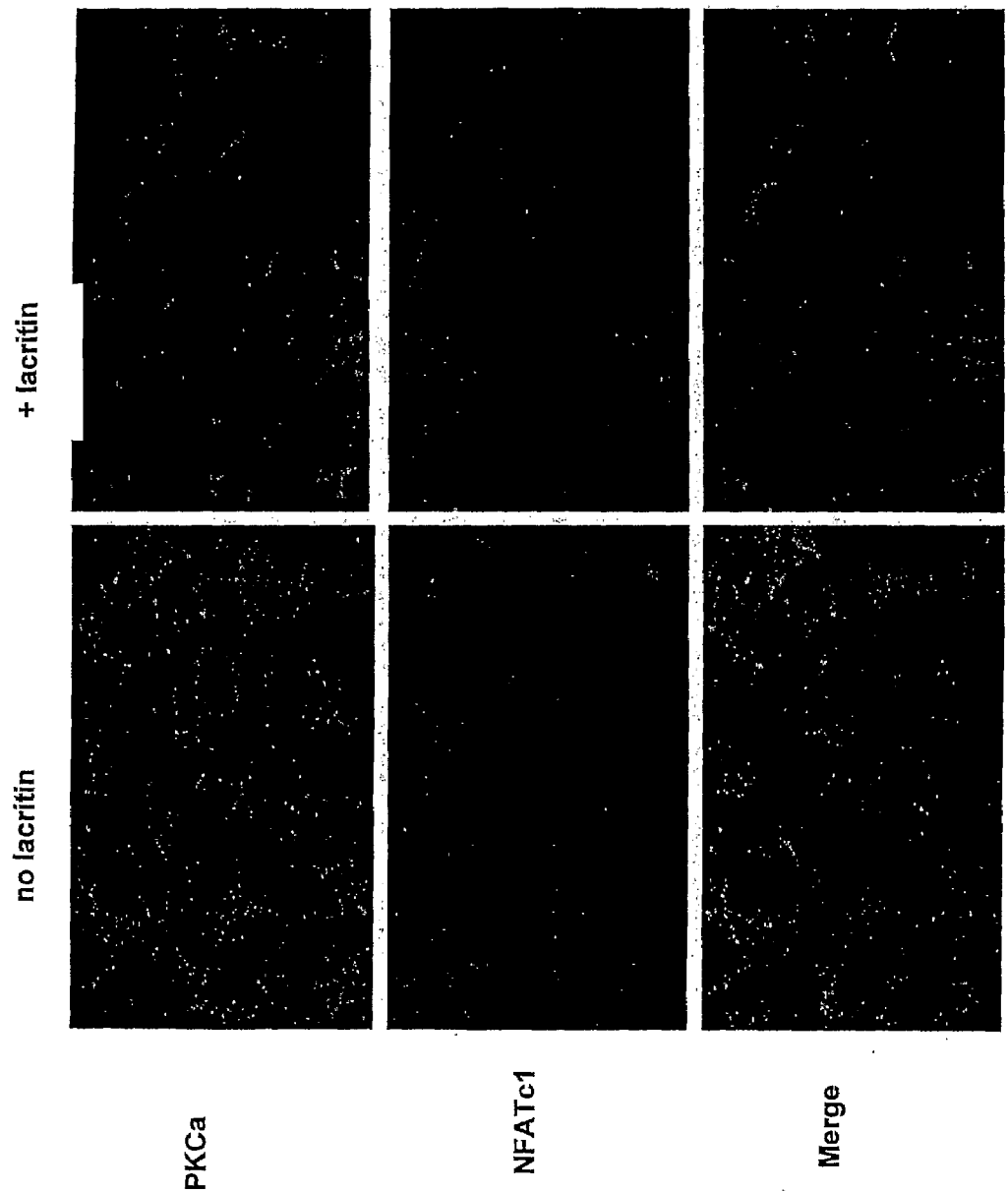
FIG. 4 represents photographs of HSG cells with or without lacritin (10 ng/ml) treatment for 1 hour and fixed and probed for PKCa and NFATc1 by immunofluorescence. PKCa was detected by a $Cy_3$-conjugated and NFATC1 by FITC-conjugated secondary antibodies from Jackson. The primary antibodies were from Santa Cruz. Without treatment, PKCa and NFATc1 co-locate in cytosol. After lacritin treatment, NFATc1 translocates to the nucleus.

In order to dissect the molecular pathways leading to the cell survival by lacritin, protein kinases and transcriptional factors were studied by Western blotting and immunofluorescence microscopy. After lacritin stimulation, conventional protein kinase C (PKC alpha) was found to move away from the cell membrane and after about 5 minutes treatment, very little PKC alpha was detected at the cell membrane by subcellular fractionation followed by Western blotting of PKC alpha. On the other hand, there were increased activities of transcriptional factors such as nuclear factor of activated T-cells (NFAT) and NF-kappaB. In FIG. 4, translocation of PKC alpha and NFAT was detected by immunofluorescence coupled with confocal microscopic imaging. In resting HSG cells (left three images), PKC alpha distributes mainly in cytosol and membrane. Similarly, NFATc1 was also found to localize largely in cytosol. Cellular co-location of PKC alpha and NFATc1 is apparent upon merging the two immunofluorescent images, as the merged cy3 and FITC labels produce distinctive yellow color. After lacritin treatment for 1 hour, PKC alpha becomes localize outside of the nuclear envelope and concentrate to one region (possibly golgi network). NFAT, on the other hand, translocates into nuclear compartment to activate gene transcription.

There has been more evidence regarding PKC alpha translocation and NFAT activation. Go6976, a specific inhibitor for PKC alpha and beta 1, has been found to abolish changes of NFAT via Western blotting study (however, there was very little or non PKC beta isoform in HSG cells). Also note that the same inhibitor was found to suppress Ca++ signaling, an early event after lacritin stimulation.

Furthermore, the active form of NF-kappaB subunit, RelA (p65) was found to be involved in the signaling. Nuclear translocation of this transcription factor has also been observed after lacritin treatment. Very little RelA was initially observed in the nuclear compartment in resting HSG cells. However, upon lacritin treatment, in as early as 1 minute, a detectable amount of RelA accumulated in the nucleus, and the concentration continued to increase and peaked between 15 minutes to 1 hour. RelA stayed in the nucleus and a high level of RelA was still observed at 4 hours after initial contact with lacritin.

EXAMPLE 5

To define the lacritin proliferative field, experiments were performed to characterize its domain and cell target specificity, optimal dose, and signaling pathways activated.

General Methods

Cell Lines

Human salivary ductal cells (HSG) were expanded in Dulbecco's modified Eagle's medium with 10% fetal calf serum (Sanghi, S., et al., J. Mol. Biol., 2001, 310:127-139), or for mitogenesis experiments in minimum essential medium Eagle's alpha modification. Also grown in Dulbecco's modified Eagle's medium with 10% fetal calf serum were mouse 3T3 fibroblasts, HS68 human foreskin fibroblasts and WM164 human melanoma cells. 293T human embryonic kidney cells were cultured in minimal essential medium with 0.1 mM non-essential amino acids, 1 mM sodium pyruvate, 10% fetal calf serum; K562 human erythroleukemia cells in Iscove's modified Dulbecco's medium with 10% fetal bovine serum; TM3 and TM4 mouse testicular Leydig and Sertoli cells, respectively in a 1:1 mixture of Ham's F12 medium with Dulbecco's modified Eagle's medium containing 10% fetal bovine serum; and U1242MG human glioblastoma and U251MG human glioma cells in minimum essential medium Eagle's alpha modification. All media was purchased from Gibco Invitrogen (Grand Island N.Y.).

Lacritin Constructs and Purification

A 363 bp region of DNA coding for intact mature lacritin without signal peptide was PCR-amplified from lacritin cDNA (Sanghi, S., et al., J. Mol. Biol., 2001, 310:127-139) and subcloned into pTYB1 (New England Biolabs; Beverly Mass.) to create the lacritin-intein fusion plasmid pLAC. The restriction enzyme site SapI was added to the forward primer (5'-GGTGGTCATATGGAAGATGCC-3') (SEQ ID NO:25) and NdeI was added to the reverse primer (5-GGTGGT-TGCTCTTCCGCATGCCCATGG-3') (SEQ ID NO:26) to facilitate subcloning, which was verified by sequencing. Deletions were based on the mature lacritin peptide, namely the peptide having SEQ ID NO:10. The new deletion fragments were named based on the number of amino acids deleted from SEQ ID NO:10 and based on whether the deletions were made at the N- or C-termini. C-terminal deletions of 5, 10, 15, 20, 25 and 59 amino acids were respectively generated using forward primer 5'-GGTGGTTGCTCTTC-CAACTATTATTACTATGAAGATGCCTCCTCT-3' (SEQ ID NO:27) and respective reverse primers 5'-GGTGGT-GAATTCTCATAGACTGAATT-3' (SEQ ID NO:28), 5'-GGTGGTGAATTCTCACAGTAATTTTTG-3' (SEQ ID NO:29), 5'-GGTGGTGAATTCTCAAAATTCACTTCC-3' (SEQ ID NO:30), 5'-GGTGGTGAATTCTCATTCGAT-GAATTC-3' (SEQ ID NO:31), 5'-GGTGGTGAATTCTCAT- TCACCTGGCA-3' (SEQ ID NO:32) and 5'-GGTGGT-GAATTCTCACTGCCTGCTTG-3' (SEQ ID NO:33). Amplicons were directionally subcloned into pTYB11 using SapI and EcoRI and insertions were verified by sequencing. Plasmids from this series were respectively designated pLAC/C-5-pLAC/C-59. Forward and reverse primers for the N-24 terminal deletion were respectively 5'-GGTGGT-TGCTCTTCCAACATCTCAGGTCCAGCAGAAC-3 (SEQ ID NO:34) and 5-GGTGGTTGCTCTTCCGCATGC-CCATGG-3' (SEQ ID NO:35) creating the plasmid pLAC/N-24.

For protein expression, cultures of E. coli strain ER2566 harboring the plasmid of interest were grown at 37° C. to mid-log and the temperature reduced to 23° C. to minimize secretion in inclusion bodies prior to induction. The cultures were induced with 0.5 mM isopropyl-beta-D-thiogalactopy-ranoside (IPTG) for 4 h at 23° C. Cells were harvested by centrifugation and stored at −70° C. Frozen cell pellets were thawed at room temperature, lysed by sonication in 50 mM Tris (pH 8), 0.5 M NaCl, 0.45% Triton X-100 and centrifuged. The cleared supernatant was loaded onto a chitin column (IMPACT-CN System; New England Biolabs Inc., Beverly Mass.) equilibrated with 10 column volumes of 50 mM Tris (pH 8), 0.5 M NaCl and washed with twenty column volumes of the same buffer. On-column cleavage of lacritin from C-terminal intein was accomplished by incubation for 16 h at room temperature with 50 mM dithiothreitol in the same buffer. Eluates were concentrated, dialyzed extensively against PBS (4° C.), quantitated, and assessed. pLAC lacritin activity was identical to lacritin prepared from a pET28b construct (Sanghi, S., et al., J. Mol. Biol., 2001, 310:127-139), the latter of which included the signal peptide. SDS PAGE mobility of lacritin from pLAC is 18 kDa (12.3 kDa predicted), and 23 kDa from pET28b (18.4 kDa predicted with H is tag; previously indicated in error as greater in Sanghi, S., et al., J. Mol. Biol., 2001, 310:127-139). Mass spectrometry sequencing and immunoblotting confirmed protein identity; and LAL assays (Charles River Endosafe, Charlston S.C.) eliminated contaminating endotoxin as a source of signaling activity. Circular dichroism analysis was performed in an AVIV 215 spectropolarimeter running Igor Pro numerical analysis software (Proterion, Piscataway N.J.).

Phosphotyrosine Blotting and Mitogenesis

For phosphotyrosine blotting and mitogenesis assays, cells in serum-containing media were seeded overnight in 24-well plates at a density of $0.5 \times 10^5$ cells/mm$^2$ corresponding to 20-30% confluency after cell attachment, incubated in serum-free media without supplements for 24 h (phosphotyrosine) or washed with serum-free media without supplements three times (mitogenesis) and incubated with lacritin (1-1000 nM), or positive controls EGF (1.6 nM) and 10% fetal bovine serum, or negative controls bovine serum albumin or no additive in serum-free media without supplements for the indicated times (phosphotyrosine) or 30 h (mitogenesis). For phosphotyrosine assays, cells were extracted in 1% NP40 containing sodium vanadate (2 mg/ml), DTT (5 mg/ml), protease inhibitors, 50 mM HEPES, 100 mM NaCl, and 2 mM EDTA; then separated by 10% SDS PAGE, transferred and blotted. The following antibodies (Cell Signaling Technology, Beverly Mass.) were tested: antiphosphotyrosine antibody (P-Tyr-100), anti-phospho-PKC$\overline{\alpha\beta}_{II}$, anti-PKC$\alpha$, anti-phospho-PKC$\delta$, anti-phospho-PKC (pan), anti-p44/42 MAPK, anti-phospho-Raf, anti-phospho-SAPK/JNK, anti-phospho-p38 Map kinase, anti-phospho-Raf, anti-phospho-Akt, anti-phospho-CaMKII, anti-phospho-MARCKS, or anti-tubulin (loading control). After washing, bound antibodies were detected with peroxidase-labeled secondary antibody and ECL. With the exception of at least nine proteins in the P-Tyr-100 blot (FIG. 1), none of the effectors tested above appeared to be phospho-activated during lacritin signaling (not shown). For mitogenesis (Hussaini et al., '00), [$^3$H]-thymidine (2 mCi/ml) was added for the next 6 h. Incorporation was stopped with ice-cold phosphate buffered saline and followed by addition of cold and then room temperature trichloracetic acid (10%) for 10 min each, washing of cells with phosphate buffered saline, solubilization with 1 N sodium hydroxide, neutralization with 1 N hydrochloric acid, addition of scintillation fluid and then quantitation in a scintillation counter. To deplete PKC$\alpha$ in HSG cells, a pool of four PKC$\alpha$-specific siRNAs (100 nM) were transfected via LipofectAMINE 2000 in Opti-MEMI Reduced Serum Medium (Invitrogen, Grand Island N.Y.) without serum and antibiotics according to manufacturer's instructions. Each of the four siRNAs was also individually transfected. In negative controls, cells were transfected with a pool of four lamin-specific siRNAs (Upstate LLC, Charlottesville Va.; Dharmacon Inc, Lafayette Colo.). Seventy-two hours post-transfection, mitogenesis was assessed by co-addition of 10 n4 lacritin and [$^3$H]-thymidine (2 mCi/ml) (Amersham, Piscataway N.J.) for 24 hrs. PKC$\alpha$ depletion was confirmed by Western blotting.

Calcium and Translocation Imaging

Cells were seeded at $1.4 \times 10^4$ HSG cells/mm$^2$ or $0.7 \times 10^4$ HSG cells/mm$^2$ on Matrigel-coated (100 µg/ml; BD Biosciences; San Diego Calif.) coverslips to respectively achieve 70-80% confluency after overnight or 48 h growth in 6-well plates containing phenol red-free Dulbecco's modified Eagle's medium with 10% fetal calf serum. Cells were washed repeatedly in calcium-free/phenol red-free Hanks basic salt solution with 20 mM N-2-hydroxyethylpiperazine-N'-2-ethane sulfonic acid (Gibco Invitrogen; Grand Island N.Y.) and then incubated for 10 min in the same solution containing 1 µM U73122, 1 µM U73343 (inactive analogue of U73122; BIOMOL Research Labs, Plymouth Meeting Pa.), 1 µM Go 6976, or 10 µM nifedipine (Calbiochem; San Diego, Calif.); or for control in vehicle (DMSO/Pluronic diluted to same level in inhibitor solution) alone.

Other cells were incubated ($0.7 \times 10^4$ HSG cells/mm$^2$ overnight plating) with 100 ng/ml pertussis toxin (Calbiochem; San Diego Calif.) in phenol red-free Dulbecco's modified Eagle's medium with 10% fetal calf serum; or vehicle alone). Cells were washed with calcium-free/phenol red-free Hanks basic salt solution, 20 mM N-2-hydroxyethylpiperazine-N'-2-ethane sulfonic acid and then incubated for 1 h at room temperature with the same solution containing fluo-4 µM at 4 µM (FluoroPure grade [Molecular Probes; Eugene Oreg.] dissolved in DMSO plus 20% Pluronic F-127). Cells were washed three times for 60 min at room temperature with calcium-free/phenol red-free Hanks basic salt solution with 5 mM Ca$^{2+}$ or 5 mM EGTA. Temperature was stabilized for 5 min at 37° C. coverslips were placed on the stage of a TE-200 epifluorescent microscope (Bio-Rad Radiance2100 confocal/multiphoton system using Plan Fluor 60×NA 1.4 Oil IR objective lens [Bio-Rad, Hercules Calif.] as part of the W. M. Keck Center for Cellular Imaging, University of Virginia), subjected to a 488 nm argon laser light source with emission at 528 nm. Baseline monitoring was followed by addition of lacritin or deletion fragments in phenol red-free Hanks basic salt solution.

Images were acquired at 2-3 s intervals using Laser-Sharp2000 software (Bio-Rad) and store on disc for later analysis. For translocation assays, HSG cells on Matrigel-coated coverslips with or without inhibitors were treated with 10 nM lacritin or positive control 200 nM phorbol 12-myristate 13-acetate, or vehicle for 15 min, then washed with phosphate-buffered saline, formaldehyde-fixed, blocked with phosphate-buffered saline containing 1% bovine serum albumin and 10% goat serum, incubated with anti-PKCα (C-20) or anti-NFATC1 (mab 7A6) (both from Santa Cruz Biotechnology Inc.; Santa Cruz, Calif.) followed by secondary Cy3-, FITC- or Alexa488-labeled antibodies and confocal microscopic visualization (Bio-Rad Radiance2100).

Results

Lacritin is a Highly Cell Selective Epithelial Mitogen

We first sought to characterize lacritin's dose and cellular specificity. Lacritin flows over persistent glandular epithelia of acini and ducts to later become deposited on the surface of the eye or mouth (FIG. 5A). Using a $^3$H-thymidine uptake assay we find that the human salivary ductal (HSG) cell response to lacritin is bell-shaped. The optimal dose of 1 or 10 nM promotes a level of proliferation matching the FBS positive control (FIG. 5B). This biphasic response and dosage is equivalent to that seen for sonic hedgehog, VEGF, FGF and PDGF in other cell systems (Rankin, S., et al., J. Biol. Chem., 1994, 269:704-710; Rubin, J. B., et al., Development, 2002, 129:2223-2232; Williams, E. J., et al., Development, 1994, 120:1685-1693; Sondell, M., et al., J. Neurosci., 1999, 19:5731-5740; Chang, C. P., et al., Cell, 2004, 118:649-663). Few other cell types are targeted by lacritin. Lacritin is mitogenic for human corneal epithelial (HCE) and embryonic kidney (HEK) cells (FIG. 5B) which both display a similar bell-shaped response (not shown). Lacritin is not mitogenic for human epidermal (A431), cervical (HeLa), foreskin fibroblast (HS68), fibrosarcoma (HT1080), erythroleukemia (K-562), non-invasive breast carcinoma (MCF7), melanoma (SK-MEL, WM-164), Leydig (TM4), Sertoli (TM3), and mouse fibroblast (NIH/3T3) cells (FIG. 5B); nor human glioma (U-1242-MG; U-251-MG) cells even at higher doses (not shown). Lacritin targeting is rapid. Signaling is apparent within the first minute by differential and transient tyrosine phosphorylation of at least nine different unidentified phosphoproteins (FIG. 5C) in an equivalent dose responsive manner (not shown). Within two hours 3H-thymidine uptake in HSG cells is detectable (not shown). Importantly, we find no activation of p42 and p44 MAPK (MAPK1 and MAPK3, respectively; FIG. 5D), thereby excluding the possibility that lacritin-dependent mitogenesis involves transactivation of the EGF pathway, or of another Ras-GTP-dependent cytokine or growth factor pathway. These results reveal that lacritin is an epithelial-selective mitogen. Yet only certain epithelia are responsive and include cells derived from both persistent (HSG, HEK) and rapidly renewing (HCE) epithelia. Other cells from both categories are excluded. Restricted release by certain glandular persistent epithelia for mitogenic targeting of equally exclusive (mainly downstream) epithelia defines an unusual niche (FIG. 5A).

Lacritin's C-Terminus Drives Epithelial-Restricted Mitogenesis

Figure 6A:
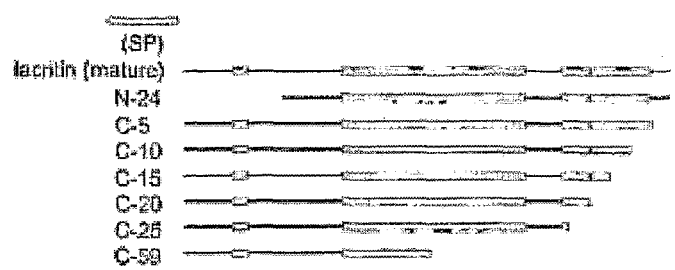
FIG. 6A schematically depicts mature lacritin versus N- and C-terminal deletion constructs. Boxed are PSIPRED-predicted alpha helices.
Figure 6B:
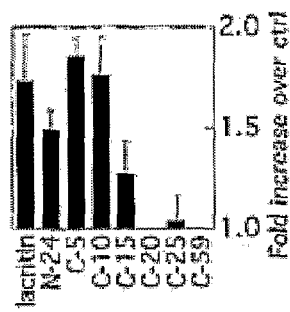
FIG. 6B graphically represents the results of tests of fragments/deletion constructs N-24 (SEQ ID NO:16), C-5 (SEQ ID NO:17) and C-10 (SEQ ID NO:18), indicating that they are active. C-15 (SEQ ID NO:19) is partially active. C-20 (SEQ ID NO:20), C-25 (SEQ ID NO:21) and C-59 (SEQ ID NO:22) are inactive. Concentration of lacritin and lacritin deletion constructs is 10 nM in this and subsequent figures.
Figure 6C:
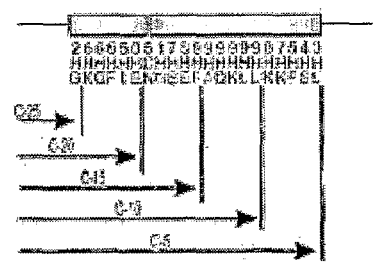
FIG. 6C schematically summarizes some of the fragments tested. The C-15/C-30 breakpoint suggests that the proximal two-thirds of the more distal of two predicted C-terminal alpha helices is essential for mitogenesis. A predicted N-linked glycosylation site (NGS) bounds the N-terminus of the distal helix. PSIPRED confidence numbers for an alpha helix (H) or random coil (C) are indicated.
Figure 6D:
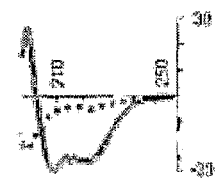
FIG. 6D depicts the results of a circular dichroism analysis of the active region in either PBS or in 10 mM dodecylphosphocholine. The active region, KQFIENGSEFAQKLLKKFS (SEQ ID NO:23) forms a random coil in PBS (solid) and an alpha helix in 10 mM dodecylphosphocholine, as examined by circular dichroism.
Figure 6E:
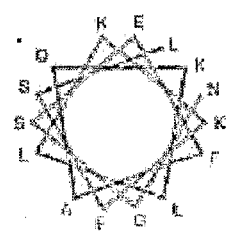
FIG. 6E schematically illustrates a Helical Wheel analysis. The C-terminal alpha helix (NGSEFAQKLLKKFS) (SEQ ID NO:24) therefore likely presents the hydrophobic binding face 'AFGL', as predicted by 'Helical Wheel'.

Our approach towards a molecular appreciation of this activity began by studying sequence alignments. Lacritin's limited homology to non-mitogenic fibulin-2 or chondroitin sulfate proteoglycan 5 was not informative. Of potential utility however, was mitogen and putative homologue dermcidin (Porter, D., et al., Proc. Natl. Acad. Sci. USA, 2003, 100: 10931-10936). Since the identity of mature lacritin and dermcidin was only 23%, we compared both by near optimal alignment and identified three homologous regions in the carboxy terminal half that were not apparent or were only partially apparent in the published alignment (Porter, D., et al., Proc. Natl. Acad. Sci. USA, 2003, 100:10931-10936). Two reside in alpha helices predicted by PSIRED (Protein Structure Prediction Server; FIG. 6). Since neither protein had been subjected to deletion analysis, we generated an array of lacritin C-terminal truncation mutants (FIG. 6A). One N-terminal mutant, N-24, was also prepared by deleting the amino terminal 24 amino acids of SEQ ID NO:4 (native lacritin). Each was purified and compared to intact lacritin in mitogenic dose response experiments using HSG cells. Mutants lacking five and ten amino acids from the C-terminus, or twenty-four amino acids from the N-terminus, were fully active. Removal of five or ten more C-terminal amino acids (C-15, C-20) respectively diminished or completely abrogated activity (FIG. 6B, shown at 10 nM), a pattern mirrored by loss of binding to the core protein of putative lacritin coreceptor syndecan-1 (not shown). Thus, the ten additional C-terminal amino acids deleted from C-10 (amino acids 100-109 of mature lacritin; FIG. 6C) are key for both activities. This region resides within a PSIRED-predicted alpha helix. To determine whether it is capable of alpha helical formation, we synthesized the active region KQFIE NGSEFAQKLLKKFS (SEQ ID NO:23) with several flanking amino acids and subjected it to circular dichroism. In PBS it formed a random coil, and in 10 mM dodecylphosphocholine an alpha helix (FIG. 6D). Although plasma membrane insertion is not in keeping with lacritin's low nanomolar activity and cell specificity, hydrophobic surfaces on the same or different proteins can create an environment appropriate for alpha helical formation (Murre, C., et al., Cell, 1989, 58:537-544). To study the hydrophobic nature of this region and whether a hydrophobic surface would be generated by alpha helical formation, we utilized 'Helical Wheel'. Five of ten residues in the active region are hydrophobic, and all group along one face. Inclusion of flanking amino acids further accentuates (FIG. 6E) the polarized nature of this structure, which is known as an amphipathic alpha helix. Amphipathic alpha helices are common in ligand-receptor or ligand-ligand interactions. The hydrophobic face of parathyroid hormone-like hormone's C-terminal amphipathic alpha helix, for example, mediates binding of parathyroid hormone-like hormone receptor-1 (Barden, J. A., et al., J. Biol. Chem., 1997, 272:29572-29578). The same mechanism directs VEGF dimerization as a prerequisite for FLT1 and KDR receptor binding (Siemeister, G., et al., J. Biol. Chem., 1998, 273:11115-11120). We suggest that this is also true for lacritin in which lacritin's C-terminal mitogenic domain is formed by development of a C-terminal alpha helical structure with a hydrophobic binding face. Helical wheel analysis of the corresponding dermcidin peptide (not shown) suggests an equally strong amphipathic helix and hydrophobic binding face (VGVLAV) (SEQ ID NO:36) distinct from lacritin (LAFGLF) (SEQ ID NO:37).

Distinctive Lacritin Mitogenic Signaling Through PKCα

Could such epithelial cell targeting be mirrored by a mitogenic signaling pathway with distinctive features? We demonstrated earlier that lacritin-targeted human corneal epithelial cells rapidly mobilize intracellular calcium (Sanghi et al., '01); and in HSG cells tyrosine phosphorylation of at least nine unidentified proteins follows within a minute of lacritin addition (FIG. 5C). Excluded was p42 and p44 activation (FIG. 5D) indicating that lacritin mitogenic signaling was distinct from the Ras-GTP-dependent pathway common to many growth factors and cytokines. Although we found that lacritin binds syndecan-1, historically syndecan-1 has served as a co-receptor, for its demonstrated signaling properties are limited. We were attracted by the rapidity (20-30 sec) of lacritin-dependent calcium mobilization in human corneal epithelial cells as an assay for upstream effectors. However, these cells are less readily transfectable than HSG cells for RNAi studies. We therefore asked whether HSG cells similarly respond, and if so is calcium mobilization likely associated with mitogenesis.

Figure 7A:
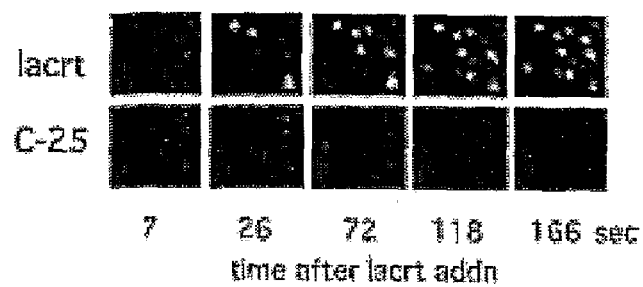
FIG. 7A, represents images of mobilization of intracellular calcium 20-30 seconds after lacritin addition (lacrt), but not after addition of the construct C-25 (SEQ ID NO:21) (calcium-containing medium for this and subsequent figures unless indicated otherwise).
Figure 7B:
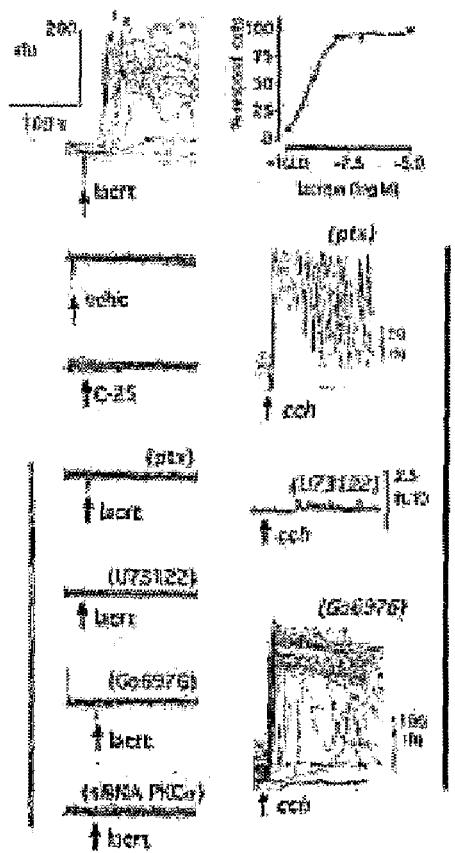
FIG. 7B, graphically illustrates calcium fluorescence tracings after addition (arrow) of lacritin, C-25, vehicle (vehic) or positive control carbachol (cch), in the absence or presence of inhibitors. Calcium mobilization in response to lacritin is observed in most cells per field at 1 or 10 nM and is suppressed by pretreatment with pertussis toxin (ptx), PLC inhibitor U73122, PKC inhibitor Go 6976, or by siRNA depletion of PKCα. Carbachol dependent mobilization is unaffected by pertussis toxin or Go6976, as noted previously by others.

Loading HSG cells with the calcium indicator Fluo-4 revealed that the mitogenic dose of lacritin (10 nM), but not 10 nM of non-mitogenic C-25 deletion mutant, promotes calcium mobilization usually within 30 sec of addition. Free calcium is both nuclear and cytoplasmic (FIG. 7A). Since no other information was available on mitogenic signaling, we next applied several common pharmacological inhibitors. Preincubation with pertussis toxin (100 ng/ml) completely inhibited lacritin-stimulated calcium mobilization, indicating an upstream requirement for active G proteins $G\alpha_i$ or $G\alpha_o$. As a positive control, we replaced lacritin with muscarinic agonist carbachol and observed full calcium mobilization (FIG. 7B). Carbachol's $G\alpha_q$-mediated calcium mobilization is well known to be insensitive to pertussis toxin. Aminosteroid U73122 inhibits G protein-mediated activation of phospholipase C (PLC) that in turn catalyzes the formation of IP3 and diacylglycerol. U73122 (1 µM) inhibited calcium mobilization by both lacritin and carbachol (FIG. 3B), suggesting that PLC-generated IP3 directs calcium release from intracellular stores. Diacylglycerol activates downstream protein kinase C(PKC). Yet when cells were preincubated with the PKC inhibitor Go 6976 (1 µM), lacritin-stimulated calcium mobilization was completely inhibited (FIG. 7B) suggesting an unusual upstream requirement for active protein kinase C(PKC). PKC is downstream of calcium after carbachol stimulation of acinar and other cells. To confirm that the same is true of HSG cells, we carbachol-stimulated Go 6976-preincubated cells. Calcium mobilization was unaffected (FIG. 3B) even at 10 µM Go 6976 (not shown). Lacritin signaling therefore displays distinctive features.

Davies, S. P., et al., Biochem. J., 2000, 351:95-105 have demonstrated that specificities of protein kinase inhibitors are less narrow than initially thought. Although Go 6976 is the most selective of PKC inhibitors, in vitro assays reveal the capacity to inhibit elements of the MAPK (MKK1, MAP-KAP-K1b), ERK/p38 (MSK1), Rho (ROCK), and Akt (S6K1) pathways, as well as GSK3B downstream of Gaq (Davies, S. P., et al., Biochem. J., 2000, 351:95-105). We therefore sought an alternative approach to test the involvement of PKC in lacritin signaling and mitogenesis.

Figure 8:
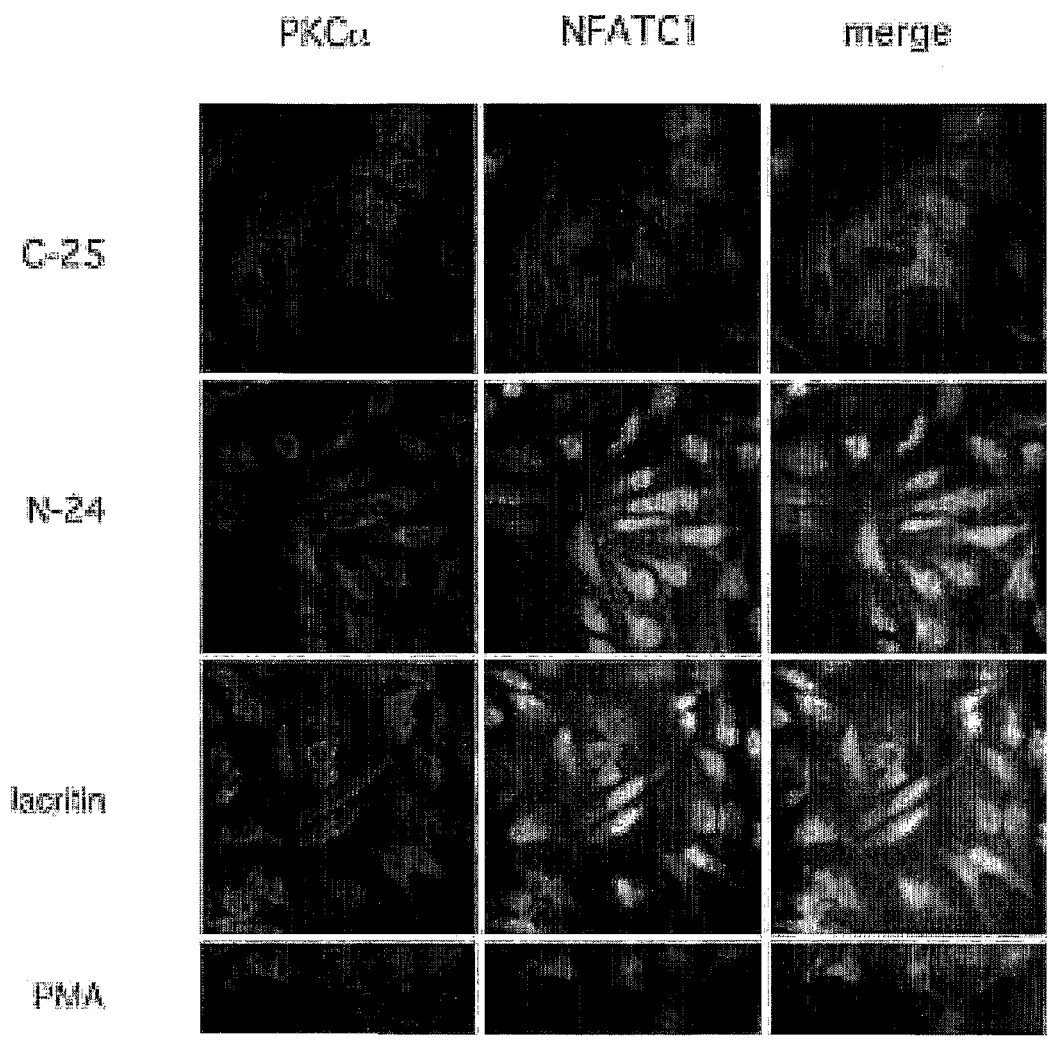
FIG. 8, represents photographic images of cells indicating that PKCα translocates to the perinuclear golgi region and NFATC1 to the nucleus in a lacritin C-terminal dependent manner. Upper row of images of photographs indicates use of C-25 (SEQ ID NO:21); Second row indicates use of N-24 (SEQ ID NO:16); Third row indicates use of lacritin; Fourth (bottom) row indicates plasma membrane translocation with positive control phorbol 12-myristate 13-acetate. The left column indicates PKCα, the middle column indicates NFATC1, and the right column indicates merge.

HSG cells are known to express PKCα, δ, ε, γ, ι, and λ (Jung, D. W., et al., J. Cell Physiol., 2000, 185:215-225), of which only the α isoform should be inhibited by Go 6976 at 1 µM. We chose to target PKCα mRNA for degradation by RNA interference (FIGS. 8 A and B). HSG cells were transfected with a pool of four small interfering RNAs for PKCα. PKCα became depleted and transfected cells failed to proliferate in response to lacritin. Serum-triggered mitogenesis was slightly reduced ('D7-D10') in comparison to mock and negative controls. Cells were then individually transfected with each of the four small interfering RNAs. Both PKCα D7 and D10 transfectants were lacritin unresponsive, but completely serum responsive in proliferation assays (FIG. 8A). Importantly, further testing of D7 revealed no lacritin-dependent calcium mobilization (FIG. 7B). Calcium tracings from cells stimulated with lacritin in calcium-containing medium (FIG. 7B) are in keeping with rapid intracellular store release followed by extracellular calcium entry via store-operated channels. Equally plausible is that lacritin treatment directly activates receptor-operated channels on the plasma membrane.

Figure 7C:
FIG. 7C, graphically illustrates calcium mobilization in calcium-free medium with EGTA.
Figure 7D:
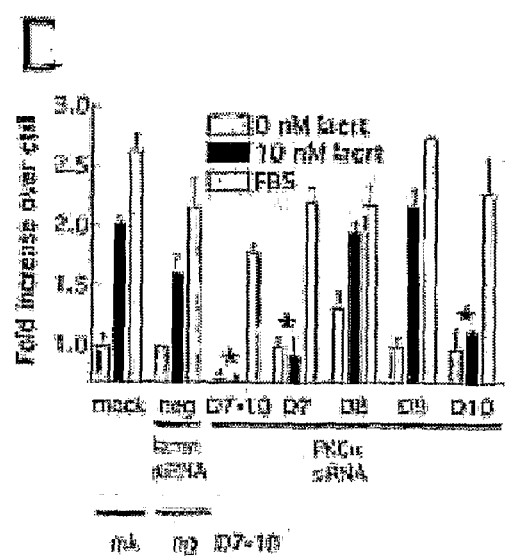
FIG. 7D, is a graphic representation of the results of experiments showing siRNA depletion of PKCα eliminates lacritin's mitogenic response, as observed with pooled siRNAs D7-10, and D7 and D10 applied individually. Little or no effect on FBS-stimulated mitogenesis, nor of negative control lamin A/C siRNA, is observed. PKCα blot illustrates protein depletion with D7-10, but not in mock (mk) transfected nor lamin A/C siRNA transfected cells (ng).

To ask whether mobilized calcium derives from extracellular or intracellular sources or both, cells were stimulated with 10 nM lacritin in EGTA-containing or nominally calcium-free medium. Cells in EGTA-containing medium mobilized internal calcium in response to lacritin (FIG. 7C), and cells in nominally calcium-free medium proliferated in a bell-shaped lacritin dose-dependent manner (FIG. 5B, inset). Without wishing to be bound by any particular theory, it appears that calcium mobilization is initiated internally, and extracellular calcium is not necessary for mitogenesis.

Lacritin Stimulates Translocation of PKCα to the Perinuclear Golgi Region

PKCα regulation of cell proliferation is initiated by translocation of cytoplasmic PKCα to membranes. Interaction of membrane-associated PKCα with other membrane-associated effectors drives downstream signaling to mitogenesis. It was therefore determined herein whether lacritin promotes PKCα translocation, and if so to which membrane compartment.

We imaged PKCα in cells 15 min after treatment (FIG. 8). Nonmitogenic construct/fragment C-25 (10 nM) had no effect, leaving PKCa diffusely distributed throughout the cytoplasm. In contrast, 10 µM lacritin or the N-24 construct/fragment shifted PKCα primarily to the perinuclear Golgi region (FIG. 8C). Cells treated with positive control 4β-phorbol 12-myristate 13-acetate concentrated PKCα solely in the plasma membrane (FIG. 8C). The phosphorylation state of PKCα influences its translocation site. Hyperphosphorylated PKCα becomes associated with the plasma membrane whereas hypophosphorylated or dephosphorylated PKCα is known to translocate to the perinuclear Golgi region. To determine if the latter is true and if so over what time course, we treated cells with lacritin, N-24 and C-25, and then blotted cell lysates for phospho-PKCα (FIG. 8B). 10 nM lacritin promotes PKCα dephosphorylation within 1 min of addition. This form is sustained for at least 15 min, but by 30 min has returned to baseline phosphorylation. Dephosphorylation triggered by increasing molar levels of lacritin or N-24 mirrored the proliferation response with optimal dephosphorylation at 10 nM. Non-mitogenic C-25 had no effect, whereas positive control 4β-phorbol 12-myristate 13-acetate-promoted hyperphosphorylation.

Figure 9A:
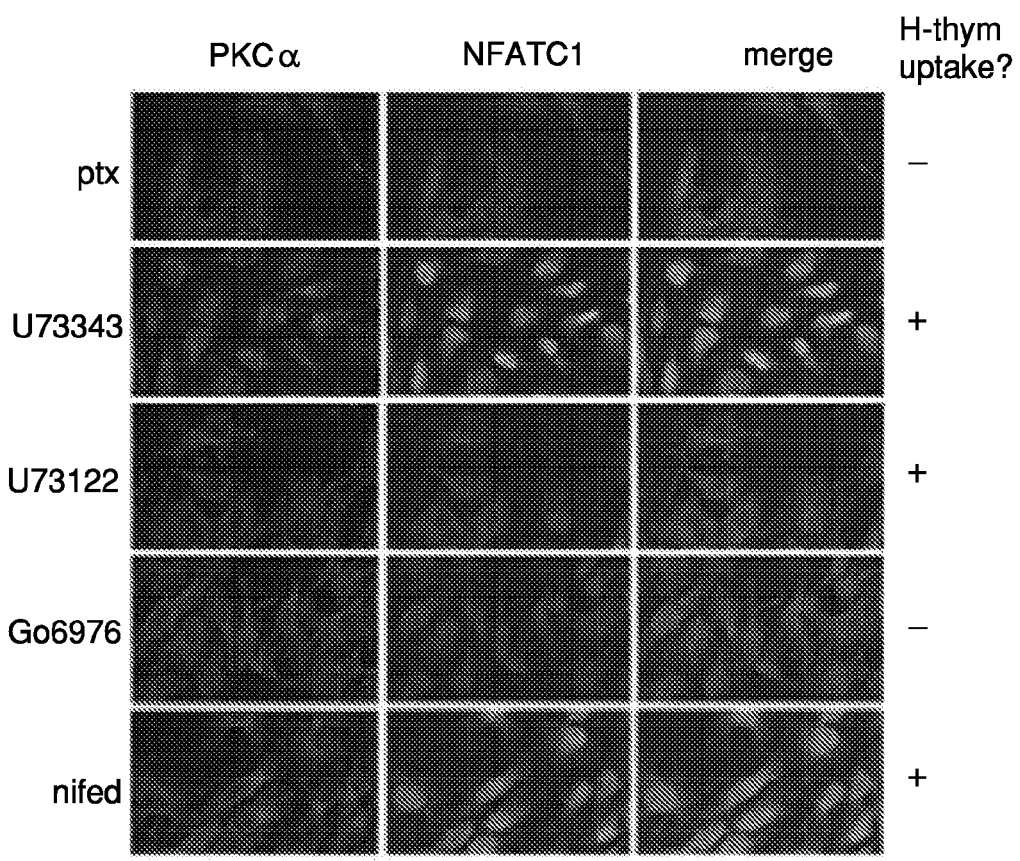
FIG. 9A represents photographic images demonstrating that lacritin dependent translocation of PKCα (left/first column) and NFATC1 (middle/second column) is inhibited by pertussis toxin (upper/first row), U73122 (third row) and Go6976 (fourth row); but not by inactive U73122 analogue U73343 (second row), nor by L-channel calcium blocker nifedipine (nifed) (bottom/fourth row). The third column represents merge. The far right (fourth) column indicates the effect of the compounds on tritiated thymidine uptake, as indicated with a "+" or "−".
Figure 9B:
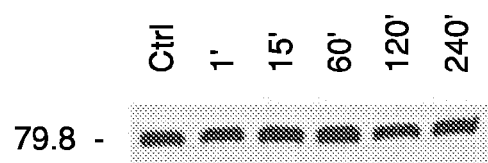
FIG. 9B depicts an image of a phosphorylation analysis of PKC upon lacritin addition.

Nuclear calcium mobilization may therefore be a direct spatiotemporal consequence of PKCα perinuclear Golgi translocation via local generation of $IP_3$. Indeed, lacritin-dependent nuclear and cytoplasmic calcium mobilization is eliminated by siRNA depletion of PKCα (FIG. 7B). It is suggested herein that lacritin-stimulated signaling towards calcium mobilization follows a Gai or $G\alpha_o$/PKCα/PLC pathway. If so, pertussis toxin and Go 6976, but not U73122 should inhibit PKCα translocation. We retested each and observed that lacritin-dependent PKCα translocation and dephosphorylation were inhibited by pertussis toxin (100 ng/ml) and Go 6976 (1 µM), but also by U73122 (1 µM; FIG. 9). Weakly active analogue U73343 is often used as a negative control for U73122. Cells preincubated with U73343 (1 µM) displayed full translocation and dephosphorylation (FIG. 9). This implies that an interdependent complex of PKCα and PLC is intermediate between $G\alpha_i$ or $G\alpha_o$ activation and PKCα translocation. An alternative possibility is that a PLC isomer is stationed in the perinuclear Golgi region and when active serves to capture translocating PKCα. PLCγ2 is concentrated in the perinuclear Golgi region in mast cells before and after antigen stimulation. Is PLCγ2 or another PLC isomer located in the perinuclear Golgi region of HSG cells and if so does it complex with PKCα? We immunoprecipitated endogenous PKCα from lacritin-treated cells and then blotted for phospho-PLCγ2 (FIG. 9).

Downstream Activation of PLD

We measured endogenous PLD activity after lacritin addition and obtained a bell-shaped activation curve that was optimal at 10 nM lacritin, thus recapitulating the same dose dependency observed for mitogenesis, PKCα translocation and PKCα dephosphorylation. To determine whether PKCα was upstream of PLD in lacritin signaling, cells were transfected with D7 siRNA. Depletion of PKCα completely abrogated PLD activation in response to lacritin, whereas PLD activation by serum was unaffected (FIG. 9D). Transiently hypophosphorylated perinuclear Golgi PKCα appears to have at least two roles. It complexes with PLCγ2 leading to IP3 generation and calcium mobilization. It also activates PLD1.

Converging Downstream Signals

Downstream lacritin signaling towards cell cycle progression may follow at least two different pathways. The prominence of calcium mobilization raises the possibility that cytoplasmic calcium may stimulate the phosphatase calcineurin to activate cytoplasmic NFAT (nuclear factor of activated T cells). Dephosphorylated NFAT translocates into the nucleus where it binds DNA in an obligatory cooperative interaction with other transcription factors including Fos, Jun, GATA and C/EBP (Crabtree, G. R., et al., Cell, 2002, 109 Suppl:S67-79; Yellaturu, C. R., et al., Biochem. J., 2002, 368:183-190). Second, since lacritin signaling activates PLD1 (FIG. 5D) and active PLD 1 generates phosphatidic acid, it is possible that lacritin signals to the mitogenic phosphatidic acid/mTOR/p70 S6 kinase 1 pathway (Fang et al., '03). Hypothetically, both pathways could be additively required for lacritin mitogenesis, as per parallel ERK and MTOR mitogenic signaling in response to FGF-9. Alternatively one may modulate the other, as per PI(3)K/Akt inhibition of calcineurin in muscle IGF-1 signaling (Rommel et al., '01). Since NFAT in lacrimal, salivary gland or corneal epithelia has not previously been studied, we chose to examine NFATC1, the only NFAT isomer selectively upregulated in the proliferative compartment of skin epithelium (Tumbar et al., '04). In untreated HSG and downstream corneal epithelial cells, NFATC1 is diffusely distributed throughout the cytoplasm. When lacritin or N-24 are added, NFATC1 translocates into the nucleus. C-25 had no effect. Translocation was inhibited by pertussis toxin, U73122, Go 6976 and by siRNA for PKCa, but not negative control U73343. Cyclosporine, which inhibits calcineurin activation upstream of NFAT translocation was also tested. Cyclosporine (1 μM) inhibited translocation of NFATC1 but not PKCα. These data suggest that lacritin-induced NFATC1 translocation is downstream of $G\alpha_i$ or $G\alpha_o$/PKCα-PLC/Ca/calcineurin.

Relative levels of nuclear NFATC1 conformed to the lacritin bell-shaped response seen earlier, but the source of activating calcium was uncertain. Cells in EGTA-containing medium displayed a lacritin transient (FIG. 7A) indicating that calcium mobilization is initiated from internal stores. Yet, NFAT activation has historically been associated with sustained calcium entry through plasma membrane ion channels (often L-type or TRP). Activation after channel inhibition was examined next. Blocking L-type channels with nifedipine (10 μM) did not interfere with lacritin-dependent translocation of NFATC1, PKCα (FIG. 9A), or mitogenesis. Also non-inhibitory were EGTA; and the lanthamide gadolinium ($Gd^{3+}$), a selective inhibitor of capacitative calcium entry. In contrast, thapsigargin inhibited both NFATC1 and PKCα translocation. Thapsigargin causes passive depletion of calcium from intracellular stores, the likely initial calcium source in lacritin-dependent mobilization. Without wishing to be bound by any particular theory, it is hypothesized that internal calcium activates the NFATC1 pathway in lacritin-stimulated HSG cells as part of a $G\alpha_i$ or $G\alpha_o$/PKCα-PLC/Ca/calcineurin pathway.

Recently it was demonstrated that phosphatidic acid generated by active PLD1 activates the rapamycin-sensitive mTOR/pS6K1 pathway. mTOR/pS6K1 regulates mitogenicity and cell growth by promoting protein translation necessary for G1 cell cycle transition (Lane et al., '93). To determine whether lacritin signaling activates S6K1, assays for phosphorylated S6K1 after treatment with different lacritin doses were performed. In time course experiments, pS6K1 was found to be phosphorylated by mTOR, a serine/threonine kinase inhibitable by rapamycin in complex with FK506-binding protein 12.

To differentiate the relative contributions of each pathway to mitogenesis, cells can be preincubated with cyclosporine and/or rapamycin.

EXAMPLE 6

Identification of Syndecan-1 as a Coreceptor for Prosecretory Mitogen

Methods

Biotinylated cell surface proteins were applied to lacritin affinity columns. After washing extensively in physiological salt-containing buffer, bound protein was eluted with 1 M NaCl, and identified with avidin-peroxidase using an ECL blot method. In controls, columns lacking lacritin were used. Human syndecan-1 plasmid DNA was stably transfected into lacritin unresponsive HEK293 cells. 293T cells stably transfected with human syndecan-2 or –4 were kindly provided by Dr. Atsushi Utani (Chiba University). A series of lacritin C-terminal and N-terminal deletion mutants were generated. Pull down binding assays involved incubation of intein-tagged lacritin or intein deletion mutants with lysates of untransfected or transfected cells followed by precipitation and SDS PAGE. Immunolocalization of syndecan-1 in human lacrimal glands was performed using anti-human syndecan-1 antibody (CD138).

Results

The first of approximately four bands repeatedly eluted from lacritin affinity column was determined by sequencing to be syndecan-1. In pull-down assays, lacritin bound mammalian syndecan-1, but not syndecan-2 or 4. The binding appeared to be independent of heparan sulfate side chains, in keeping with lack of lacritin binding to heparin (previously known). Deletion of lacritin's C-terminal 25 but not N-terminal 5, 10, or 24 amino acids eliminated binding. Soluble lacritin and N-terminal 24 deletion mutant but not heparin and C-terminal deletion mutants inhibited binding in competitive binding assays. Syndecan-1 was detected in 'near apical' and basolateral plasma membranes in human lacrimal gland.

CONCLUSIONS

Syndecan-1, a coreceptor for FGF's, Wnt's and other growth factors appears to serve in the same capacity for lacritin, but in a unique manner apparently independent of heparan sulfate side chains. Dependence on lacritin's C-terminal 25 amino acids for binding, as well as mitogenesis and calcium signaling, suggests involvement of lacritin's C-terminal amphipathic α-helix in lacritin-receptor interactions.

EXAMPLE 7

Tumor Necrosis Factor-Induced Apoptosis in Corneal Epithelial Cells is Attenuated by Lacritin Background Cell survival is critical during corneal epithelial regeneration after infection or injury and novel lacrimal glycoprotein, lacritin, could be fundamental in cytoprotection and cell proliferation. As described in more detail above, the lacrimal-corneal axis is a fundamental regulator of ocular health and plays a key role in ocular surface inflammation associated with Dry Eye Syndromes and corneal injury. In particular, a host of mediators are implicated in the development and progression of corneal inflammation, such as the proinflammatory cytokines TNF-α, IL-1β, IL-6 and the chemokine IL-8. The role of lacritin in the stimulation of a putative G-protein coupled receptor (GPCR) dependent pathway regulating corneal epithelial cell turnover was examined with respect to a mechanism involving increased calcium signaling involving protein kinase C(PKC), and its crosslink with a tumor necrosis factor (TNF-α)-induced apoptosis in a human corneal epithelial cell line (HCE).

Methods

Lacritin-induced proliferation and calcium signaling was studied in the human corneal epithelial (HCE) cell line. HCE cells were grown at 37° C. in DMEM F/12 supplemented with 10% FBS and 50 μg/ml gentamicin. Each experiment was done in a dose- and time-dependent manner using TNF-α (5-20 ng/ml) and lacritin (1-10 nM). Cell viability was measured spectrophotometrically at an absorbance of 570 nm using the MTT assay. Caspase-8 activity was detected fluorometrically by measuring cleavage of the fluorogenic substrate IETD-pNA at an excitation wavelength of 405 nm. Lacritin-induced cell proliferation was studied by H3-thymidine incorporation and via fluorescence-based detection of PKC, PLC and cAMP. Calcium signaling was detected by confocal microscopy of Fluo-4 loaded cells.

Results

Figure 10:
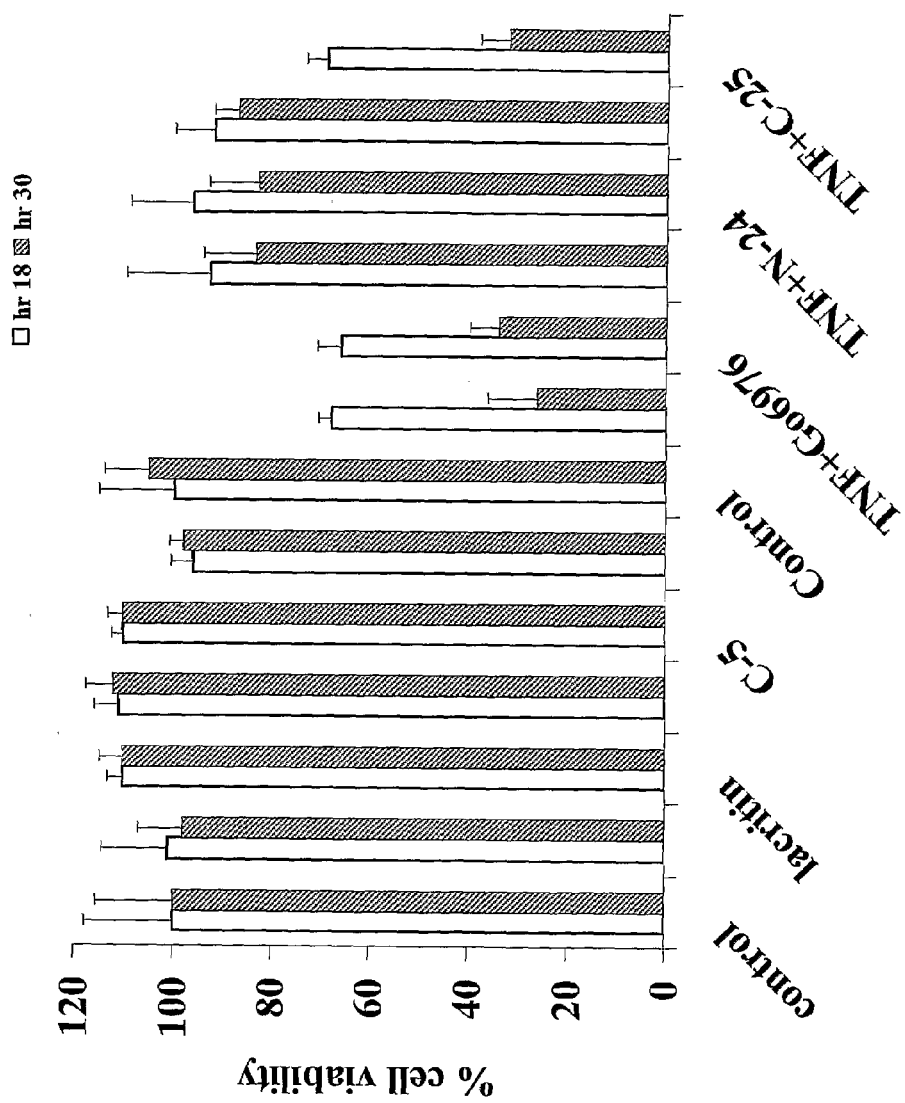
FIG. 10 graphically illustrates the ability of lacritin and fragments of lacritin to protect human corneal epithelial cells from tumor necrosis factor-induced cell death. The groups include treatment with Go6976 (inhibitor of protein kinase C), lacritin, lacritin lacking 24 N-terminal amino acids (N-24), lacritin lacking 5 C-terminal amino acids (C-5), and lacritin lacking 25 C-terminal amino acids (C-25), tumor necrosis factor, control (no treatment) and combinations of these agents. The ordinate indicates % cell viability. White bars indicate 18 hours and diagonally-hatched bars indicate 30 hours.

TNF-α-induced cell death in HCE cells (32.2±2.6% after 18 hr and 73.7±10% after 30 hr) was attenuated by lacritin (10 nM) pretreatment (FIG. 10). The data in FIG. 10 compare the cell viability of human corneal epithelial cells in culture after 18 or 30 hours of exposure to Go6976 (inhibitor of protein kinase C), lacritin, lacritin lacking 24 N-terminal amino acids (N-24), lacritin lacking 5 C-terminal amino acids (C-5), and lacritin lacking 25 C-terminal amino acids (C-25). At right half, viability in the presence of proinflammatory cytokine TNF. TNF alone reduces viability of the HCE and induces apoptosis. Go6976 and C-5 have no effect on viability loss. In contrast, lacritin, N-24 and C-5 all protect human corneal epithelial cells from TNF-induced cell death.

Figure 11:
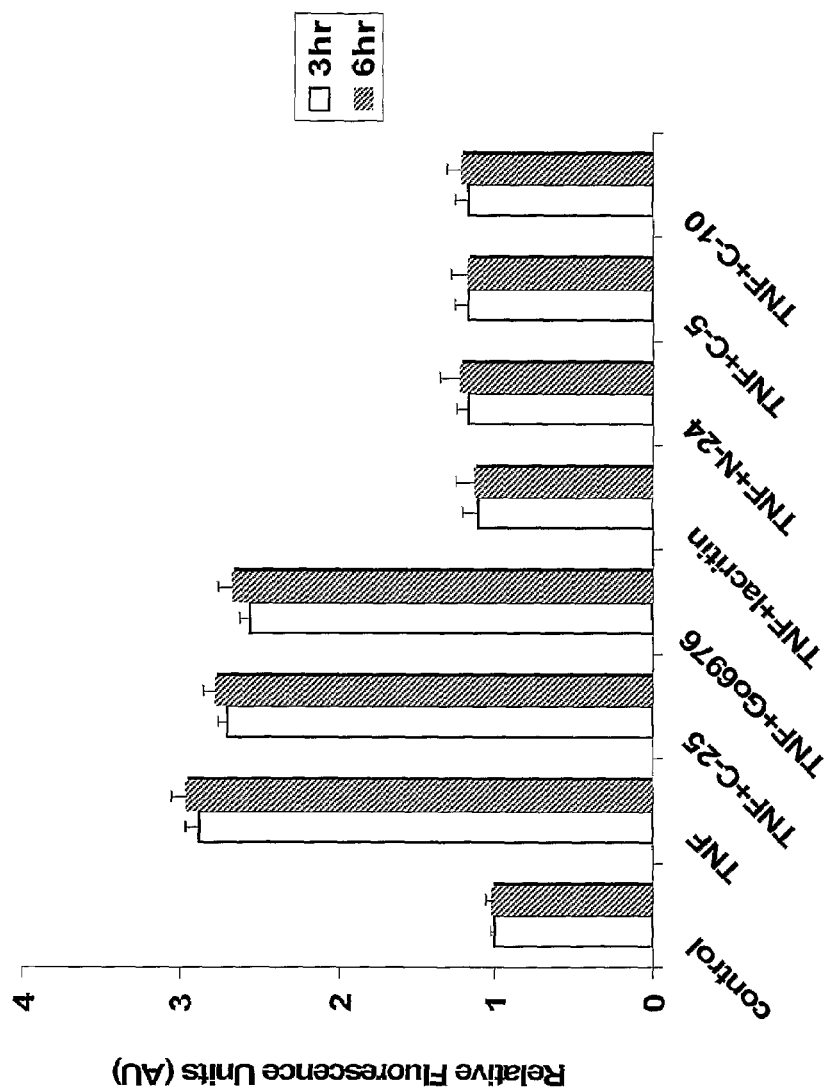
FIG. 11 graphically illustrates the ability of lacritin and fragments of lacritin to inhibit the ability of tumor necrosis factor (TNF) to regulate caspase-3 activity in human corneal epithelial cells. Go6976 is an inhibitor of protein kinase C. The ordinate represents relative fluorescence units. White bars indicate 3 hours and diagonally-hatched bars indicate 6 hours.

TNF-α induced a three-fold increase in the proapoptotic caspase-8 activity, which was completely blocked by lacritin pretreatment (FIG. 11). The data presented in FIG. 11 compare Caspase-3 activity in human corneal epithelial cells. Caspase-3 is used as a marker of cell death by apoptosis. TNF promotes apoptosis. The deletion mutant C-25 and Go6976 do not protect against cell death. Lacritin, and the lacritin deletion mutants N-24, C-5, and C-10 protect human corneal epithelial cells from cell death by TNF.

Figure 12:
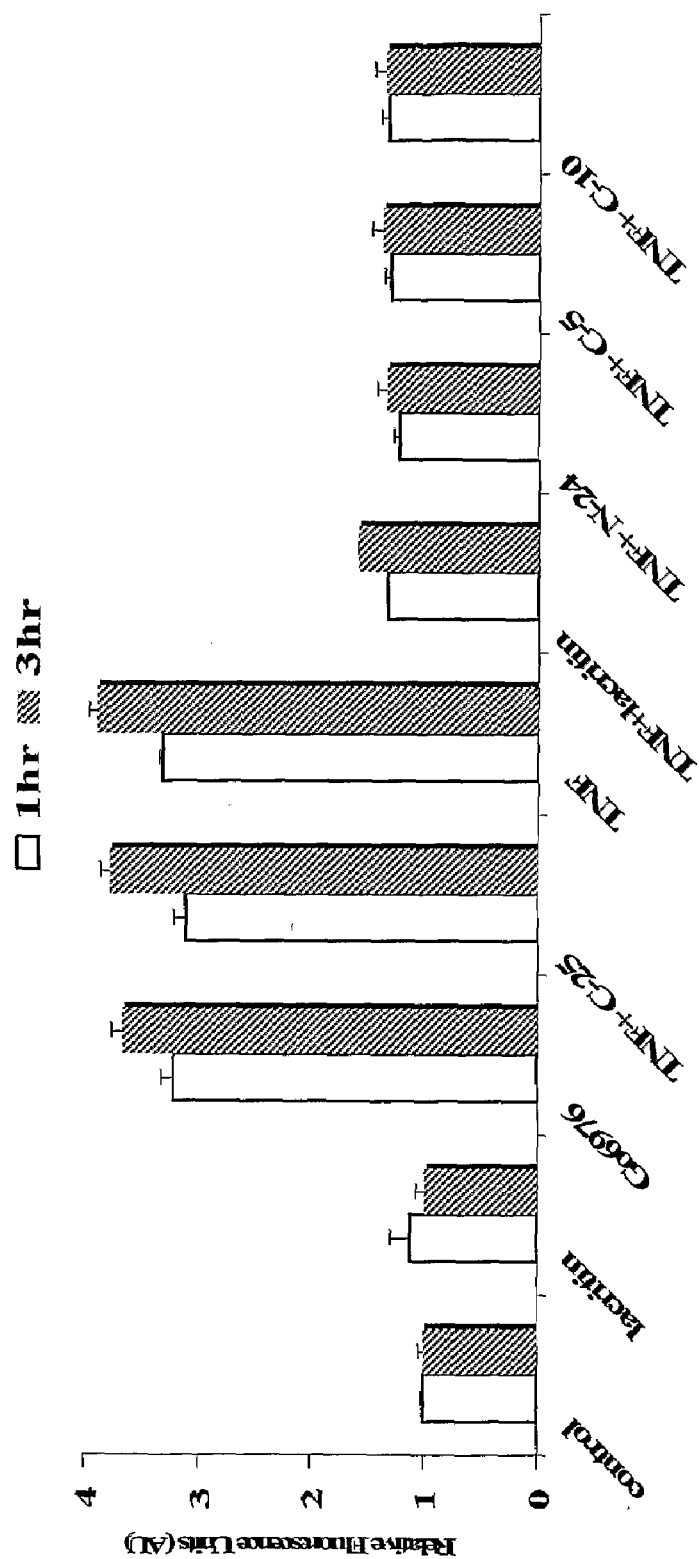
FIG. 12 graphically illustrates the ability of lacritin polypeptides to block TNFα induced caspase-8 activity in human corneal epithelial cells. The ordinate represents relative fluorescence units. White bars indicate 1 hour and diagonally-hatched bars indicate 6 hours.

Caspase-8 activity was measured in human corneal epithelial cells treated with various combinations of TNF-α, fragments of lacritin, and the PKC inhibitor Go6976. TNF-α induced a multifold increase in caspase-8 activity which is blocked by lacritin and its deletion constructs C-5, C-10 and N-24 (see FIG. 12). The PKC-α inhibitor Go6976 and C-25 fail to block this increase of the upstream initiator caspase-8.

Figure 13:
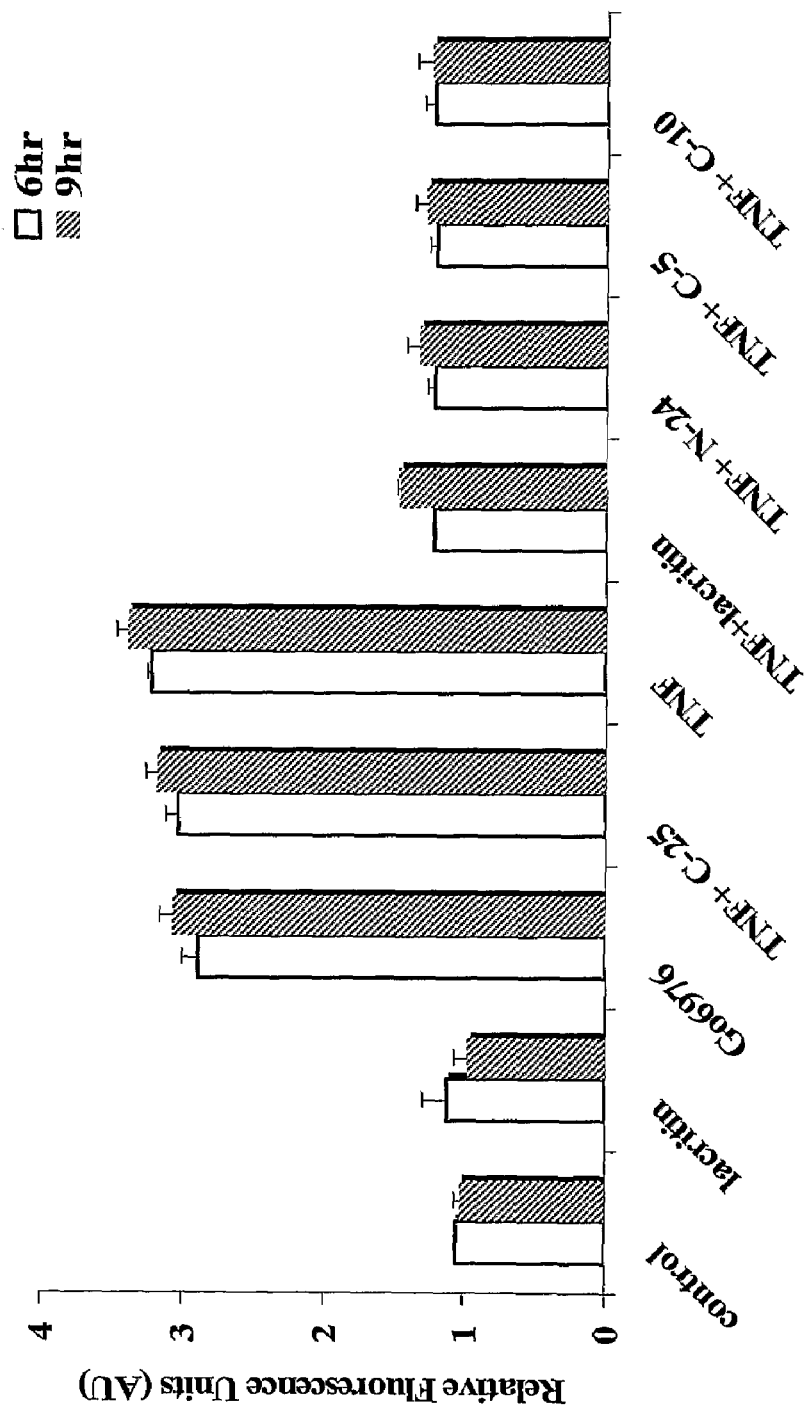
FIG. 13 graphically illustrates the ability of lacritin polypeptides (10 nM) to block TNFα induced caspase-9 activity in human corneal epithelial cells. The ordinate represents relative fluorescence units. White bars indicate 6 hours and diagonally-hatched bars indicate 9 hours.

Caspase-9 activity was measured in cells treated with various combinations of TNF-α, fragments of lacritin, and the PKC inhibitor Go6976. TNF-α induced a multifold increase in caspase-9 activity, which is blocked by lacritin (10 nm) and its deletion constructs C-5, C-10 and N-24 (see FIG. 13). The PKC-α inhibitor Go6976 and C-25 fail to block this increase of the downstream initiator caspase-9.

Figure 14:
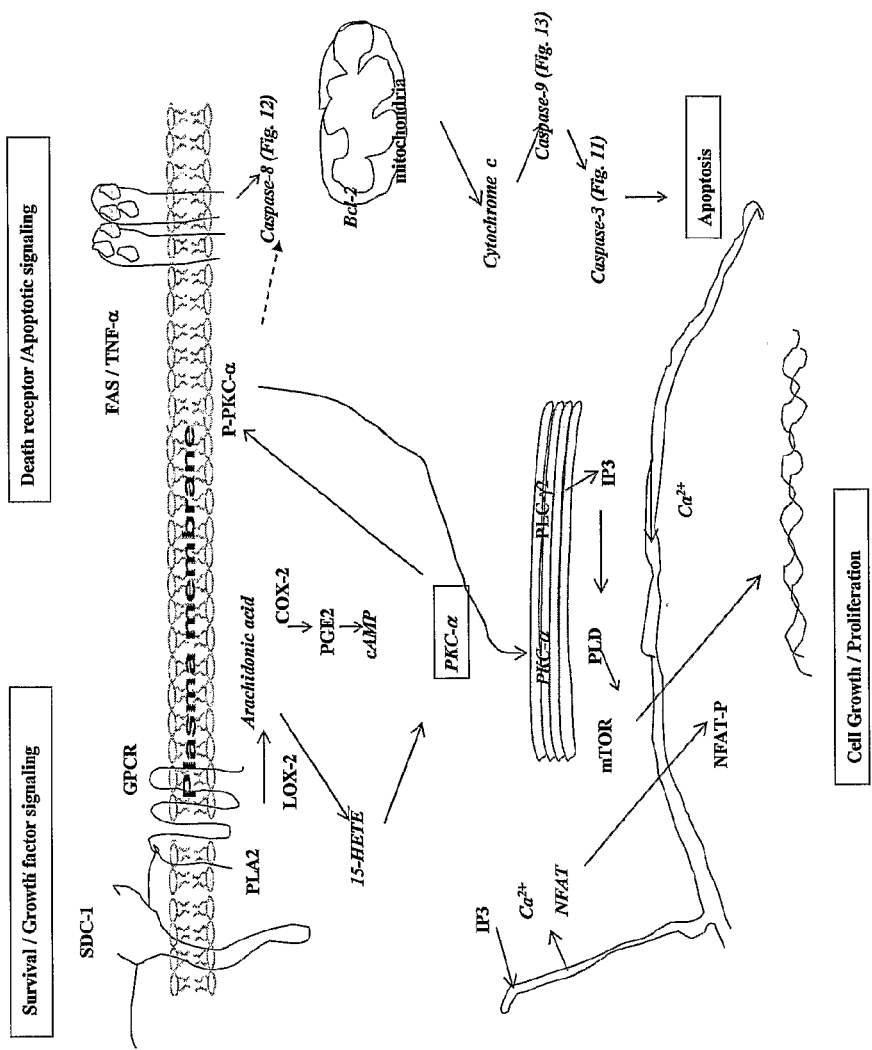
FIG. 14 is a schematically summarizes the various signaling pathways involved in cell survival/growth signaling, death receptor/apoptotic signaling, and cell growth/proliferation, as described above.

FIG. 14 is a schematic representation summarizing the various signaling pathways involved in cell survival/growth signaling, death receptor/apoptotic signaling, and cell growth/proliferation, as described above.

It will be appreciated by those of ordinary skill in the art that the ability of a lacritin polypeptide to inhibit the inflammatory effects of TNF, such as apoptosis, can be applied to the use of a lacritin polypeptide to inhibit the effects of other proinflammatory cytokines and agents as well.

Lacritin and its deletion construct (N-24) promote cell proliferation as measured by the thymidine incorporation in HCE cells (see above).

The present invention demonstrates that lacritin promotes the synthesis and secretion of the mucin MUC16 by human corneal epithelial cells. MUC16 is an important mucin on the ocular surface. Mucin contributes to the tear film, is important for wetting the ocular surface, and is reduced in Sjogren's syndrome patients. Specifically, human corneal epithelial cells were treated with either lacritin (10 nM) or the inactive deletion mutant of lacritin, C-25 (10 nM). Cells were blotted for MUC16. MUC16 secretion was greatly enhanced in lacritin treated cells, relative to those treated with the inactive mutant C-25.

Conclusions

The novel prosecretory mitogen, lacritin, promotes cell proliferation and offers cytoprotection to the corneal epithelial cells against TNF-α-induced cell death. Signal transduction events related to this cytoprotection and proliferation of the corneal epithelial cells are under investigation.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inhibiting epithelial cell apoptosis or other form of epithelial cell death, wherein the cells have been subjected to an insult selected from the group consisting of blepharitis, Dry Eye, conjunctivitis, Sjogren's syndrome, corneal abrasion, ulceration, bacterial infection, direct trauma, surgery, radiant energy, ionizing energy, viral infection, fungal infection, parasitic infection, keratitis, systemic dermatologic disorders, collagen vascular diseases, Reiter's disease, and Behcet's disease, said method comprising contacting said cells before or after the insult with a composition comprising an effective amount of a polypeptide which comprises the amino acid sequence of SEQ ID NO: 4, 10, 16, 17, 18, and 19, and a pharmaceutically acceptable carrier, thereby inhibiting epithelial cell apoptosis or other form of epithelial cell death.

2. The method of claim 1, wherein said cells are selected from the group consisting of corneal epithelial cells, lacrimal acinar cells, and salivary ductal cells.

3. The method of claim 1 wherein said insult comprises a bacterial or viral infection.

4. The method of claim 1, wherein said insult comprises inflammation induced by a foreign object.

5. The method of claim 1, wherein said insult is inflammation induced by a proinflammatory cytokine.

6. The method of claim 1, wherein said insult is inflammation induced by a lack of sufficient tear production.

7. The method of claim 1, wherein said insult is an ocular associated surgical procedure.

8. The method of claim 1, wherein said cells are human cells.

* * * * *

UNITED STATES PATENT AND TRADEMARK OFFICE
CERTIFICATE OF CORRECTION

PATENT NO. : 7,648,964 B2  Page 1 of 1
APPLICATION NO. : 11/596506
DATED : January 19, 2010
INVENTOR(S) : Laurie et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 185 days.

Signed and Sealed this

Twenty-third Day of November, 2010

David J. Kappos
*Director of the United States Patent and Trademark Office*